US010941200B2

(12) United States Patent
Haass et al.

(10) Patent No.: US 10,941,200 B2
(45) Date of Patent: Mar. 9, 2021

(54) TREM2 CLEAVAGE MODULATORS AND USES THEREOF

(71) Applicants: Deutsches Zentrum Für Neurodegenerative Erkrankungen EV, Bonn (DE); Ludwig-Maximilians-Universität München, Munich (DE)

(72) Inventors: Christian Haass, Icking (DE); Gernot Kleinberger, Munich (DE); Kai Schlepckow, Germering (DE)

(73) Assignees: Deutsches Zentrum Für Neurodegenerative Erkrankungen EV, Bonn (DE); Ludwig-Maximilians-Universität München, München (DE)

( * ) Notice: Subject to any disclaimer, the term of this patent is extended or adjusted under 35 U.S.C. 154(b) by 0 days.

(21) Appl. No.: 16/319,373

(22) PCT Filed: Jul. 24, 2017

(86) PCT No.: PCT/EP2017/068684
§ 371 (c)(1),
(2) Date: Jan. 21, 2019

(87) PCT Pub. No.: WO2018/015573
PCT Pub. Date: Jan. 25, 2018

(65) Prior Publication Data
US 2019/0185565 A1   Jun. 20, 2019

(30) Foreign Application Priority Data
Jul. 22, 2016   (EP) .................................... 16180844

(51) Int. Cl.
*C07K 16/28* (2006.01)
*A61P 21/00* (2006.01)
*A61P 25/28* (2006.01)
*A61P 25/16* (2006.01)

(52) U.S. Cl.
CPC .......... *C07K 16/2803* (2013.01); *A61P 21/00* (2018.01); *A61P 25/16* (2018.01); *A61P 25/28* (2018.01); *C07K 2317/34* (2013.01); *C07K 2317/76* (2013.01)

(58) Field of Classification Search
CPC ............ C07K 16/2803; C07K 2317/34; C07K 2317/76; A61P 21/00; A61P 25/28; A61P 25/16
See application file for complete search history.

(56) References Cited

FOREIGN PATENT DOCUMENTS

| CN | 105218669 A | 1/2016 |
|---|---|---|
| WO | 2016023019 A2 | 2/2016 |
| WO | 2017062672 A2 | 4/2017 |

OTHER PUBLICATIONS

Yuen et al., Nature Methods, 4(12):995-7, December (Year: 2007).*
International Search Report and Written Opinion dated Jan. 25, 2018 and received in PCT/EP2017/068684.
Wunderlich et al., "Sequential Proteolytic Processing of the Triggering Receptor Expressed on Myeloid Cells-2 (TREM2) Protein by Ectodomain Shedding and γ-Secretase-Dependent Intramembranous Cleavage", The Journal of Biological Chemistry, vol. 288, No. 46, pp. 33027-33036, (2013).
International Preliminary Report on Patentability dated Jan. 31, 2019 for PCT/EP2017/068684.

* cited by examiner

*Primary Examiner* — Kimberly Ballard
*Assistant Examiner* — Stacey N MacFarlane
(74) *Attorney, Agent, or Firm* — Michele M. Wales; Inhouse Patent Counsel, LLC

(57) ABSTRACT

The present invention relates to a binding molecule having a binding site within the ectodomain of the triggering receptor expressed on myeloid cells 2 (TREM2), wherein the binding molecule inhibits TREM2 cleavage. Said binding molecule is particularly useful for treating and/or preventing a neurological disorder, such as a neurodegenerative disorder. Also encompassed by the present invention is a pharmaceutical composition for use in treating and/or preventing a neurological disorder, wherein the pharmaceutical composition comprises the binding molecule of the present invention. Neurodegenerative disorders that may be treated and/or prevented by using the binding molecule of the present invention include Alzheimer's disease (AD), Frontotemporal lobar degeneration (FTLD), FTLD-like syndrome, Parkinson's disease, Nasu-Hakola disease, Multiple sclerosis (MS), Huntington disease, immune-mediated neuropathies, or Amyotrophic lateral sclerosis (ALS).

Figure 1:
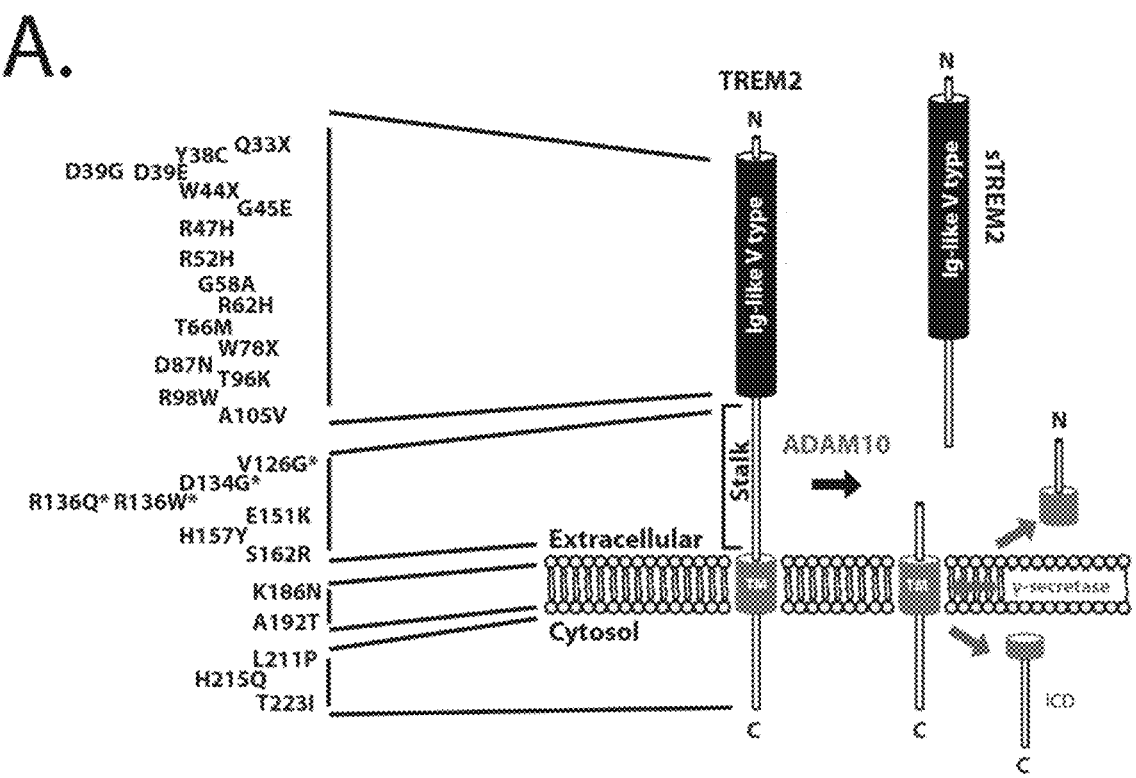
Figure 1:
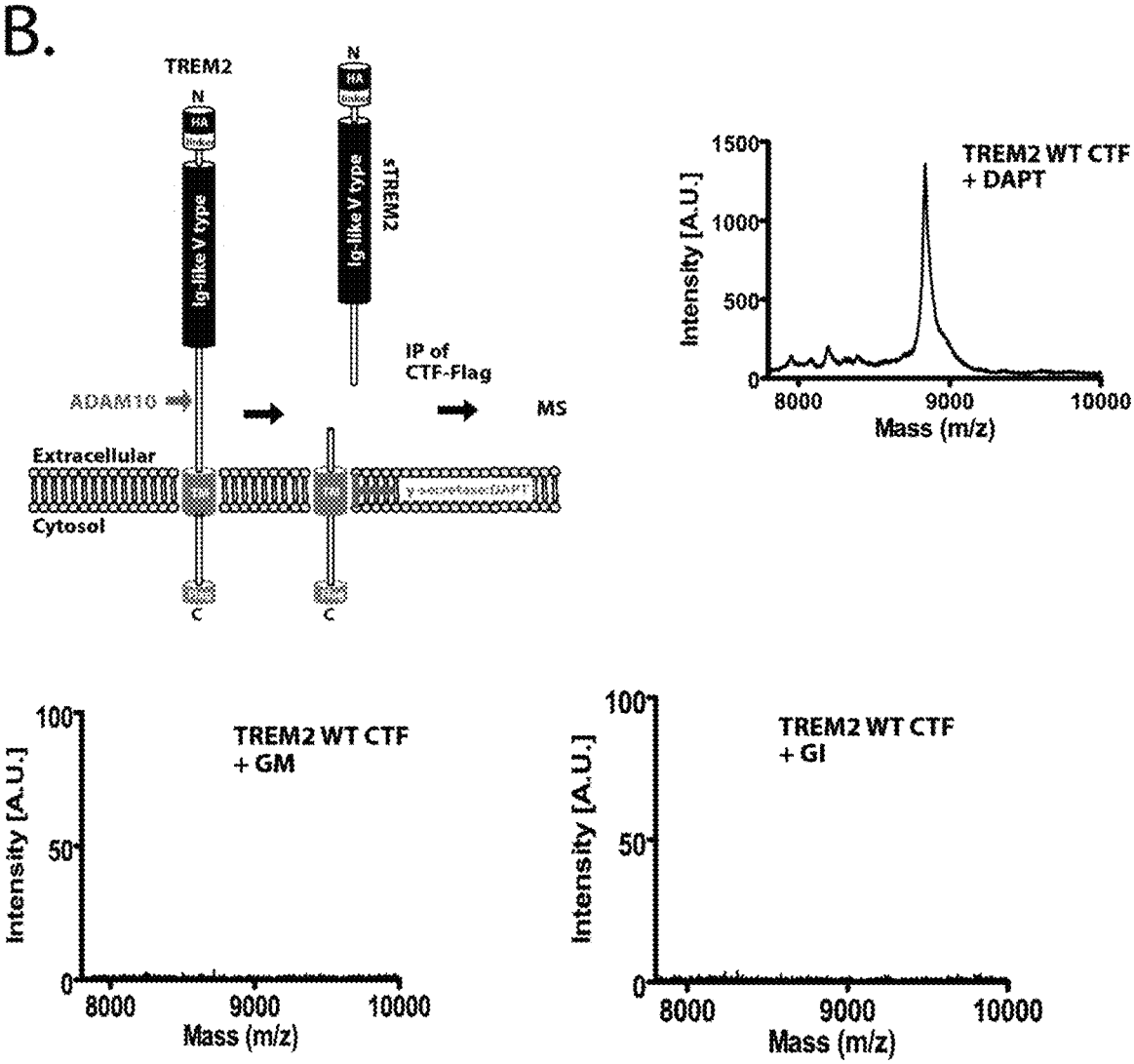
Figure 1:
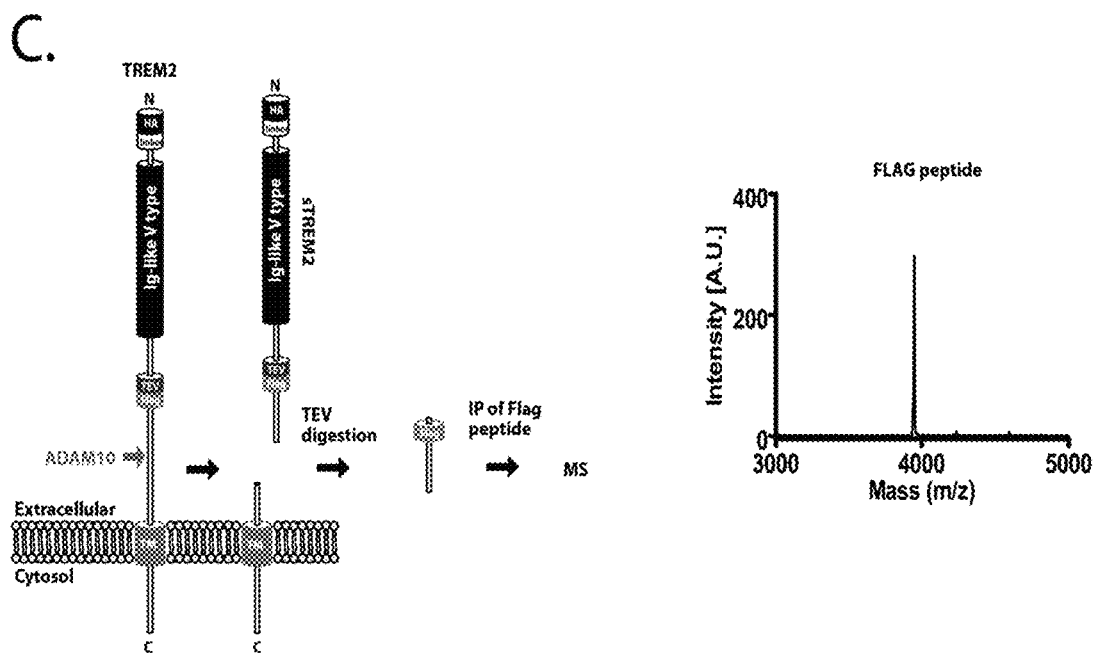
Figure 1:
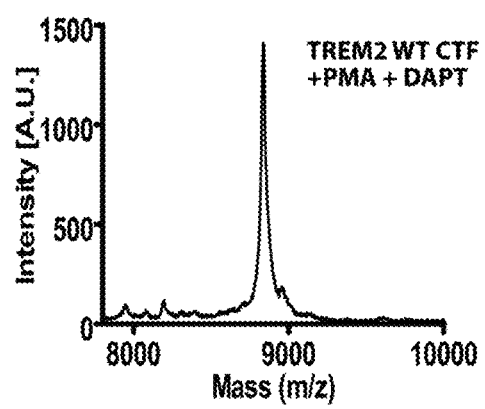
Figure 1:
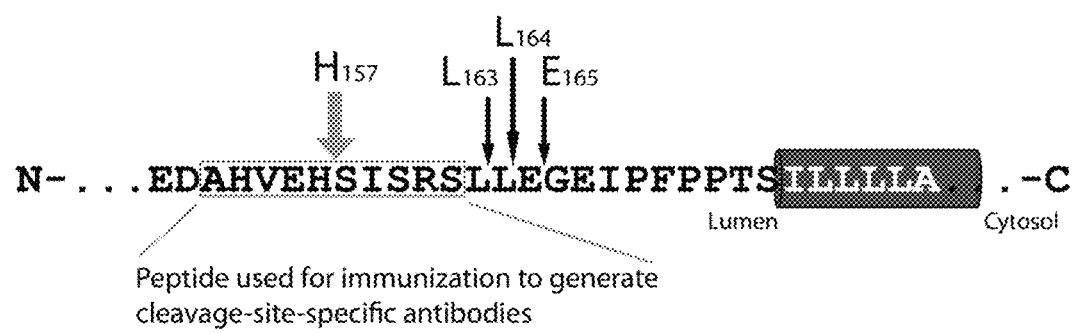

21 Claims, 17 Drawing Sheets
Specification includes a Sequence Listing.

D.

E.

Peptide used for immunization to generate cleavage-site-specific antibodies

Phagocytosis experiments in HEK293 FlpIn cells
stably expressing TREM2-DAP12 fusion construct (see Kleinberger et al. 2014)

1h: n=3 experiments
2h: n=2-4 experiments

Figure 9
A

| Clone name | Variable region of the heavy chain | SEQ ID NO |
|---|---|---|
| 14D3 | EVKLLEFGGGLVQPGGSMRLSCAASGFTFTDFYMNWIRQPAGRAPEWLGLIRNKTKGYTTEYNRSVKGRFTISRDNTQNML YLQMNSLRPEDTATYYCARIGVNNGGSLDYWGQGVMVTVSS | 23 |
| 14D8 | EVKLLESGGGLVQPGGSMRLSCAASGFTFTDFYMNWIRQPAGKAPEWLGLIRNKANGYTTVYNPSVKGRFTISRDNTQNML YLQMNTLRGEDTATYYCARIGINNGGSLDYWGQGVMVTVSS | 24 |
| 7A12 | EVKLLESGGGLVQPGGSMRLSCAASGFTFTDFYMNWIRQPAGKAPEWLGLIRNKANGYTTQYNPSVKGRFTISRDNTQNML YLQMNTLRGEDTATYYCARIGINNGGSLDYWGQGVMVTVSS | 25 |
| 8A11 | EVKLLESGGGLVQPGGSMRLSCAASGFTFTDFYMNWIRQPAGKAPEWLGLIRNKTKGYTTEYNTSVKGRFTISRDNTQNML YLQMNSLRPEDTATYYCARIGVNNGGSLDYWGQGVMVTVSS | 26 |
| 21A3 | EVKLLESGGGLVQPGGSMRLSCAASGFTFTDFYMNWIRQPAGKAPEWLGLIRNKANGYTTQYNPSVKGRFTISRDNTQNML YLQMNTLRGEDTATYYCARIGINNGGSLDYWGQGVMVTVSS | 27 |
| 10C3 | EVKLLESGGGLVQPGGSMRLSCAASGFTFTDFYMNWIRQPAGETPEWLGLIRNKTKGYTTEYNPSVKGRFTISRDNTQNML YLQMNSLRPEDTATYYCARIGINTNGGSLDYWGQGVMVTVSS | 28 |
| 18F9 | EVKLLESGGGLVQPGGSMRLSCVVSGFTFTDFYMNWIRQAAGKAPEWLGLIRNKVNGYRTEYNPSVKGRFTISRDNIQNML YLQMNTLRAEDTATYYCARIGINNGGSLDYWGQGVMVTVSS | 29 |
| 15C5 | EVKLLESGGGLVQPGGSMRLSCAASGFTFTDFYMNWIRQPAGKAPEWLGLIRNKAYGYTTEYNPSVKGRFTISRDNTQDML YLQMNTLRAEDTATYYCARIGINYGGSLDYWGQGVMVTVSS | 30 |
| 1G6 | EVKLLESGGGLIRLSCVASGFTFTDFYMNWIRQPAGKAPEWLGLIRNKANGFTTEYNPSVKGRFTISRDNTQHML YLQMNTLRAEDTATYYCARIGINNGGSLDYWGQGVMVTVSS | 31 |
| Consensus sequence | EVKLLESGGGLVQPGGSMRLSCAASGFTFTDFYMNWIRQPAGKAPEWLGLIRNKanGYTTeYNPSVKGRFTISRDNTQNML YLQMNtLR*EDTATYYCARIGiNNGGSLDYWGQGVMVTVSS | 32 |

Figure 9 cont. B

| Clone name | Variable region of the light chain | SEQ ID NO |
|---|---|---|
| 14D3 | DILIIQSPASLTVSAGARVTMSCKSSQSLLYSENNQDYLAWYQQKPGQFPKLLIYGASNRHTGVPDRFTGSSGTDFTLTI SSVQAEDLADYYCEQTYSYPYTFGAGTKLELK | 33 |
| 14D8 | DILINQSPASLTVSTGEKVTMSCRSSQSLLYSERNQDYLAWYQQKPGQFPKLLIYGASYRHTGVPDRFTGSSGTDFTLTI SSVQAEDLADYYCEQTYSYPYTFGAGTKLELK | 34 |
| 7A12 | DILINQSPASLTVSAGEKVTMSCKSSQSLLYSERNQDYLAWYQQKPGQSPKLLMYGASYRHTGVPDRFTGSSGTDFTLTI SSVQAEDLADYYCEQTYSYPYTFGAGTKLELK | 35 |
| 8A11 | DILIIQSPASLTVSAGARVTMSCKSSQSLLYSENNQDYLAWYQQKPGQFPKLLIYGASNRHTGVPDRFTGSSGTDFTLTI SSVQAEDLADYYCEQTYSYPYTFGAGTKLELK | 36 |
| 21A3 | DILINQSPASLTVSAGEKVTMSCKSSQSLLYSEKNQDYLAWYQQKPGQSPKLLMYGASYRHTGVPDRFTGSSGTDFTLTI SSVQAEDLADYYCEQTYSYPYTFGAGTKLELK | 37 |
| 10C3 | DILIIQSPASLTVSAGARVTMSCKSSQSLLYSENNQDYLAWYQQKPGQFPKLLIYGASNRHTGVPDRFTGSSGTDFTLTI SSVQAEDLADYYCEQTYSYPYTFGAGTKLELK | 38 |
| 18F9 | DILINQSPASLTVSAGEKVTMSCKSSQSLLYSENNQDYLAWYQQKPGQFPKLLIYGASNRHTGVPDRFTGSSGTDFTLTI SSVQAEDLADYYCEQTYSYPYTFGAGTKLELK | 39 |
| 15C5 | DILINQSPASLTVSAGEKVTVSCKSSQSLLYSESNQDYLAWYQQKPGQFPKLLIYGASYRHTGVPDRFTGSSGTDFTLTI SSVQAEDLAHYYCEQTYSYPYTFGAGTKLELK | 40 |
| 1G6 | DILINQSPASLTVSTGEKVTMSCKSSQSLLYSENKQDYLAWYQQKPGQFPKLLIYGASNRHTGVPDRFTGSSGTDFTLTI NIVQAEDLADYYCEQTYSYPYTFGAGTKLELK | 41 |
| Consensus sequence | DILInQSPASLTVSAGekVTMSCKSSQSLLYSEnNQDYLAWYQQKPGQFPKLLIYGASnRHTGVPDRFTGSSGTDFTLTI SSVQAEDLADYYCEQTYSYPYTFGAGTKLELK | 42 |

Figure 9 cont.
C

| Clone name | Complementarity determining regions in the variable region of the heavy chain | | | | | |
|---|---|---|---|---|---|---|
| | CDR1 | SEQ ID NO | CDR2 | SEQ ID NO | CDR3 | SEQ ID NO |
| 14D3 | GFTFTDFY | 43 | IRNKTKGYTT | 53 | ARIGVNNGGSLDYWG | 63 |
| 14D8 | GFTFTDFY | 44 | IRNKANGYTT | 54 | ARIGINNGGSLDYWG | 64 |
| 7A12 | GFTFTDFY | 45 | IRNKANGYTT | 55 | ARIGINNGGSLDYWG | 65 |
| 8A11 | GFTFTDFY | 46 | IRNKTKGYTT | 56 | ARIGVNNGGSLDYWG | 66 |
| 21A3 | GFTFTDFY | 47 | IRNKANGYTT | 57 | ARIGINNGGSLDYWG | 67 |
| 10C3 | GFTFTDFY | 48 | IRNKTKGYTT | 58 | ARIGTNNGGSLDYWG | 68 |
| 18F9 | GFTFTDFY | 49 | IRNKVNGYRT | 59 | ARIGINNGGSLDYWG | 69 |
| 15C5 | GFTFTDFY | 50 | IRNKAYGYTT | 60 | ARIGINYGGSLDYWG | 70 |
| 1G6 | GFTFTDFY | 51 | IRNKANGFTT | 61 | ARIGINNGGSLDYWG | 71 |
| Consensus sequence | GFTFTDFY | 52 | IRNKanGYTT | 62 | ARIGiNNGGSLDYWG | 72 |

Figure 9 cont.
D

| Clone name | Complementarity determining regions in the variable region of the light chain | | | | | |
|---|---|---|---|---|---|---|
| | CDR1 | SEQ ID NO | CDR2 | SEQ ID NO | CDR3 | SEQ ID NO |
| 14D3 | QSLLYSENNQDY | 73 | GAS | 83 | EQTYSYPYT | 93 |
| 14D8 | QSLLYSEKNQDY | 74 | GAS | 84 | EQTYSYPYT | 94 |
| 7A12 | QSLLYSEKNQDY | 75 | GAS | 85 | EQTYSYPYT | 95 |
| 8A11 | QSLLYSENNQDY | 76 | GAS | 86 | EQTYSYPYT | 96 |
| 21A3 | QSLLYSEKNQDY | 77 | GAS | 87 | EQTYSYPYT | 97 |
| 10C3 | QSLLYSENNQDY | 78 | GAS | 88 | EQTYSYPYT | 98 |
| 18F9 | QSLLYSESNQDY | 79 | GAS | 89 | EQTYSYPYT | 99 |
| 15C5 | QSLLYSEKNQDY | 80 | GAS | 90 | EQTYSYPYT | 100 |
| 1G6 | QSLLYSENKQDY | 81 | GAS | 91 | EQTYSYPYT | 101 |
| Consensus sequence | QSLLYSEnnQDY | 82 | GAS | 92 | EQTYSYPYT | 102 |

TREM2 CLEAVAGE MODULATORS AND USES THEREOF

CROSS-REFERENCE TO RELATED APPLICATIONS

This application is a § 371 National Stage Application of PCT/EP2017/068684 filed on Jul. 24, 2017, which claims priority to EP 16180844.9 filed on Jul. 22, 2016. Both of these documents are hereby incorporated by reference in their entirety.

The present invention relates to a binding molecule having a binding site within the ectodomain of the triggering receptor expressed on myeloid cells 2 (TREM2), wherein the binding molecule inhibits TREM2 cleavage. Said binding molecule is particularly useful for treating and/or preventing a neurological disorder, such as a neurodegenerative disorder. Also encompassed by the present invention is a pharmaceutical composition for use in treating and/or preventing a neurological disorder, wherein the pharmaceutical composition comprises the binding molecule of the present invention. Neurodegenerative disorders that may be treated and/or prevented by using the binding molecule of the present invention include Alzheimer's disease (AD), Frontotemporal lobar degeneration (FTLD), FTLD-like syndrome, Parkinson's disease, Huntington disease, polycystic lipomembranous osteodysplasia with sclerosing leukoencephalopathy (PLOSL; also known as Nasu-Hakola disease), Multiple sclerosis (MS), Huntington disease, Guillain-Barré syndrome, chronic inflammatory demyelinating polyneuropathies, Charcot-Marie-Tooth disease or Amyotrophic lateral sclerosis (ALS).

Neurodegeneration corresponds to any pathological condition primarily affecting neurons and represents a large group of neurological disorders with heterogeneous clinical and pathological expressions affecting the function and survival of specific subsets of neurons in specific functional anatomic systems [1]. Inflammation and activation of brain resident immune cells are common hallmarks of numerous neurological disorders and a pivotal role of microgliosis specifically in neurodegenerative disorders has been recognized since a long time [2, 3].

A central role of microglial function in disease pathogenesis is now further supported by the identification of sequence variants in the triggering receptor expressed on myeloid cells 2 (TREM2). While homozygous TREM2 variants cause PLOSL/Nasu Hakola disease [4] or FTD-like dementia [5], heterozygous TREM2 variants are associated with an increased risk for several neurological and neurodegenerative disorders such as Alzheimer's disease (AD), Frontotemporal lobar degeneration (FTLD), Parkinson's disease, FTLD-like syndrome, and Amyotrophic lateral sclerosis (ALS) [5-11] (see also Ulrich, 2016, ACS Chem. Neurosci. 7: 420-427). In brain TREM2 is exclusively expressed in microglia and is functionally required e.g. in phagocytosis of cellular debris [12, 13]. TREM2 is a type-1 membrane protein that is shuttled to the plasma membrane [14] where it may exert its biological functions. TREM2 undergoes regulated intramembrane proteolysis (RIP) [15, 16] (see, e.g. FIG. 1A). RIP is initiated on the cell surface by shedding of full-length TREM2 by metalloproteinases including ADAM10 and ADAM17 (disintegrin and metalloproteinase domain containing proteins) and possibly MMPs (matrix metalloproteinases). Shedding results in the secretion of soluble TREM2 (sTREM2), which can be detected in human cerebrospinal fluid (CSF) [15, 17-19]. The membrane retained C-terminal fragment (CTF) is subsequently cleared by an intramembraneous cleavage by γ-secretase (see, e.g. Kleinberger et al. [15] FIG. 1A) [16, 20].

Several mutations of TREM2 have been functionally investigated. Mutations within the Ig-like domain such as p.T66M and p.Y38C result in misfolding of TREM2 and the retention of the immature protein within the endoplasmic reticulum [15, 21]. As a consequence reduced cell surface TREM2 is observed and shedding is dramatically reduced. Consistent with that, a patient with a homozygous TREM2 p.T66M mutation had extremely low or even no detectable sTREM2 in the serum and CSF [15, 18].

Lowered cell surface TREM2 results in reduced phagocytic activity [15]. Although initially discrepant results regarding the effects of a loss of TREM2 function on amyloid plaque pathology were reported [22, 23], it seems to be clear now that a loss of TREM2 leads to the accumulation of fuzzy amyloid plaques suggesting a lack of phagocytic clearance of the plaque hallow or reduced prevention of amyloid plaque growth [24, 25]. In support of reduced phagocytic plaque degradation, it has recently been shown that immunotherapeutic clearance of amyloid plaques via phagocytosis is reduced in the absence of TREM2 [26]. Mutations that have been so far functionally investigated are located within the Ig-like domain of TREM2 (see, e.g. Kleinberger et al. [15] FIG. 1A). Misfolding of this domain, retention and consequently reduced shedding appear to be a common read out of such TREM2 variants. Recent genetic studies indicated a previously described coding variant (p.H157Y; [9, 27, 28]) to be significantly associated with AD in the Han Chinese population [29]. Interestingly, this variant (p.H157Y) is located outside of the Ig-like domain within the stalk region (see, e.g. Kleinberger et al. [15] FIG. 1A).

Neurological, such as neurodegenerative, disorders have several features in common including atypical protein assemblies and/or induced progressive cell death [30, 31]. Neurodegeneration can be found in many different levels of neuronal circuitry leading to molecular and systemic defects. Certain therapeutic approaches exist aiming at lowering outbreak and/or progression of neurodegenerative disorders. However, unfortunately, neurodegenerative disorders are still incurable, resulting in progressive degeneration and/or death of neuronal cells.

Thus, the technical problem underlying the present invention is the provision of means and methods for the treatment and/or prevention of neurological disorders including neurodegenerative disorders.

The technical problem is solved by the provision of the embodiments described herein and as characterized in the claims.

Accordingly, the present invention relates to a binding molecule having a binding site within the ectodomain of TREM2, wherein the binding molecule inhibits TREM2 cleavage.

As documented herein below and in the appended examples, the exact cleavage site where TREM2 shedding occurs has surprisingly been identified. In particular, in the context of the present invention it has been found that cleavage of TREM2 ectodomain occurs C-terminal to the histidine at position 157 (His157) of the amino acid sequence of TREM2, e.g. as shown in SEQ ID NO: 1 or 4. The binding molecule of the present invention blocks cleavage of the TREM2 ectodomain at this position. Thus, the herein provided binding molecule is stabilizing or increasing the amount of surface-bound TREM2, thereby preserving and stimulating activity of microglial cells. Accordingly, the herein provided binding molecule may effectively contribute to the prevention of the accumulation and the negative effects of amyloid plaques; and thus, provides a novel approach for the treatment and/or prevention of various neurological disorders including neurodegenerative disorders such as Alzheimer's disease (AD).

The cleavage site that has been identified within TREM2 (i.e. His157) is exactly the site where the AD associated TREM2 variant p.H157Y is located. The contribution of TREM2 mutations to the development of neurodegenerative diseases has been described in the prior art. However, the mechanism by which p.H157Y contributes to AD or other neurodegenerative disorders is completely unknown. The appended examples surprisingly demonstrate that the mutant variant p.H157Y leads to a higher TREM2 shedding, a finding opposite to the reduced shedding observed for mutations within the Ig-like domain such as p.T66M and p.Y38C [15]. As also demonstrated by the appended examples, enhanced shedding of TREM2 p.H157Y leads to reduced cell surface full-length TREM2 and to a reduced phagocytic activity. Thus, unexpectedly, mutations located within the Ig-like domain or the stalk region affect TREM2 dependent phagocytic activity via completely different cellular mechanisms. Accordingly, description of the existence of TREM2 mutations such as the p.H157Y variant in the prior art in no way suggests that TREM2 cleavage takes place exactly at this position.

Several molecules that specifically bind to TREM2, such as anti-TREM2 antibodies, are known in the prior art. However, there is no data publicly available showing a binding molecule that is able to inhibit TREM2 ectodomain shedding (i.e. cleavage). The appended examples surprisingly demonstrate that TREM2 ectodomain shedding (i.e. TREM2 cleavage) takes place at His157 of TREM2. Thus, the cleavage enzyme (e.g. ADAM10, ADAM17 or matrix metalloproteinases) has to have access to this amino acid for cleaving TREM2. Accordingly, the appended examples indicate that a binding molecule blocking His157 can successfully inhibit cleavage of TREM2. Access of the cleavage enzyme to His157 may be blocked by directly binding to His157. In addition or alternatively, access of the cleavage enzyme to His157 may be sterically blocked by binding to an amino acid that is located in close proximity (e.g. having a distance of up to 10 amino acids) to His157. For example, an antibody or a small molecule binding to an amino acid that is located in close proximity to His157 may sterically block access of the cleavage enzyme to His157, thereby inhibiting TREM2 cleavage at this site.

Thus, the present invention provides a binding molecule that inhibits (preferably prevents) TREM2 cleavage. More specifically, in the context of the present invention cleavage (i.e. shedding) of the TREM2 ectodomain is inhibited by the binding molecule of the present invention.

The herein provided binding molecule has a binding site within the ectodomain of TREM2. Herein the term "binding site" refers to the part of TREM2 that is recognized (i.e. bound) by the herein provided binding molecule. If the binding molecule of the present invention is an antibody, the binding site corresponds to the epitope of said antibody. The binding site of the herein provided binding molecule may be at any position within the cleavage site of the respective cleavage enzyme (e.g. ADAM10). The distance of the cleavage site of ADAM10 to the transmembrane domain of TREM2 is from 10-30 amino acids. The appended examples demonstrate that the cleavage site of ADAM10 within TREM2 is at position His157 (i.e. 18 amino acids from the transmembrane domain of human TREM2). Further, minor preferred cleavage sites have been found at positions Leu163, Leu164 and Glu165 (i.e. 10-12 amino acids from transmembrane domain of human TREM2). Therefore, the minimal cleavage site of ADAM10 can be predicted to be located within the amino acid sequence consisting of positions 145-174 of the amino acid sequence of human membrane bound TREM2. Accordingly, the minimal cleavage site of ADAM10 can be predicted to be within the amino acid stretch GESESFEDAHVEHSISRSLLEGEIPFPPTS (SEQ ID NO: 16). Thus, a binding molecule of the present invention may bind TREM2 at any amino acid(s) within positions 145-174 of TREM2, e.g. of human or mouse TREM2.

However, binding of TREM2 anywhere within the stalk region may lead to inhibition of the interaction of TREM2 with the cleavage enzyme, and thus, may inhibit TREM2 cleavage. The stalk region of TREM2 is located at amino acid positions 113-174 of human membrane bound TREM2 (e.g. as shown in SEQ ID NO: 1), or at amino acid positions 113-171 of murine membrane bound TREM2 (e.g. as shown in SEQ ID NO: 4). Thus, the binding molecule of the present invention may bind human TREM2 anywhere within the amino acid stretch at positions 113-174 of human membrane bound TREM2, and/or within the amino acid stretch at positions 113-171 of murine membrane bound TREM2.

For example, the binding molecule of the present invention may bind to any one of the amino acids of the positions 148-166 of TREM2, e.g. as shown in any one of SEQ ID NOs: 1-6. In the context of the present invention cleavage of membrane bound TREM2 is inhibited by the herein provided binding molecule. Thus, the binding molecule may bind to any one of the amino acids of the positions 148-166 of membrane bound TREM2, e.g. as shown in SEQ ID NO: 1 or 4. Preferably, the herein provided binding molecule inhibits cleavage (i.e. shedding) of human TREM2. Therefore, the binding molecule may bind to any one of the amino acids at positions 148-166 of human TREM2, e.g. as shown in SEQ ID NOs: 1-3. Even more preferably, the binding molecule of the invention inhibits cleavage of membrane bound human TREM2. Thus, the binding molecule of the invention may bind to any one of the amino acids at positions 148-166 of human membrane bound TREM2, e.g. as shown in SEQ ID NO: 1. Thus, one aspect of the present invention relates to the herein provided binding molecule, wherein the binding site comprises at least one of the positions of human membrane bound TREM2 selected from the group consisting of:

glutamic acid at position 148 (Glu148) of human membrane bound TREM2;

serine at position 149 (Ser149) of human membrane bound TREM2;

phenylalanine at position 150 (Phe150) of human membrane bound TREM2;

glutamic acid at position 151 (Glu151) of human membrane bound TREM2;

aspartic acid at position 152 (Asp152) of human membrane bound TREM2;

alanine at position 153 (Ala153) of human membrane bound TREM2;

histidine at position 154 (His154) of human membrane bound TREM2;

valine at position 155 (Val155) of human membrane bound TREM2;

glutamic acid at position 156 (Glu156) of human membrane bound TREM2;

histidine at position 157 (His157) of human membrane bound TREM2;

serine at position 158 (Ser158) of human membrane bound TREM2;
isoleucine at position 159 (Ile 159) of human membrane bound TREM2;
serine at position 160 (Ser160) of human membrane bound TREM2;
arginine at position 161 (Arg161) of human membrane bound TREM2;
serine at position 162 (Ser162) of human membrane bound TREM2;
leucine at position 163 (Leu163) of human membrane bound TREM2;
leucine at position 164 (Leu164) of human membrane bound TREM2;
glutamic acid at position 165 (Glu165) of human membrane bound TREM2; and
glycine at position 166 (Gly166) of human membrane bound TREM2.

In the context of the present invention it may be desired to design a binding molecule that inhibits cleavage of TREM2 of a non-human animal. Such a binding molecule may, e.g., find use for preclinical animal studies. For example, the binding molecule of the present invention may bind to (and inhibit cleavage of) TREM2 of mouse, rat, rabbit, goat, sheep, guinea pig, ferret and/or monkey. In a prioritized aspect of the present invention the herein provided binding molecule binds to and inhibits cleavage of murine TREM2. Such a binding molecule may bind to any one of the amino acids of positions 148-166 of murine TREM2, e.g. as shown in SEQ ID NO: 4 or 5. It is more prioritized herein that the binding molecule of the invention inhibits cleavage of membrane bound murine TREM2. Thus, the binding molecule of the invention may bind to any one of the amino acids of positions 148-166 of murine membrane bound TREM2, e.g. as shown in SEQ ID NO: 4. Thus, one aspect of the present invention relates to the herein provided binding molecule, wherein the binding site comprises at least one of the positions of murine membrane bound TREM2 selected from the group consisting of:
serine at position 148 (Ser148) of murine membrane bound TREM2;
serine at position 149 (Ser149) of murine membrane bound TREM2;
phenylalanine at position 150 (Phe150) of murine membrane bound TREM2;
glutamic acid at position 151 (Glu151) of murine membrane bound TREM2;
glycine at position 152 (Gly152) of murine membrane bound TREM2;
alanine at position 153 (Ala153) of murine membrane bound TREM2;
glutamine at position 154 (Gln154) of murine membrane bound TREM2;
valine at position 155 (Val155) of murine membrane bound TREM2;
glutamic acid at position 156 (Glu156) of murine membrane bound TREM2;
histidine at position 157 (His157) of murine membrane bound TREM2;
serine at position 158 (Ser158) of murine membrane bound TREM2;
threonine at position 159 (Thr159) of murine membrane bound TREM2;
serine at position 160 (Ser160) of murine membrane bound TREM2;
arginine at position 161 (Arg161) of murine membrane bound TREM2;
asparagine at position 162 (Asn162) of murine membrane bound TREM2;
glutamine at position 163 (Gln163) of murine membrane bound TREM2;
glutamic acid at position 164 (Glu164) of murine membrane bound TREM2;
threonine at position 165 (Thr165) of murine membrane bound TREM2; and
serine at position 166 (Ser166) of murine membrane bound TREM2.

In order to use the same binding molecule for the preclinical studies that are to be used in human therapy, it may be desired that the binding molecule of the present invention binds to amino acids that are the same in membrane bound human and membrane bound mouse TREM2. Therefore, the herein provided binding molecule may bind to any one of the amino acids of positions 149-151, 153, 155-158, 160, 161, and 166 of human membrane bound and murine membrane bound TREM2, e.g. as shown in SEQ ID NO: 1 and 4, respectively.

However, as mentioned above, the herein provided binding molecule may bind to any one of the amino acids at positions 148-166 of TREM2. Preferably, the binding molecule binds to any one of the amino acids at positions 153-166, more preferably at positions 153-162 of TREM2. As mentioned above, it is prioritized that the binding molecule of the present invention binds to and inhibits cleavage of human or murine TREM2, preferably of membrane bound human or murine TREM2, and most preferably of membrane bound human TREM2.

The herein provided binding molecule can bind to a conformational binding site or to a linear binding site within TREM2. If the binding molecule is an antibody, these binding sites are called conformational epitope and linear epitope, respectively. A conformational binding site is composed of a discontinuous section of the amino acid sequence of TREM2. Such a binding site interacts with the binding molecule based on the 3-D structure surface feature, i.e. the tertiary structure of TREM2.

By contrast, linear binding sites interact with the binding molecule based on the primary structure of the amino acid sequence of TREM2. Thus, a linear binding site is formed by a continuous sequence of amino acids of TREM2. For example, the binding site of the herein provided binding molecule within TREM2 may comprise or overlap with any one of the polypeptides consisting of the amino acids at positions 148-157 or 157-166, preferably 149-158 or 156-165, more preferably 150-159 or 155-164, even more preferably 151-165 or 154-163, even more preferably 152-161 or 153-162, and even more preferably 153-162 of TREM2. For example, the binding site may comprise or overlap with the polypeptide consisting of the amino acids at positions 152-156 or 158-162 of TREM2. However, also smaller binding sites of 3-5 amino acids may be used by the herein provided binding molecule. For example, the binding site of the herein provided binding molecule within TREM2 may comprise or overlap with any one of the polypeptides consisting of the amino acids at positions 148-150 or 164-166, preferably 149-151 or 163-165, more preferably 150-152 or 162-164, even more preferably 151-153 or 161-163, even more preferably 152-154 or 160-162, even more preferably 153-155 or 159-161, even more preferably 154-156 or 158-160, even more preferably 155-157 and/or 157-159, and even more preferably 156-158. As mentioned above, it is prioritized that the binding molecule of the present invention binds to and inhibits cleavage of human or murine TREM2, preferably of membrane bound human or murine TREM2, and most preferably of membrane bound human TREM2.

As mentioned above, in the context of the present invention it has surprisingly been identified that TREM2 is cleaved specifically at His157. Therefore, the binding molecule of the present invention either directly binds to His157 or sterically inhibits cleavage at position His157. Thus, a preferred binding site that leads to inhibition of TREM2 cleavage is centered around the cleavage site at position His157. Any binding of a binding molecule (e.g. of an antibody, nanobody or small molecule) in the stalk region of TREM2 that inhibits interaction of TREM2 with the cleavage enzyme (e.g. ADAMs or a matrix metalloproteinases, MMPs) may be used in the context of the present invention. The stalk region of TREM2 is located at positions 113-174 of human TREM2 (e.g. as shown in SEQ ID NO: 1); or at positions 113-171 of murine TREM2 (e.g. as shown in SEQ ID NO: 4). In one aspect of the present invention the binding site of the herein provided binding molecule comprises or overlaps with any one of the polypeptides having an amino acid sequence as shown in any one of SEQ ID NOs: 7-15, 21 and 22. Preferably, the binding site is within the amino acid sequence of SEQ ID NO: 7.

As shown in the appended examples, the protease ADAM10 cleaves TREM2 between positions His157 and Ser158. Thus, it is particularly preferred in the context of the present invention that the binding site of the herein provided binding molecule comprises His157 and/or Ser158. As indicated by the appended examples, the AD associated TREM2 variant p.H157Y leads to enhanced shedding of TREM2, suggesting that His157 plays a pivotal role in the regulation of TREM2 cleavage. Therefore, it is most preferred in the context of the present invention that the binding site of the herein provided binding molecule comprises His157 of TREM2, particularly of human or murine membrane bound TREM2. Accordingly, one aspect of the present invention relates to the herein provided binding molecule, wherein the binding site comprises histidine at position 157 of TREM2.

The herein provided binding molecule inhibits TREM2 cleavage by inhibiting access of the cleaving enzyme to TREM2. There are several assays known in the art that can be used in order to quantify cleavage of TREM2. These methods may be used in the context of the present invention in order to assay (i.e. quantify) inhibition of TREM2 cleavage by the herein provided binding molecule. For example, inhibition of TREM2 cleavage can be tested (particularly quantified) by using the following assays that are known in the art, and described, e.g., in Kleinberger et al. [15]:

1.) Immunoblotting of membrane fractions or protein lysates of human and/or mouse TREM2 expressing cells. Efficiency of TREM2 cleavage can be tested by analyzing higher molecular weight ("mature") bands (see, e.g., Kleinberger et al. [15] and 10).
2.) Immunoblotting of supernatants from human and/or mouse TREM2 expressing cells (see, e.g., [15], FIGS. 1B, 1C and 4B).
3.) ELISA-based quantification of soluble TREM2 in supernatants from human and/or mouse TREM2 expressing cells (see, e.g., [15], FIGS. 1B, 4C and 7A).
4.) Quantification of membrane-bound (i.e. cell surface-exposed TREM2 by a surface biotinylation assay (see, e.g., Kleinberger et al. [15], FIG. 2F).
5.) Quantification of membrane-bound (i.e. cell surface-exposed TREM2 on human and/or mouse cell lines and primary cells by flow-cytometry.
6.) Quantification of membrane-bound (i.e. cell surface-exposed TREM2 exposed on human and/or mouse cell lines and primary cells by cell-based ELISA technique.
7.) Quantification of cell surface (i.e. membrane)-exposed TREM2 on human and/or mouse cell lines and primary cells by surface immunocytochemistry (see e.g. [16])
8.) ELISA-based quantification of soluble TREM2 (sTREM2) from tissue and/or biofluids of human and/or mouse (e.g. from brain, liver, spleen, serum, plasma, cerebrospinal fluid and/or urine).
9.) Immunoblotting of TREM2 from tissue and/or biofluids from human and/or mouse origin (e.g. from brain, liver, spleen, serum, plasma, cerebrospinal fluid and/or urine).

Any one of the above described methods may be used in the context of the present invention for testing whether a particular binding molecule inhibits TREM2 cleavage. Thus, one aspect of the present invention relates to the herein provided binding molecule, wherein inhibition of TREM2 cleavage is assayed by immunoblotting, ELISA-based quantification of soluble TREM2, quantification of surface-bound TREM2 by surface biotinylation assays, quantification of surface-bound TREM2 by flow-cytometry, quantification of surface-bound TREM2 by surface immunocytochemistry and/or quantification of surface-bound TREM2 by cell-based ELISA technique The inhibition of cleavage of TREM2 by a binding molecule correlates with the amount of membrane bound TREM2. Thus, the amount of membrane bound TREM2 is increased in the presence of the binding molecule as compared to the amount of membrane bound TREM2 in the absence of the binding molecule. For example, a binding molecule may be considered as a binding molecule that inhibits cleavage of TREM2, if in the presence of said binding molecule the amount of membrane bound TREM2 is at least 110%, preferably at least 120%, more preferably at least 150%, even more preferably at least 200%, and even more preferably at least 250% of the amount of membrane bound TREM2 in the absence of the binding molecule, as assayed, e.g., by any one of the assays mentioned above, particularly by immunoblotting or flow-cytometry. In such an assay cells may be used that comprise a TREM2 cleavage enzyme.

Accordingly, a binding molecule may be considered as a binding molecule that inhibits cleavage of TREM2, if in the presence of said binding molecule the amount of membrane bound TREM2 is at least 10%, preferably at least 20%, more preferably at least 50%, even more preferably at least 100%, and even more preferably at least 150% more than the amount of membrane bound TREM2 in the absence of the binding molecule, as assayed, e.g., by any one of the assays mentioned above, particularly by immunoblotting or flow-cytometry. As mentioned, any one of the assays mentioned above, particularly immunoblotting or ELISA based quantification of sTREM2 may be used for quantifying inhibition of TREM2 cleavage of the herein provided binding molecule. In such an assay cells may be used that comprise a TREM2 cleavage enzyme.

Herein, the term "membrane bound TREM2" (also called "membrane-bound TREM2") means that the full-length TREM2 protein, including its ectodomain, is glycosylated and bound to a membrane, particularly to the plasma membrane of microglia cells.

The degree of inhibition of cleavage of TREM2 by a binding molecule negatively correlates with the amount of soluble TREM2 (sTREM2) in the presence of the binding molecule as compared to the amount of sTREM2 in the absence of the binding molecule. For example, a binding molecule may be considered as a binding molecule that inhibits cleavage of TREM2, if in the presence of said binding molecule the amount of sTREM2 is 0-90%, preferably 0-80%, more preferably 0-70%, even more preferably 0-60%, even more preferably 0-50% and even more preferable 0-20% of the amount of sTREM2 in the absence of the binding molecule, as assayed, e.g., by any one of the assays mentioned above, particularly by ELISA-based quantification of sTREM2.

The appended Examples show that the antibody clone 14D3 decreases TREM2 cleavage by about 70% while increasing the level of mature TREM2 by up to five-fold. Thus, it is preferred that, as compared to non-treated cells (i.e. cells that do not comprise the binding molecule of the invention), the binding molecule decreases TREM2 cleavage by at least 60% or most preferably by about 70%. As mentioned above, the amount of TREM2 cleavage may be assayed by ELISA, which for quantification is a more robust assay than quantification of Western Blot results.

The appended examples show that ADAM proteases cleave (i.e. shed) TREM2 at position His157. However, it has been shown in the prior art that even after administration of an inhibitor for ADAM proteases TREM2 cleavage takes place at a certain degree [15]. These data suggest that also proteases other than ADAM proteases cleave TREM2. However, cleavage (i.e. shedding) of TREM2 by any protease that cleavages TREM2 at position His157 (or at a position in close proximity to this position) may be inhibited by the herein provided binding molecule. Thus, in the context of the present invention the cleaving enzyme may be any metalloproteinase. For example, said metalloproteinase may be a disintegrin and metalloproteinase domain-containing protein (ADAM) or a matrix metalloproteinase (MMP). Thus, in one aspect of the present invention the binding molecule interferes with the binding of a cleaving enzyme to TREM2, wherein the cleaving enzyme is ADAM or a MMP. It has been described in the prior art that ADAM10 and ADAM17 are involved in TREM2 shedding [15, 16, 32]. Therefore, herein ADAM may be ADAM10 and/or ADAM17. It is prioritized in the context of the present invention that the cleavage enzyme is ADAM10.

By inhibiting TREM2 cleavage, the herein provided binding molecule preserves and/or stimulates activity of microglia cells, and/or the activity of other TREM2 expressing cells. Preferably, the herein provided binding molecule preserves and/or stimulates activity of microglia cells. Said activity of microglia cells may be phagocytosis activity, migration, calcium signaling, Syk activation, and/or proliferation. TREM2 is also regulating the inflammatory cytokine production and survival of microglia cells. Therefore, said activity of microglia cells may also be regulation of inflammatory cytokine production and/or survival. Preferably, the herein provided binding molecule preserves and/or stabilizes phagocytosis activity of microglia cells. There are several assays known in the art that can be used for measuring phagocytosis activity of cells. For example, for testing whether a given binding molecule preserves and/or stabilizes phagocytosis activity of cells, phagocytosis can be tested as described in Kleinberger et al. [15] and Xiang et al. [26]. An increase in the phagocytosis activity can be tested in vivo using methods described in [33]. For testing whether a given binding molecule preserves and/or stabilizes calcium signaling of cells several means and methods are known in the art, and described, e.g., in [20].

The herein provided binding molecule may be an antibody (such as a nanobody) or a small molecule. A "small molecule" may be of any kind including peptides, foldamers, proteomimetics and compounds derived from organic synthesis with a low molecular weight (<900 daltons). Small molecules may help to regulate a biological process, and have generally a size on the order of $10^{-10}$ m. Many drugs are small molecules.

Figure 4:
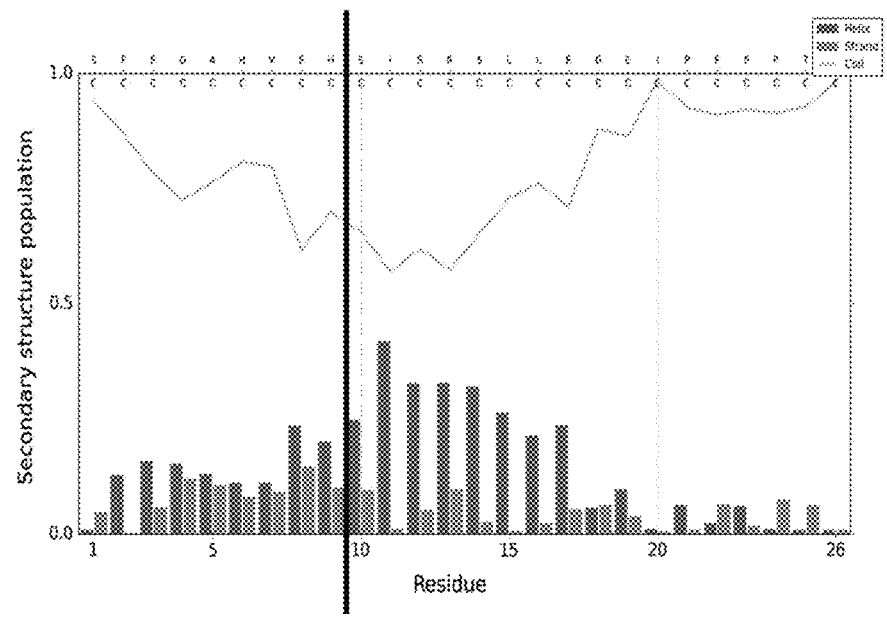

In the appended examples the secondary structure of the TREM2 stalk region is predicted. As shown in FIG. 4, the C-terminus of the TREM2 ectodomain shows largely alpha helical structures. Thus, in order to obtain a small molecule that inhibits TREM2 cleavage by metalloproteinases such as ADAMs or MMPs, small molecules inhibiting alpha-helix-mediated protein-protein interactions (TREM2-ADAM; TREM2-MMP) may be designed. Such small molecules may be designed by designing either constraint alpha-helical peptides or proteomimetics that match the topography of an alpha helix by mimicking the spatial orientation of its hot-spot residues. These approaches are known in the art and reviewed, e.g. in [34]. The designed small molecule may be produced, e.g., by organic synthesis.

"Hot spot residues" of proteins are fundamental interface residues that help proteins to perform their functions. Most of the protein-protein binding energy is related only to a group of few amino acids at intermolecular protein interfaces: the hot spots (see, e.g., Zerbe, 2012, J Chem Inf Model., 52(8): 2236-2244). In the context of protein-protein interactions, the term "hot spot" refers to a residue or cluster of residues that makes a major contribution to the binding free energy, as determined by alanine scanning mutagenesis. In contrast, in pharmaceutical research, a hot spot is a site on a target protein that has high propensity for ligand binding and hence is potentially important for drug discovery.

Thus, if the herein provided binding molecule is a small molecule, it may be a constraint alpha-helical peptide, foldamer or proteomimetic that matches the topography of an alpha helix of the stalk region of TREM2 by mimicking the spatial orientation of its hot-spot residues.

Herein, the terms "peptide", "oligopeptide", "polypeptide" and "protein" are used interchangeably and relate to a molecule that encompasses at least one amino acid chain, wherein the amino acid residues are linked by peptide (amide) bonds. The terms "peptide", "oligopeptide", "polypeptide" and "protein" also encompass molecules comprising amino acids other than the 20 gene-encoded amino acids, such as selenocysteine. Herein the terms "peptide", "oligopeptide", "polypeptide" and "protein" also include molecules with modifications, such as glycosylation, acetylation, phosphorylation, ubiquitination, sumoylation and the like. Such modifications are well described in the art.

Herein, the term "proteomimetic" refers to any compound that mimics the structure and function of a region of protein (or polypeptide, or oligopeptide, or peptide) surface.

However, as described above, the binding molecule of the present invention may also be an antibody. Preferably, the antibody is a monoclonal antibody. The antibody may also be an antibody fragment, such as a nanobody, a Fab fragment, a Fab' fragment, a Fab'-SH fragment, a F(ab')$_2$ fragment, a Fd fragment, a Fv fragment, a scFv fragment, or an isolated complementarity determining region (CDR). The antibody or antibody fragment may be a humanized antibody/antibody fragment, a fully human antibody/antibody fragment, a mouse antibody/antibody fragment, a rat antibody/antibody fragment, a rabbit antibody/antibody fragment, a hamster antibody/antibody fragment, a goat antibody/antibody fragment, a guinea pig antibody/antibody fragment, a ferret antibody/antibody fragment, a cat antibody/antibody fragment, a dog antibody/antibody fragment, a chicken antibody/antibody fragment, a sheep antibody/ antibody fragment, a bovine antibody/antibody fragment, a horse antibody/antibody fragment, a camel antibody/antibody fragment, or a monkey antibody/antibody fragment such as a primate antibody/antibody fragment. It is prioritized that the antibody is a humanized antibody/antibody fragment, a fully human antibody/antibody fragment, a mouse antibody/antibody fragment, a rat antibody/antibody fragment, a rabbit antibody/antibody fragment, a hamster antibody/antibody fragment, a goat antibody/antibody fragment, a guinea pig antibody/antibody fragment, a ferret antibody/antibody fragment, a chicken antibody/antibody fragment, a sheep antibody/antibody fragment, or a monkey antibody/antibody fragment such as a primate antibody/antibody fragment. It is even more prioritized that the antibody is a humanized antibody/antibody fragment, a fully human antibody/antibody fragment, a mouse antibody/antibody fragment, or a rat antibody/antibody fragment. Accordingly, the herein provided binding molecule may be a humanized antibody fragment, such as a humanized nanobody. The herein provided binding molecule may further be a chimeric antibody and/or a bispecific antibody.

In the appended Examples antibodies which bind to the TREM2 cleavage site (e.g. to an epitope within the peptide of SEQ ID NO: 7, such as an epitope comprising His 157 and/or Ser158) have been prepared. The appended Examples show that these antibodies decrease TREM2 cleavage. A consensus sequence of all antibodies that actively inhibit TREM2 cleavage has been designed (see FIG. 8). One aspect of the present invention relates to the binding molecule provided herein, wherein the binding molecule is an antibody that corresponds to said consensus sequence. Accordingly, the binding molecule provided herein may be an antibody, wherein the antibody is any one of the following antibodies:

(1) an antibody, wherein the heavy chain variable region comprises the sequence of SEQ ID NO: 32 and the light chain variable region comprises the sequence of SEQ ID NO: 42; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 32, and the light chain variable region comprises a sequence having at least 85%, preferably at least 90%, more preferably at least 95%, even more preferably at least 98%, and most preferably at least 99% identity to SEQ ID NO: 42; and wherein the antibody inhibits TREM2 cleavage;

(3) an antibody, wherein the CDR1 of the heavy chain variable region comprises the amino acid sequence of SEQ ID NO: 52; the CDR2 of the heavy chain variable region comprises the amino acid sequence of SEQ ID NO: 62; the CDR3 of the heavy chain variable region comprises the amino acid sequence of SEQ ID NO: 72; the CDR1 of the light chain variable region comprises the amino acid sequence of SEQ ID NO: 82; the CDR2 of the light chain variable region comprises the amino acid sequence of SEQ ID NO: 92; and the CDR3 of the light chain variable region comprises the amino acid sequence of SEQ ID NO: 102; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 52; the CDR2 of the heavy chain variable region comprises an amino acid sequence having at least 70%, preferably at least 75%, more preferably at least 80%, even more preferably at least 85%, and most preferably at least 90% identity to SEQ ID NO: 62; the CDR3 of the heavy chain variable region comprises an amino acid sequence having at least 70%, preferably at least 75%, more preferably at least 80%, even more preferably at least 85%, and most preferably at least 90% identity to SEQ ID NO: 72; the CDR1 of the light chain variable region comprises an amino acid sequence having at least 70%, preferably at least 75%, more preferably at least 80%, even more preferably at least 85%, and most preferably at least 90% identity to SEQ ID NO: 82; the CDR2 of the light chain variable region comprises an amino acid sequence having at least 60%, preferably 100% identity to SEQ ID NO: 92; and the CDR3 of the light chain variable region comprises an amino acid sequence having at least 70%, preferably at least 75%, more preferably at least 80%, and most preferably at least 85% identity to SEQ ID NO: 102; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

As demonstrated in the appended Examples, the antibody clone that shows the best activity to inhibit TREM2 cleavage is the antibody clone 14D3. Therefore, a most preferred aspect of the present invention relates to the binding molecule provided herein, wherein the binding molecule is an antibody that corresponds to the antibody clone 14D3. Accordingly, the binding molecule provided herein may be an antibody, wherein the antibody is any one of the following antibodies:

(1) an antibody, wherein the heavy chain variable region comprises the sequence of SEQ ID NO: 23 and the light chain variable region comprises the sequence of SEQ ID NO: 33; and wherein the antibody inhibits TREM2 cleavage;

(2) an antibody, wherein the heavy chain variable region comprises a sequence having at least 85% identity to SEQ ID NO: 23, and the light chain variable region comprises a sequence having at least 85% identity to SEQ ID NO: 33; and wherein the antibody inhibits TREM2 cleavage;

(3) an antibody, wherein the CDR1 of the heavy chain variable region comprises the amino acid sequence of SEQ ID NO: 43; the CDR2 of the heavy chain variable region comprises the amino acid sequence of SEQ ID NO: 53; the CDR3 of the heavy chain variable region comprises the amino acid sequence of SEQ ID NO: 63; the CDR1 of the light chain variable region comprises the amino acid sequence of SEQ ID NO: 73; the CDR2 of the light chain variable region comprises the amino acid sequence of SEQ ID NO: 83; and the CDR3 of the light chain variable region comprises the amino acid sequence of SEQ ID NO: 93; and wherein the antibody inhibits TREM2 cleavage; or (4) an antibody, wherein the CDR1 of the heavy chain variable region comprises an amino acid sequence having at least 70% identity to SEQ ID NO: 43; the CDR2 of the heavy chain variable region comprises an amino acid sequence having at least 70% identity to SEQ ID NO: 53; the CDR3 of the heavy chain variable region comprises an amino acid sequence having at least 70% identity to SEQ ID NO: 63; the CDR1 of the light chain variable region comprises an amino acid sequence having at least 70% identity to SEQ ID NO: 73; the CDR2 of the light chain variable region comprises an amino acid sequence having at least 60% identity to SEQ ID NO: 83; and the CDR3 of the light chain variable region comprises an amino acid sequence having at least 70% identity to SEQ ID NO: 93; and wherein the antibody inhibits TREM2 cleavage.

Preferably, the antibody as defined in items (2)-(4), above, has an activity to inhibit TREM2 cleavage, which is equivalent to that of the antibody as defined under item (1). The appended Examples show that antibody clone 14D3 decreases TREM2 cleavage by about 70% while increasing the level of mature TREM2 by up to five-fold. Thus, it is preferred that, as compared to non-treated cells (i.e. cells that do not comprise the antibody defined above), the antibody defined above decreases TREM2 cleavage by at least 60% or most preferably by about 70%. Also antibody fragments of the antibody described above are encompassed by the present invention.

This most preferred aspect of the present invention also relates to the binding molecule provided herein, wherein said binding molecule is an antibody, and wherein the antibody is any one of the following antibodies:

(1) an antibody, wherein the heavy chain variable region comprises a sequence having at least 85%, preferably at least 90%, more preferably at least 95%, even more preferably at least 98%, and most preferably at least 99% identity to SEQ ID NO: 23, and the light chain variable region comprises a sequence having at least 85%, preferably at least 90%, more preferably at least 95%, even more preferably at least 98%, and most preferably at least 99% identity to SEQ ID NO: 33; and wherein the antibody inhibits TREM2 cleavage;

(2) an antibody, wherein the CDR1 of the heavy chain variable region comprises an amino acid sequence having at least 70%, preferably at least 75%, more preferably at least 80%, and most preferably at least 85% identity to SEQ ID NO: 43; the CDR2 of the heavy chain variable region comprises an amino acid sequence having at least 70%, preferably at least 75%, more preferably at least 80%, even more preferably at least 85%, and most preferably at least 90% identity to SEQ ID NO: 53; the CDR3 of the heavy chain variable region comprises an amino acid sequence having at least 70%, preferably at least 75%, more preferably at least 80%, even more preferably at least 85%, and most preferably at least 90% identity to SEQ ID NO: 63; the CDR1 of the light chain variable region comprises an amino acid sequence having at least 70%, preferably at least 75%, more preferably at least 80%, even more preferably at least 85%, and most preferably at least 90% identity to SEQ ID NO: 73; the CDR2 of the light chain variable region comprises an amino acid sequence having at least 60%, preferably 100% identity to SEQ ID NO: 83; and the CDR3 of the light chain variable region comprises an amino acid sequence having at least 70%, preferably at least 75%, more preferably at least 80%, and most preferably at least 85% identity to SEQ ID NO: 93; and wherein the antibody inhibits TREM2 cleavage.

Preferably, the antibody as defined in items (1) and (2), above, has an activity to inhibit TREM2 cleavage, which is equivalent to that of an antibody which has a heavy chain variable region comprising the sequence of SEQ ID NO: 23 and a light chain variable region comprising the sequence of SEQ ID NO: 33. It is preferred that, as compared to non-treated cells (i.e. cells that do not comprise the antibody defined above), the antibody defined above decreases TREM2 cleavage by at least 60% or most preferably by about 70%. Also antibody fragments of the antibody described above are encompassed by the present invention.

The appended Examples show that the antibody clone 14D8 has very high activity to inhibit TREM2 cleavage. Therefore, a particularly preferred aspect of the present invention relates to the binding molecule provided herein, wherein the binding molecule is an antibody that corresponds to the antibody clone 14D8. Accordingly, the binding molecule provided herein may be an antibody, wherein the antibody is any one of the following antibodies:

(1) an antibody, wherein the heavy chain variable region comprises the sequence of SEQ ID NO: 24 and the light chain variable region comprises the sequence of SEQ ID NO: 34; and wherein the antibody inhibits TREM2 cleavage;

(2) an antibody, wherein the heavy chain variable region comprises a sequence having at least 85% identity to SEQ ID NO: 24, and the light chain variable region comprises a sequence having at least 85% identity to SEQ ID NO: 34; and wherein the antibody inhibits TREM2 cleavage;

(3) an antibody, wherein the CDR1 of the heavy chain variable region comprises the amino acid sequence of SEQ ID NO: 44; the CDR2 of the heavy chain variable region comprises the amino acid sequence of SEQ ID NO: 54; the CDR3 of the heavy chain variable region comprises the amino acid sequence of SEQ ID NO: 64; the CDR1 of the light chain variable region comprises the amino acid sequence of SEQ ID NO: 74; the CDR2 of the light chain variable region comprises the amino acid sequence of SEQ ID NO: 84; and the CDR3 of the light chain variable region comprises the amino acid sequence of SEQ ID NO: 94; and wherein the antibody inhibits TREM2 cleavage; or (4) an antibody, wherein the CDR1 of the heavy chain variable region comprises an amino acid sequence having at least 70% identity to SEQ ID NO: 44; the CDR2 of the heavy chain variable region comprises an amino acid sequence having at least 70% identity to SEQ ID NO: 54; the CDR3 of the heavy chain variable region comprises an amino acid sequence having at least 70% identity to SEQ ID NO: 64; the CDR1 of the light chain variable region comprises an amino acid sequence having at least 70% identity to SEQ ID NO: 74; the CDR2 of the light chain variable region comprises an amino acid sequence having at least 60% identity to SEQ ID NO: 84; and the CDR3 of the light chain variable region comprises an amino acid sequence having at least 70% identity to SEQ ID NO: 94; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

This particularly preferred aspect of the present invention also relates to the binding molecule provided herein, wherein said binding molecule is an antibody, and wherein the antibody is any one of the following antibodies:

(1) an antibody, wherein the heavy chain variable region comprises a sequence having at least 85%, preferably at least 90%, more preferably at least 95%, even more preferably at least 98%, and most preferably at least 99% identity to SEQ ID NO: 24, and the light chain variable region comprises a sequence having at least 85%, preferably at least 90%, more preferably at least 95%, even more preferred at least 98%, and most preferably at least 99% identity to SEQ ID NO: 34; and wherein the antibody inhibits TREM2 cleavage;

(2) an antibody, wherein the CDR1 of the heavy chain variable region comprises an amino acid sequence having at least 70%, preferably at least 75%, more preferably at least 80%, and most preferably at least 85% identity to SEQ ID NO: 44; the CDR2 of the heavy chain variable region comprises an amino acid sequence having at least 70%, preferably at least 75%, more preferably at least 80%, even more preferably at least 85%, and most preferably at least 90% identity to SEQ ID NO: 54; the CDR3 of the heavy chain variable region comprises an amino acid sequence having at least 70%, preferably at least 75%, more preferably at least 80%, even more preferably at least 85%, and most preferably at least 90% identity to SEQ ID NO: 64; the CDR1 of the light chain variable region comprises an amino acid sequence having at least 70%, preferably at least 75%, more preferably at least 80%, even more preferably at least 85%, and most preferably at least 90% identity to SEQ ID NO: 74; the CDR2 of the light chain variable region comprises an amino acid sequence having at least 60%, preferably 100% identity to SEQ ID NO: 84; and the CDR3 of the light chain variable region comprises an amino acid sequence having at least 70%, preferably at least 75%, more preferably at least 80%, and most preferably at least 85% identity to SEQ ID NO: 94; and wherein the antibody inhibits TREM2 cleavage.

Preferably, the antibody as defined in items (1) and (2), above, has an activity to inhibit TREM2 cleavage, which is equivalent to that of an antibody which has a heavy chain variable region comprising the sequence of SEQ ID NO: 24 and a light chain variable region comprising the sequence of SEQ ID NO: 34. Also antibody fragments of the antibody described above are encompassed by the present invention.

One aspect of the present invention relates to the binding molecule provided herein, wherein the binding molecule is an antibody that corresponds to the antibody clone 7A12. Accordingly, the binding molecule provided herein may be an antibody, wherein the antibody is any one of the following antibodies:

(1) an antibody, wherein the heavy chain variable region comprises the sequence of SEQ ID NO: 25 and the light chain variable region comprises the sequence of SEQ ID NO: 35; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 25, and the light chain variable region comprises a sequence having at least 85%, preferably at least 90%, more preferably at least 95%, even more preferably at least 98%, and most preferably at least 99% identity to SEQ ID NO: 35; and wherein the antibody inhibits TREM2 cleavage;

(3) an antibody, wherein the CDR1 of the heavy chain variable region comprises the amino acid sequence of SEQ ID NO: 45; the CDR2 of the heavy chain variable region comprises the amino acid sequence of SEQ ID NO: 55; the CDR3 of the heavy chain variable region comprises the amino acid sequence of SEQ ID NO: 65; the CDR1 of the light chain variable region comprises the amino acid sequence of SEQ ID NO: 75; the CDR2 of the light chain variable region comprises the amino acid sequence of SEQ ID NO: 85; and the CDR3 of the light chain variable region comprises the amino acid sequence of SEQ ID NO: 95; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 45; the CDR2 of the heavy chain variable region comprises an amino acid sequence having at least 70%, preferably at least 75%, more preferably at least 80%, even more preferably at least 85%, and most preferably at least 90% identity to SEQ ID NO: 55; the CDR3 of the heavy chain variable region comprises an amino acid sequence having at least 70%, preferably at least 75%, more preferably at least 80%, even more preferably at least 85%, and most preferably at least 90% identity to SEQ ID NO: 65; the CDR1 of the light chain variable region comprises an amino acid sequence having at least 70%, preferably at least 75%, more preferably at least 80%, even more preferably at least 85%, and most preferably at least 90% identity to SEQ ID NO: 75; the CDR2 of the light chain variable region comprises an amino acid sequence having at least 60%, preferably 100% identity to SEQ ID NO: 85; and the CDR3 of the light chain variable region comprises an amino acid sequence having at least 70%, preferably at least 75%, more preferably at least 80%, and most preferably at least 85% identity to SEQ ID NO: 95; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

One aspect of the present invention relates to the binding molecule provided herein, wherein the binding molecule is an antibody that corresponds to the antibody clone 8A11. Accordingly, the binding molecule provided herein may be an antibody, wherein the antibody is any one of the following antibodies:

(1) an antibody, wherein the heavy chain variable region comprises the sequence of SEQ ID NO: 26 and the light chain variable region comprises the sequence of SEQ ID NO: 36; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 26, and the light chain variable region comprises a sequence having at least 85%, preferably at least 90%, more preferably at least 95%, even more preferably at least 98%, and most preferably at least 99% identity to SEQ ID NO: 36; and wherein the antibody inhibits TREM2 cleavage;

(3) an antibody, wherein the CDR1 of the heavy chain variable region comprises the amino acid sequence of SEQ ID NO: 46; the CDR2 of the heavy chain variable region comprises the amino acid sequence of SEQ ID NO: 56; the CDR3 of the heavy chain variable region comprises the amino acid sequence of SEQ ID NO: 66; the CDR1 of the light chain variable region comprises the amino acid sequence of SEQ ID NO: 76; the CDR2 of the light chain variable region comprises the amino acid sequence of SEQ ID NO: 86; and the CDR3 of the light chain variable region comprises the amino acid sequence of SEQ ID NO: 96; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 46; the CDR2 of the heavy chain variable region comprises an amino acid sequence having at least 70%, preferably at least 75%, more preferably at least 80%, even more preferably at least 85%, and most preferably at least 90% identity to SEQ ID NO: 56; the CDR3 of the heavy chain variable region comprises an amino acid sequence having at least 70%, preferably at least 75%, more preferably at least 80%, even more preferably at least 85%, and most preferably at least 90% identity to SEQ ID NO: 66; the CDR1 of the light chain variable region comprises an amino acid sequence having at least 70%, preferably at least 75%, more preferably at least 80%, even more preferably at least 85%, and most preferably at least 90% identity to SEQ ID NO: 76; the CDR2 of the light chain variable region comprises an amino acid sequence having at least 60%, preferably 100% identity to SEQ ID NO: 86; and the CDR3 of the light chain variable region comprises an amino acid sequence having at least 70%, preferably at least 75%, more preferably at least 80%, and most preferably at least 85% identity to SEQ ID NO: 96; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

One aspect of the present invention relates to the binding molecule provided herein, wherein the binding molecule is an antibody that corresponds to the antibody clone 21A3. Accordingly, the binding molecule provided herein may be an antibody, wherein the antibody is any one of the following antibodies:

(1) an antibody, wherein the heavy chain variable region comprises the sequence of SEQ ID NO: 27 and the light chain variable region comprises the sequence of SEQ ID NO: 37; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 27, and the light chain variable region comprises a sequence having at least 85%, preferably at least 90%, more preferably at least 95%, even more preferably at least 98%, and most preferably at least 99% identity to SEQ ID NO: 37; and wherein the antibody inhibits TREM2 cleavage;

(3) an antibody, wherein the CDR1 of the heavy chain variable region comprises the amino acid sequence of SEQ ID NO: 47; the CDR2 of the heavy chain variable region comprises the amino acid sequence of SEQ ID NO: 57; the CDR3 of the heavy chain variable region comprises the amino acid sequence of SEQ ID NO: 67; the CDR1 of the light chain variable region comprises the amino acid sequence of SEQ ID NO: 77; the CDR2 of the light chain variable region comprises the amino acid sequence of SEQ ID NO: 87; and the CDR3 of the light chain variable region comprises the amino acid sequence of SEQ ID NO: 97; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 47; the CDR2 of the heavy chain variable region comprises an amino acid sequence having at least 70%, preferably at least 75%, more preferably at least 80%, even more preferably at least 85%, and most preferably at least 90% identity to SEQ ID NO: 57; the CDR3 of the heavy chain variable region comprises an amino acid sequence having at least 70%, preferably at least 75%, more preferably at least 80%, even more preferably at least 85%, and most preferably at least 90% identity to SEQ ID NO: 67; the CDR1 of the light chain variable region comprises an amino acid sequence having at least 70%, preferably at least 75%, more preferably at least 80%, even more preferably at least 85%, and most preferably at least 90% identity to SEQ ID NO: 77; the CDR2 of the light chain variable region comprises an amino acid sequence having at least 60%, preferably 100% identity to SEQ ID NO: 87; and the CDR3 of the light chain variable region comprises an amino acid sequence having at least 70%, preferably at least 75%, more preferably at least 80%, and most preferably at least 85% identity to SEQ ID NO: 97; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

One aspect of the present invention relates to the binding molecule provided herein, wherein the binding molecule is an antibody that corresponds to the antibody clone 10C3. Accordingly, the binding molecule provided herein may be an antibody, wherein the antibody is any one of the following antibodies:

(1) an antibody, wherein the heavy chain variable region comprises the sequence of SEQ ID NO: 28 and the light chain variable region comprises the sequence of SEQ ID NO: 38; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 28, and the light chain variable region comprises a sequence having at least 85%, preferably at least 90%, more preferably at least 95%, even more preferably at least 98%, and most preferably at least 99% identity to SEQ ID NO: 38; and wherein the antibody inhibits TREM2 cleavage;

(3) an antibody, wherein the CDR1 of the heavy chain variable region comprises the amino acid sequence of SEQ ID NO: 48; the CDR2 of the heavy chain variable region comprises the amino acid sequence of SEQ ID NO: 58; the CDR3 of the heavy chain variable region comprises the amino acid sequence of SEQ ID NO: 68; the CDR1 of the light chain variable region comprises the amino acid sequence of SEQ ID NO: 78; the CDR2 of the light chain variable region comprises the amino acid sequence of SEQ ID NO: 88; and the CDR3 of the light chain variable region comprises the amino acid sequence of SEQ ID NO: 98; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 48; the CDR2 of the heavy chain variable region comprises an amino acid sequence having at least 70%, preferably at least 75%, more preferably at least 80%, even more preferably at least 85%, and most preferably at least 90% identity to SEQ ID NO: 58; the CDR3 of the heavy chain variable region comprises an amino acid sequence having at least 70%, preferably at least 75%, more preferably at least 80%, even more preferably at least 85%, and most preferably at least 90% identity to SEQ ID NO: 68; the CDR1 of the light chain variable region comprises an amino acid sequence having at least 70%, preferably at least 75%, more preferably at least 80%, even more preferably at least 85%, and most preferably at least 90% identity to SEQ ID NO: 78; the CDR2 of the light chain variable region comprises an amino acid sequence having at least 60%, preferably 100% identity to SEQ ID NO: 88; and the CDR3 of the light chain variable region comprises an amino acid sequence having at least 70%, preferably at least 75%, more preferably at least 80%, and most preferably at least 85% identity to SEQ ID NO: 98; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

One aspect of the present invention relates to the binding molecule provided herein, wherein the binding molecule is an antibody that corresponds to the antibody clone 18F9. Accordingly, the binding molecule provided herein may be an antibody, wherein the antibody is any one of the following antibodies:

(1) an antibody, wherein the heavy chain variable region comprises the sequence of SEQ ID NO: 29 and the light chain variable region comprises the sequence of SEQ ID NO: 39; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferred at least 99% identity to SEQ ID NO: 29, and the light chain variable region comprises a sequence having at least 85%, preferably at least 90%, more preferably at least 95%, even more preferably at least 98%, and most preferably at least 99% identity to SEQ ID NO: 39; and wherein the antibody inhibits TREM2 cleavage;

(3) an antibody, wherein the CDR1 of the heavy chain variable region comprises the amino acid sequence of SEQ ID NO: 49; the CDR2 of the heavy chain variable region comprises the amino acid sequence of SEQ ID NO: 59; the CDR3 of the heavy chain variable region comprises the amino acid sequence of SEQ ID NO: 69; the CDR1 of the light chain variable region comprises the amino acid sequence of SEQ ID NO: 79; the CDR2 of the light chain variable region comprises the amino acid sequence of SEQ ID NO: 89; and the CDR3 of the light chain variable region comprises the amino acid sequence of SEQ ID NO: 99; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 49; the CDR2 of the heavy chain variable region comprises an amino acid sequence having at least 70%, preferably at least 75%, more preferably at least 80%, even more preferably at least 85%, and most preferably at least 90% identity to SEQ ID NO: 59; the CDR3 of the heavy chain variable region comprises an amino acid sequence having at least 70%, preferably at least 75%, more preferably at least 80%, even more preferably at least 85%, and most preferably at least 90% identity to SEQ ID NO: 69; the CDR1 of the light chain variable region comprises an amino acid sequence having at least 70%, preferably at least 75%, more preferably at least 80%, even more preferably at least 85%, and most preferably at least 90% identity to SEQ ID NO: 79; the CDR2 of the light chain variable region comprises an amino acid sequence having at least 60%, preferably 100% identity to SEQ ID NO: 89; and the CDR3 of the light chain variable region comprises an amino acid sequence having at least 70%, preferably at least 75%, more preferably at least 80%, and most preferably at least 85% identity to SEQ ID NO: 99; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

One aspect of the present invention relates to the binding molecule provided herein, wherein the binding molecule is an antibody that corresponds to the antibody clone 15C5. Accordingly, the binding molecule provided herein may be an antibody, wherein the antibody is any one of the following antibodies:

(1) an antibody, wherein the heavy chain variable region comprises the sequence of SEQ ID NO: 30 and the light chain variable region comprises the sequence of SEQ ID NO: 40; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 30, and the light chain variable region comprises a sequence having at least 85%, preferably at least 90%, more preferably at least 95%, even more preferably at least 98%, and most preferably at least 99% identity to SEQ ID NO: 40; and wherein the antibody inhibits TREM2 cleavage;

(3) an antibody, wherein the CDR1 of the heavy chain variable region comprises the amino acid sequence of SEQ ID NO: 50; the CDR2 of the heavy chain variable region comprises the amino acid sequence of SEQ ID NO: 60; the CDR3 of the heavy chain variable region comprises the amino acid sequence of SEQ ID NO: 70; the CDR1 of the light chain variable region comprises the amino acid sequence of SEQ ID NO: 80; the CDR2 of the light chain variable region comprises the amino acid sequence of SEQ ID NO: 90; and the CDR3 of the light chain variable region comprises the amino acid sequence of SEQ ID NO: 100; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 50; the CDR2 of the heavy chain variable region comprises an amino acid sequence having at least 70%, preferably at least 75%, more preferably at least 80%, even more preferably at least 85%, and most preferably at least 90% identity to SEQ ID NO: 60; the CDR3 of the heavy chain variable region comprises an amino acid sequence having at least 70%, preferably at least 75%, more preferably at least 80%, even more preferably at least 85%, and most preferably at least 90% identity to SEQ ID NO: 70; the CDR1 of the light chain variable region comprises an amino acid sequence having at least 70%, preferably at least 75%, more preferably at least 80%, even more preferably at least 85%, and most preferably at least 90% identity to SEQ ID NO: 80; the CDR2 of the light chain variable region comprises an amino acid sequence having at least 60%, preferably 100% identity to SEQ ID NO: 90; and the CDR3 of the light chain variable region comprises an amino acid sequence having at least 70%, preferably at least 75%, more preferably at least 80%, and most preferably at least 85% identity to SEQ ID NO: 100; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

One aspect of the present invention relates to the binding molecule provided herein, wherein the binding molecule is an antibody that corresponds to the antibody clone 1G6. Accordingly, the binding molecule provided herein may be an antibody, wherein the antibody is any one of the following antibodies:

(1) an antibody, wherein the heavy chain variable region comprises the sequence of SEQ ID NO: 31 and the light chain variable region comprises the sequence of SEQ ID NO: 41; and wherein the antibody inhibits TREM2 cleavage;

(2) an antibody, wherein the heavy chain variable region comprises a sequence having at least 85%, preferably at least 90%, more preferably at least 95%, even more preferably at least 98%, and most preferably at least 99% identity to SEQ ID NO: 31, and the light chain variable region comprises a sequence having at least 85%, preferably at least 90%, more preferably at least 95%, even more preferably at least 98%, and most preferably at least 99% identity to SEQ ID NO: 41; and wherein the antibody inhibits TREM2 cleavage;

(3) an antibody, wherein the CDR1 of the heavy chain variable region comprises the amino acid sequence of SEQ ID NO: 51; the CDR2 of the heavy chain variable region comprises the amino acid sequence of SEQ ID NO: 61; the CDR3 of the heavy chain variable region comprises the amino acid sequence of SEQ ID NO: 71; the CDR1 of the light chain variable region comprises the amino acid sequence of SEQ ID NO: 81; the CDR2 of the light chain variable region comprises the amino acid sequence of SEQ ID NO: 91; and the CDR3 of the light chain variable region comprises the amino acid sequence of SEQ ID NO: 101; and wherein the antibody inhibits TREM2 cleavage; or (4) an antibody, wherein the CDR1 of the heavy chain variable region comprises an amino acid sequence having at least 70%, preferably at least 75%, more preferably at least 80%, and most preferably at least 85% identity to SEQ ID NO: 51; the CDR2 of the heavy chain variable region comprises an amino acid sequence having at least 70%, preferably at least 75%, more preferably at least 80%, even more preferably at least 85%, and most preferably at least 90% identity to SEQ ID NO: 61; the CDR3 of the heavy chain variable region comprises an amino acid sequence having at least 70%, preferably at least 75%, more preferably at least 80%, even more preferably at least 85%, and most preferably at least 90% identity to SEQ ID NO: 71; the CDR1 of the light chain variable region comprises an amino acid sequence having at least 70%, preferably at least 75%, more preferably at least 80%, even more preferably at least 85%, and most preferably at least 90% identity to SEQ ID NO: 81; the CDR2 of the light chain variable region comprises an amino acid sequence having at least 60%, preferably 100% identity to SEQ ID NO: 91; and the CDR3 of the light chain variable region comprises an amino acid sequence having at least 70%, preferably at least 75%, more preferably at least 80%, and most preferably at least 85% identity to SEQ ID NO: 101; and wherein the antibody inhibits TREM2 cleavage.

Preferably, the antibody as defined in items (2)-(4), above, has an activity to inhibit TREM2 cleavage, which is equivalent to that of the antibody as defined under item (1). Also antibody fragments of the antibody described above are encompassed by the present invention.

In accordance with the present invention, CDR determination may be performed according to IMGT criteria (Ehrenmann et al., Chapter 2, R. Kontermann and S. Dübel (eds.), Antibody Engineering Vol. 2, Springer-Verlag Berlin Heidelberg 2010).

Several techniques for the production of target site-specific antibodies (i.e. antibodies that bind to a particular binding site) are commonly known in the art. For example, an antibody that specifically binds to a particular binding site within the ectodomain of TREM2 may be produced by immunization of mice or rats with the peptides comprising the desired binding site within the ectodomain or TREM2. For example, any one of the peptides as shown in SEQ ID NOs: 7-15, 21 and 22 may be used for immunization. More specifically, for generating an antibody against human TREM2 that may be used in the context of the present invention, a peptide as shown in SEQ ID NO: 7 (AHVEHSISRS), SEQ ID NO: 8 (EDAHVEH), SEQ ID NO: 9 (SISRSL) and/or SEQ ID NO: 21 (GESESFEDAHV) may be used for immunization Most preferably, a peptide as shown in SEQ ID NO: 7 is used. For generating an antibody against murine TREM2, a peptide as shown in SEQ ID NO: 10 (AQVEHSTSRN), SEQ ID NO: 11 (EGAQVEH), SEQ ID NO: 12 (STSRNQ) and/or SEQ ID NO: 22 (EHSTSRNQETSFP) may be used for immunization. For generation an antibody against rat TREM2, a peptide as shown in SEQ ID NO: 13 (AQVEHSTSSQ), SEQ ID NO: 14 (EGAQVEH) or SEQ ID NO: 15 (STSSQV) may be used for immunization. There are several facilities available that perform such immunization for the production of antibodies.

After production of antibodies by immunization of animals as described above, epitope mapping may be performed. Epitope mapping is the process of experimentally identifying the binding site (i.e. epitope) of an antibody on its target antigen. Several methods for epitope mapping are known in the art.

For example, in the context of the present invention epitope mapping may be performed by ELISA. Therefore, truncated versions of the TREM2 ectodomain (e.g. a truncated version of the stalk region) may be expressed in cultured cells and detected by the antibodies/nanobodies to be tested by using ELISA (see, e.g. [15]).

In addition or alternatively, epitope mapping may be performed by Immunoblotting. Therefore, truncated versions of the TREM2 ectodomain (e.g. a truncated version of the stalk region) may be expressed in cultured cells and detected by the antibodies/nanobodies to be tested using immunoblotting. In addition, deletion constructs of TREM2 (e.g. stalk region deletions) may be analyzed by immunoblotting.

In addition or alternatively, epitope mapping may be performed by Flow-cytometry. Therefore, detection of the antibodies/nanobodies to be tested that bind to TREM2 on the cell surface may be evaluated by flow-cytometry. By using this method, epitope mapping can be done by using TREM2 deletion constructs (e.g. constructs having a sequentially deletion of the stalk region) or TREM2 mutants.

In addition, several methods for epitope mapping that may be applied in the context of the present invention are summarized in Reineke and Schutkowski (eds.), Methods of Molecular Biology, Epitope Mapping Protocols, vol. 524, 2008, Humana Press. For example, epitope mapping may also be performed by protein sequence-derived scans of overlapping peptides (peptide scan); truncation analysis used to identify the minimal peptide length required for antibody binding; complete substitutional analyses to identify the key residues important for antibody binding; and/or expression of sequentially C-terminal truncated soluble TREM2.

In order to identify a binding molecule that is in accordance with the present invention, target engagement may be performed. Target engagement is the verification that a given compound interacts in vivo with the desired target and results in a desired consequence (e.g. reduction of a biomarker such as sTREM2). Thus, target engagement may be performed in order to verify that a given binding molecule (e.g. an antibody that is produced as described above) inhibits TREM2 cleavage in vivo most preferably in the target tissue which in this case might be the central nervous system. Several means and methods exist that may be used in order to realize target engagement.

For example, in the context of the present invention target engagement may be performed by evaluating the level of soluble TREM2 in tissue and/or body fluids (e.g. in blood, serum, plasma, CSF, and/or urine). Therefore, tissue and/or body fluids of human, mouse or both, human and mouse, may be used. The level of soluble TREM2 may be evaluated by using ELISA, e.g. as described in [15] and [17].

In addition or alternatively, target engagement may be performed by evaluating TREM2 maturation in tissue samples (e.g. of blood, brain, liver, and/or spleen). Therefore, tissue samples of human, mouse or both may be used. TREM2 maturation may be evaluated by using immunoprecipitation and/or immunoblotting.

In addition or alternatively, target engagement may be performed by flow cytometry evaluating whether the binding molecule to be tested increases surface expression of TREM2, as compared to control cells that are not exposed to the binding molecule.

Thus, target engagement of a given binding molecule is demonstrated if in the presence of said binding molecule the amount of soluble TREM2 is reduced in (a) body fluid(s) as compared to (a) control body fluid(s) that is not exposed to the binding molecule; see, e.g. the methods described in [15]. In addition or alternatively, target engagement of a given binding molecule is demonstrated if in the presence of said binding molecule the amount of mature TREM2 is increased in (a) tissue(s) as compared to (a) control tissue(s) that is not exposed to the binding molecule; see, e.g. the methods described in [15].

Herein, the term "TREM2" refers to a polypeptide comprising or consisting of
(i) the amino acid sequence of any one of SEQ ID NOs: 1-6; or
(ii) an amino acid sequence having at least 80%, preferably at least 90%, more preferably at least 95%, even more preferably at least 98%, and even more preferably at least 99% identity to an amino acid sequence of (i), wherein the polypeptide has the activity to induce phagocytosis, migration, and/or survival of microglia cells.

The herein provided binding molecule inhibits cleavage of membrane bound TREM2. Therefore, one aspect of the present invention relates to the herein provided binding molecule, wherein TREM2 is a polypeptide comprising or consisting of
(i) the amino acid sequence of SEQ ID NO: 1 or 4; or
(ii) an amino acid sequence having at least 80%, preferably at least 90%, more preferably at least 95%, even more preferably at least 98%, and even more preferably at least 99% identity to an amino acid sequence of (i), wherein the polypeptide has the activity to promote (proper) phagocytosis, migration, proliferation and/or survival of microglia cells.

Preferably, the binding molecule has the activity to promote (proper) phagocytosis of microglia cells. Methods for analyzing whether a given binding molecule promotes (proper) phagocytosis activity of cells are known in the art, and described, e.g., in [15].

Herein the term "ectodomain of TREM2" refers to a polypeptide comprising or consisting of
(i) the amino acid sequence of SEQ ID NO: 17 or 18; or
(ii) an amino acid sequence having at least 80%, preferably at least 90%, more preferably at least 95%, even more preferably at least 98%, and even more preferably at least 99% identity to an amino acid sequence of (i), wherein when combined with the intracellular domain of TREM2 the polypeptide has the activity to promote (proper) phagocytosis, migration, and/or survival of microglia cells. Preferably, the activity is promotion of (proper) phagocytosis of microglia cells.

His157 is located in the so-called stalk region of the ectodomain/extracellular domain of TREM2. Therefore, it is envisaged in the context of the present invention that the binding site of the herein provided binding molecule is within the stalk region of TREM2. As known in the art, the stalk region of TREM2 is the region between the Ig-like domain and the transmembrane domain.

Herein the term "intracellular domain of TREM2" refers to a polypeptide comprising or consisting of
(i) the amino acid sequence of SEQ ID NO: 19 or 20; or
(ii) an amino acid sequence having at least 80%, preferably at least 90%, more preferably at least 95%, even more preferably at least 98%, and even more preferably at least 99% identity to an amino acid sequence of (i), wherein when combined with the ectodomain of TREM2 the polypeptide has the activity to promote (proper) phagocytosis, migration, proliferation and/or survival of microglia cells. Preferably, the activity is promotion of (proper) phagocytosis of microglia cells.

As described above, the herein provided binding molecule is suitable for the treatment and/or prevention (preferably treatment) of a neurological disorder such as a neurodegenerative disorder. Thus, one aspect of the present invention relates to the herein provided binding molecule for use in treating and/or preventing a neurological disorder. Also encompassed by the present invention is a pharmaceutical composition for use in treating and/or preventing a neurological disorder, wherein the pharmaceutical composition comprises
(i) the binding molecule of the present invention; and
(ii) optionally a pharmaceutically acceptable carrier.

Thus, the present invention provides a method for treating and/or preventing a neurological disorder, wherein the method comprises administering an effective amount of the herein provided binding molecule to a subject in need of such a treatment.

In order to guarantee that the herein provided binding molecule or the herein provided pharmaceutical composition is effective in the brain, several means and methods known in the art may be applied. For example, the herein provided binding molecule or the herein provided pharmaceutical composition may be infused into the central nervous system (e.g. into the brain) by using an osmotic pump, e.g. an ALZET® Osmotic Pumps (see http://www.alzet.com/research_applications/AB.html). In addition or alternatively, the binding molecule of the present invention (e.g. the antibody, nanobody or small molecule of the present invention) may be modified in order to pass the blood-brain barrier. Modifications that are suitable in this regard include receptor-mediated transcytosis (transferrin); transporter-mediated delivery; viral-mediated delivery; nanoparticle-based delivery; liposomal delivery; the generation of bispecific antibodies; or the generation of nanobodies with a high isoelectric point (pi) that spontaneously crosses the blood-brain barrier [35]).

Pathogenesis of several neurodegenerative disorders, such as AD, is believed to be triggered by the accumulation of the amyloid-beta peptide (A-beta), which is due to overproduction of A-beta and/or the failure of clearance mechanisms, e.g. by microglia cells. A-beta self-aggregates into oligomers, which can be of various sizes, and form diffuse and neuritic plaques (i.e. amyloid plaques) in the brain parenchyma and blood vessels. A-beta oligomers and plaques are potent synaptotoxins, block proteasome function, inhibit mitochondrial activity, alter intracellular $Ca^{2+}$ levels and stimulate inflammatory processes. A-beta interacts with the signaling pathways that regulate the phosphorylation of the microtubule-associated protein tau. Hyperphosphorylation of tau disrupts its normal function in regulating axonal transport and leads to the accumulation of neurofibrillary tangles and toxic species of soluble tau. Furthermore, degradation of hyperphosphorylated tau by the proteasome is inhibited by the actions of A-beta. Thus, activating the function of microglia cells as with the herein provided binding molecules represents a strategy for treating and/or preventing neurological disorders with an inflammatory component; as well as disorders that are associated with the accumulation of amyloid plaques and/or hyperphosphorylation of tau.

Thus, the neurological disorder that may be treated and/or prevented with the herein provided binding molecule, pharmaceutical composition, or therapeutic method may be a neurological disorder with an inflammatory component. The neurological disorder that may be treated and/or prevented with the herein provided binding molecule, pharmaceutical composition, or therapeutic method is preferably a neurodegenerative disorder. Said neurodegenerative disorder may be characterized by an impaired function of microglia cells. Said neurodegenerative disorder may also be characterized by the accumulation of amyloid plaques and/or hyperphosphorylated of tau. For example, the neurodegenerative disorder to be treated and/or prevented with the herein provided binding molecule, pharmaceutical composition, or therapeutic method may be Alzheimer's disease (AD), Frontotemporal lobar degeneration (FTLD), FTLD-like syndrome, Parkinson's disease, Nasu-Hakola disease, Multiple sclerosis (MS), Huntington disease, immune-mediated neuropathies, or Amyotrophic lateral sclerosis (ALS). The neurodegenerative disorder that may be treated and/or prevented using the herein provided binding molecule, pharmaceutical composition, or therapeutic method may also be Guillain-Barré syndrome, chronic inflammatory demyelinating polyneuropathies, or Charcot-Marie-Tooth. Preferably, AD is treated and/or prevented by the herein provided means and methods.

The herein provided binding molecule or pharmaceutical composition may also be administered in the form of a co-therapy. Thus, one aspect of the present invention relates to the herein provided binding molecule, pharmaceutical composition, or therapeutic method, wherein the treatment and/or prevention is a co-therapy, wherein said binding molecule or said pharmaceutical composition is to be administered simultaneously or sequentially with another active agent. The other active agent is preferably a medicament that is used in order to treat and/or prevent a neurological disorder such as a neurodegenerative disorder. For example, said other active agent may be an acetylcholinesterase inhibitor, a N-Methyl-D-aspartate receptor (NMDAR) antagonist or immunotherapeutic (i.e. antibody).

Several acetylcholinesterase inhibitors that have been shown have a certain effect on neurodegenerative disorders such as AD are known in the art and include tacrine, rivastigmine, galantamine and donepezil. A NMDAR antagonist that has been used in therapy of neurodegenerative disorders is memantine. However, it is prioritized hat the herein provided binding molecule or pharmaceutical composition is used in a co-therapy with immunotherapy. Said immunotherapy may be A-beta immunotherapy. For example, said A-beta immunotherapy may comprise antibodies that are specific for the amyloid-beta peptide. There are numerous drugs for amyloid-related immunotherapy in clinical trials, e.g. AAB-003, ACI-24, AN-1792, Aducanumab, Affitope AD02, BAN2401, Bapineuzumab, CAD106, Crenezumab, GSK933776, Gammagrad®, Gamunex, Gantenerumab, LY3002813, MED11814, Octagam®10%, Ponezumab, SAR228810, Solanezumab, or Vanutide cridificar.

In one aspect of the present invention a neurological (e.g. neurodegenerative) disorder is treated and/or prevented in a patient, whose cerebrospinal fluid (CSF) has an increased level of soluble TREM2 (sTREM2), total-tau, and/or phospho-tau as compared to the CSF of a healthy control person. In addition or alternatively, a neurological (e.g. neurodegenerative) disorder may be treated and/or prevented in a patient, whose serum has an increased level of soluble TREM2 (sTREM2), total-tau, and/or phospho-tau as compared to the serum of a healthy control person. Thus, a neurological (e.g. neurodegenerative) disorder may be treated and/or prevented in a patient, whose serum and/or CSF has an increased level of soluble TREM2 (sTREM2), as compared to the serum and/or CSF, respectively of a healthy control person. As described above, TREM2 and tau changes during the course of neurological disorders are commonly known in the art, and described, e.g., in [17-19, 36, 37].

In order to identify a patient that is to be treated with the herein provided binding molecule or pharmaceutical composition also imaging techniques may be used. For example, advanced medical imaging with computed tomography (CT) or magnetic resonance imaging (MRI), or single-photon emission computed tomography (SPECT) or positron emission tomography (PET) may be used to help to diagnose neurological disorders such as neurodegenerative disorders.

As described above, carriers of the p.H157Y mutation suffer from increased TREM2 shedding. Therefore, inhibition of cleavage of TREM2 at the position His157 may particularly benefit from the administration of the binding molecule or pharmaceutical composition provided herein. Accordingly, one aspect of the present invention relates to the herein provided binding molecule, pharmaceutical composition, therapeutic method, wherein a neurodegenerative disorder is treated and/or prevented in a patient who carries the p.H157Y mutation of TREM2.

Certain aspects of the present invention are defined by the following items.

1. A binding molecule having a binding site within the ectodomain of the triggering receptor expressed on myeloid cells 2 (TREM2), wherein the binding molecule inhibits TREM2 cleavage.
2. The binding molecule of item 1, wherein the binding site comprises at least one of the positions of human membrane bound TREM2 selected from the group consisting of:
   glutamic acid at position 148 (Glu148);
   serine at position 149 (Ser149);
   phenylalanine at position 150 (Phe150);
   glutamic acid at position 151 (Glu151);
   aspartic acid at position 152 (Asp152);
   alanine at position 153 (Ala153);
   histidine at position 154 (His154);
   valine at position 155 (Val155);
   glutamic acid at position 156 (Glu156);
   histidine at position 157 (His157);
   serine at position 158 (Ser158);
   isoleucine at position 159 (Ile 159);
   serine at position 160 (Ser160);
   arginine at position 161 (Arg161);
   serine at position 162 (Ser162);
   leucine at position 163 (Leu163);
   leucine at position 164 (Leu164);
   glutamic acid at position 165 (Glu165); and
   glycine at position 166 (Gly166).
3. The binding molecule of item 1, wherein the binding site comprises at least one of the positions of murine membrane bound TREM2 selected from the group consisting of:
   serine at position 148 (Ser148);
   serine at position 149 (Ser149);
   phenylalanine at position 150 (Phe150);
   glutamic acid at position 151 (Glu151);
   glycine at position 152 (Gly152);
   alanine at position 153 (Ala153);
   glutamine at position 154 (Gln154);
   valine at position 155 (Val155);
   glutamic acid at position 156 (Glu156);
   histidine at position 157 (His157);
   serine at position 158 (Ser158);
   threonine at position 159 (Thr159);
   serine at position 160 (Ser160);
   arginine at position 161 (Arg161);
   asparagine at position 162 (Asn162);
   glutamine at position 163 (Gln163);
   glutamic acid at position 164 (Glu164);
   threonine at position 165 (Thr165); and
   serine at position 166 (Ser166).
4. The binding molecule of any one of items 1-3, wherein the binding site comprises or overlaps with any one of the polypeptides having an amino acid sequence as shown in any one of SEQ ID NOs: 7-15, 21 and 22.
5. The binding molecule of any one of items 1-4, wherein the binding site comprises histidine at position 157 of TREM2.
6. The binding molecule of any one of items 1-5, wherein the binding molecule inhibits TREM2 cleavage by inhibiting access of the cleaving enzyme to TREM2.
7. The binding molecule of any one of items 1-6, wherein inhibition of TREM2 cleavage is assayed by immunoblotting, ELISA-based quantification of soluble TREM2, quantification of surface-bound TREM2 by surface biotinylation assays, quantification of surface-bound TREM2 by flow-cytometry, quantification of surface-bound TREM2 by surface immunocytochemistry and/or quantification of surface-bound TREM2 by a cell-based ELISA technique
8. The binding molecule of any one of items 1-7, wherein in the presence of said binding molecule the amount of membrane-bound TREM2 is at least 10% more than the amount of membrane-bound TREM2 in the absence of the binding molecule.
9. The binding molecule of any one of items 6-8, wherein the cleaving enzyme is a metalloproteinase.
10. The binding molecule of any one of items 6-9, wherein the binding molecule interferes with the binding of a cleaving enzyme to TREM2, wherein the cleaving enzyme is a disintegrin and metalloproteinase domain-containing protein (ADAM) or a matrix metalloproteinase (MMP).
11. The binding molecule of item 10, wherein ADAM is ADAM10 and/or ADAM17.
12. The binding molecule of any one of items 1-11, wherein the binding molecule preserves and/or stimulates activity of microglia cells, and/or the activity of other TREM2 expressing cells.
13. The binding molecule of item 12, wherein the activity of microglia cells and/or other TREM2 expressing cells is phagocytosis activity, migration, calcium signaling, Syk activation, proliferation, regulation of inflammatory cytokine production and/or survival.
14. The binding molecule of any one of items 1-13, wherein the binding molecule is an antibody or a small molecule.
15. The binding molecule of item 14, wherein the antibody is a monoclonal antibody.
16. The binding molecule of item 14 or 15, wherein the antibody is an antibody fragment.
17. The binding molecule of item 16, wherein the antibody fragment is a nanobody, a Fab fragment, a Fab' fragment, a Fab'-SH fragment, a F(ab')$_2$ fragment, a Fd fragment, a Fv fragment, a scFv fragment, or an isolated complementarity determining region (CDR).
18. The binding molecule of any one of items 15-17, wherein the antibody or antibody fragment is a humanized antibody/antibody fragment, a fully human antibody/antibody fragment, a mouse antibody/antibody fragment, a rat antibody/antibody fragment, a rabbit antibody/antibody fragment, a hamster antibody/antibody fragment, a goat antibody/antibody fragment, a guinea pig antibody/antibody fragment, a ferret antibody/antibody fragment, a chicken antibody/antibody fragment, a sheep antibody/antibody fragment, or a monkey antibody/antibody fragment.
19. The binding molecule of any one of items 15-18, wherein the antibody is a chimeric antibody and/or a bispecific antibody.
20. The binding molecule of any one of items 14-19, wherein the antibody is any one of the following antibodies:
   (1) an antibody, wherein the heavy chain variable region comprises the sequence of SEQ ID NO: 32 and the light chain variable region comprises the sequence of SEQ ID NO: 42; and wherein the antibody inhibits TREM2 cleavage;

(2) an antibody, wherein the heavy chain variable region comprises a sequence having at least 85% identity to SEQ ID NO: 32, and the light chain variable region comprises a sequence having at least 85% identity to SEQ ID NO: 42; and wherein the antibody inhibits TREM2 cleavage;

(3) an antibody, wherein the CDR1 of the heavy chain variable region comprises the amino acid sequence of SEQ ID NO: 52; the CDR2 of the heavy chain variable region comprises the amino acid sequence of SEQ ID NO: 62; and the CDR3 of the heavy chain variable region comprises the amino acid sequence of SEQ ID NO: 72; the CDR1 of the light chain variable region comprises the amino acid sequence of SEQ ID NO: 82; the CDR2 of the light chain variable region comprises the amino acid sequence of SEQ ID NO: 92; and the CDR3 of the light chain variable region comprises the amino acid sequence of SEQ ID NO: 102; and wherein the antibody inhibits TREM2 cleavage; or (4) an antibody, wherein the CDR1 of the heavy chain variable region comprises an amino acid sequence having at least 70% identity to SEQ ID NO: 52; the CDR2 of the heavy chain variable region comprises an amino acid sequence having at least 70% identity to SEQ ID NO: 62; the CDR3 of the heavy chain variable region comprises an amino acid sequence having at least 70% identity to SEQ ID NO: 72; the CDR1 of the light chain variable region comprises an amino acid sequence having at least 70% identity to SEQ ID NO: 82; the CDR2 of the light chain variable region comprises an amino acid sequence having at least 60% identity to SEQ ID NO: 92; and the CDR3 of the light chain variable region comprises an amino acid sequence having at least 70% identity to SEQ ID NO: 102; and wherein the antibody inhibits TREM2 cleavage.

21. The binding molecule of any one of items 1-20, wherein TREM2 is a polypeptide comprising or consisting of
   (i) the amino acid sequence of any one of SEQ ID NOs: 1-6; or
   (ii) an amino acid sequence having at least 80% identity to an amino acid sequence of (i), wherein the polypeptide has the activity to promote proper phagocytosis, migration, and/or survival of microglia cells and/or other TREM2 expressing cells.

22. The binding molecule of any one of items 1-21, wherein the ectodomain of TREM2 is a polypeptide comprising or consisting of
   (i) the amino acid sequence of SEQ ID NO: 17 or 18; or
   (ii) an amino acid sequence having at least 80% identity to an amino acid sequence of (i), wherein when combined with the intracellular domain of TREM2 the polypeptide has the activity to promote proper phagocytosis, migration, proliferation and/or survival of microglia cells and/or other TREM2 expressing cells.

23. The binding molecule of item 22, wherein the intracellular domain of TREM2 is a polypeptide comprising or consisting of
   (i) the amino acid sequence of SEQ ID NO: 19 or 20; or
   (ii) an amino acid sequence having at least 80% identity to an amino acid sequence of (i), wherein when combined with the ectodomain of TREM2 the polypeptide has the activity to promote proper phagocytosis, migration, proliferation and/or survival of microglia cells and/or other TREM2 expressing cells.

24. The binding molecule of any one of items 1-23 for use in treating and/or preventing a neurological disorder.

25. A pharmaceutical composition for use in treating and/or preventing a neurological disorder, wherein the pharmaceutical composition comprises
   (i) the binding molecule of any one of items 1-23; and
   (ii) optionally a pharmaceutically acceptable carrier.

26. Method for treating and/or preventing a neurological disorder, wherein the method comprises administering an effective amount of the binding molecule of any one of items 1-23 to a subject in need of such a treatment.

27. The binding molecule for the use according to item 24, the pharmaceutical composition for the use according to item 25, or the method of item 26, wherein the neurological disorder is a neurological disorder with an inflammatory component.

28. The binding molecule for the use according to item 24 or 27, the pharmaceutical composition for the use according to item 25 or 27, or the method of item 26 or 27, wherein the neurological disorder is a neurodegenerative disorder.

29. The binding molecule for the use according to item 28, the pharmaceutical composition for the use according to item 28, or the method of item 28, wherein the neurodegenerative disorder is characterized by a decreased function of microglia cells and/or other TREM2 expressing cells.

30. The binding molecule for the use according to item 28 or 29, the pharmaceutical composition for the use according to item 28 or 29, or the method of item 28 or 29, wherein said neurodegenerative disorder is characterized by the accumulation of amyloid plaques and/or hyperphosphorylated tau.

31. The binding molecule for the use according to any one of items 28-30, the pharmaceutical composition for the use according to any one of items 28-30, or the method of any one of items 28-30, wherein said neurodegenerative disorder is Alzheimer's disease (AD), Frontotemporal lobar degeneration (FTLD), FTLD-like syndrome, Parkinson's disease, Nasu-Hakola disease, Multiple sclerosis (MS), Huntington disease, immune-mediated neuropathies, or Amyotrophic lateral sclerosis (ALS).

32. The binding molecule for the use according to any one of items 24 and 27-31, the pharmaceutical composition for the use according to any one of items 25 and 27-31, or the method of any one of items 26-31, wherein the treatment and/or prevention is a co-therapy, wherein said binding molecule or said pharmaceutical composition is to be administered simultaneously or sequentially with another active agent.

33. The binding molecule for the use according to item 32, the pharmaceutical composition for the use according to item 32, or the method of item 32, wherein said other active agent is an acetylcholinesterase inhibitor, a N-Methyl-D-aspartate receptor (NMDAR) antagonist or an immunotherapeutic.

34. The binding molecule for the use according to item 33, the pharmaceutical composition for the use according to item 33, or the method of item 33, wherein said immunotherapeutic is A-beta immunotherapy.

35. The binding molecule for the use according to item 34, the pharmaceutical composition for the use according to item 34, or the method of item 34, wherein said A-beta immunotherapy comprises antibodies that are specific for the amyloid-beta peptide.

36. The binding molecule for the use according to any one of items 24 and 27-35, the pharmaceutical composition for the use according to any one of items 25 and 27-35, or the method of any one of items 26-35, wherein a neurological disorder is treated and/or prevented in a patient, whose cerebrospinal fluid (CSF) has an increased level of soluble TREM2 (sTREM2), total-tau, and/or phospho-tau as compared to the CSF of a healthy control person.

37. The binding molecule for the use according to any one of items 24 and 27-36, the pharmaceutical composition for the use according to any one of items 25 and 27-36, or the method of any one of items 26-37, wherein a neurodegenerative disorder is treated and/or prevented in a patient who carries the p.H157Y mutation of TREM2.

Herein the term "antibody" includes a peptide or polypeptide derived from, modelled after or substantially encoded by an immunoglobulin gene or immunoglobulin genes, or fragments thereof, capable of specifically binding an antigen or epitope, see, e.g. [38-40]. The term "antibody" includes antigen-binding portions, i.e., "antigen binding sites," (e.g., fragments, subsequences, or complementarity determining regions (CDRs)) that retain capacity to bind an antigen (such as TREM2), comprising or alternatively consisting of, for example, (i) a Fab fragment, i.e. a monovalent fragment consisting of the VL, VH, CL and CH1 domains; (ii) a F(ab')$_2$ fragment, i.e. a bivalent fragment comprising two Fab fragments linked by a disulfide bridge at the hinge region; (iii) a Fab' fragment, i.e. one of the two fragments that are formed if a F(ab')$_2$ fragment is split by mild reduction; (iv) a Fab'-SH fragment, i.e. a Fab' fragment containing a free sulfhydryl group; (v) a Fd fragment consisting of the VH and CH1 domains; (vi) a Fv fragment consisting of the VL and VH domains of a single arm of an antibody; (vii) a scFv fragment, i.e. a single-chain variable fragment, wherein the variable regions of the heavy and light chains are fused together; or (viii) an isolated complementarity determining region (CDR). The herein provided antibody fragment may also be (ix) a dAb fragment, which consists of a VH domain (see, e.g. Ward et al. [41]).

The herein provided antibody fragment may also be a single-domain antibody, sdAb. Single-domain antibodies are also called nanobody; see, e.g., Gibbs, 2005, "Nanobodies", Scientific American Magazine. A sdAb or nanobody is an antibody fragment consisting of a single monomeric variable antibody domain. With a molecular weight of only 12-15 kDa, single-domain antibodies are much smaller than common antibodies (150-160 kDa) that are composed of two heavy protein chains and two light chains, and even smaller than Fab fragments (~50 kDa, one light chain and half a heavy chain) and single-chain variable fragments (~25 kDa, two variable domains, one from a light and one from a heavy chain); see, e.g. [42].

Various procedures are known in the art and may be used for the production of such antibodies and/or fragments (see, for example, [43]. Herein the abbreviations "VL", "VH", "CL" and "CH" refer to variable domain of the antibody light chain, variable domain of the antibody heavy chain, constant domain of the antibody light chain and constant domain of the antibody heavy chain, respectively.

Antibody fragments can be prepared, for example, by recombinant techniques or enzymatic or chemical cleavage of intact antibodies. For producing a single chain Fv (scFv) the two domains of the Fv fragment, VL and VH, can be joined, using recombinant methods, by a synthetic linker that enables them to be made as a single protein chain in which the VL and VH regions pair to form a monovalent molecule (see, e.g., Bird et al. [44] and [45]. Further techniques for the production of single chain antibodies are described, e.g., [46] and U.S. Pat. No. 4,946,778.

Methods of immunization, producing and isolating antibodies (polyclonal and monoclonal) are known to those skilled in the art and described in the scientific and patent literature, (see, e.g., [47-50]). Antibodies can also be generated in vitro, e.g., by using a recombinant antibody binding site expressing phage display library; in addition or alternatively to the traditional in vivo methods using animals (see, e.g., Hoogenboom [51] and Katz [52].

The ability of an antibody to bind to an antigen (such as the ectodomain of TREM2) may be determined by using any of a variety of procedures familiar to those skilled in the art. For example, binding may be determined by labeling the antibody with a detectable label such as a fluorescent agent, an enzymatic label, or a radioisotope. Alternatively, binding of the antibody to the antigen may be detected by using a secondary antibody having such a detectable label thereon. Particular assays include ELISA assays, sandwich assays, radioimmunoassays, immunohistochemical methods and Western Blots.

For example, the generation and selection of monoclonal antibodies against the TREM2 cleavage site may be performed as follows. A peptide comprising the TREM2 cleavage site (e.g. a peptide comprising the amino acid sequence AHVEHSISRS, SEQ ID NO: 7) may be coupled at the N-terminus to ovalbumin (OVA). Non-human animals such as mice or rats may be immunized with the OVA-coupled peptide and incomplete Freund's adjuvant. After 6 weeks, a boost without incomplete Freund's adjuvant may be given 3 days before fusion. Fusion of the myeloma cell line P3X63-Ag8.653 with the immune spleen cells may be performed using polyethylene glycol 1500 according to standard procedure (Koehler and Milstein, Nature. 1975, 256:495-497). Hybridoma supernatants may be tested for binding to the peptide (e.g. the peptide of SEQ ID NO: 7) in an enzyme-linked immunoassay using a biotinylated version of the peptide bound to avidin-coated plates. Bound antibodies may be detected with antibodies against IgG isotypes.

TREM2-reactive hybridoma supernatants may be screened for their ability to detect TREM2 on the cell surface of HEK293 Flp-In cells stably overexpressing human wild-type TREM2. This procedure is described in Kleinberger et al. 2014. In particular, HEK293 Flp-In cells either expressing human full-length TREM2 or empty vector (control) may be incubated with the respective TREM2-reactive supernatants. Binding of TREM2-reactive supernatants may be visualized using isotype-specific antibodies. A detailed description of the generation and selection of monoclonal antibodies against the TREM2 cleavage site is given in the Examples.

The antibody useful in context of the present invention can be, for example, polyclonal or monoclonal. The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. For preparation of monoclonal antibodies, several techniques which provide antibodies by continuous cell culture can be used. Examples include the hybridoma technique [50], the trioma technique, the human B-cell hybridoma technique [53] and the EBV-hybridoma technique [54]. For example, the monoclonal antibodies to be used in accordance with the present invention may be made by the hybridoma method first described by Kohler and Milstein [50], or may be made by recombinant methods, e.g., as described in U.S. Pat. No. 4,816,567. The monoclonal antibodies for use with the present invention may also be isolated from phage antibody libraries, e.g. using the techniques described in Clackson et al. [55]; as well as in Marks et al. [56].

The term "polyclonal antibody" as used herein, refers to an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

Herein, term "antibody" further comprises diclonal and oligoclonal antibodies. The term "diclonal antibody" refers to a preparation of at least two antibodies to a target protein (such as the ectodomain of TREM2). Typically, the different antibodies bind different epitopes. The term "oligoclonal antibody" refers to a preparation of 3 to 100 different antibodies to a target protein (such as the ectodomain of TREM2). Typically, the antibodies in such a preparation bind to a range of different epitopes.

The term "antibody" also relates to bispecific (i.e. bifunctional) antibodies. The term "bispecific antibody" as used herein refers to an artificial hybrid antibody having two different heavy/light chain pairs and two different binding sites. Bispecific antibodies can be produced by a variety of methods including fusion of hybridomas or linking of Fab' fragments (see, e.g., Songsivilai et al. [57] and Kostelny et al. [58]. In addition, bispecific antibodies may be formed as "diabodies [59] or as "Janusins" [60] and [61]. The term "antibody" also relates to a "trifunctional antibody".

The herein provided antibody may further be a fully-human antibody, a mouse antibody or a rat antibody. The term "fully-human antibody" as used herein refers to an antibody that comprises human immunoglobulin protein sequences only. A fully human antibody may contain murine carbohydrate chains if produced in a mouse, in a mouse cell or in a hybridoma derived from a mouse cell. Alternatively, a "fully-human antibody" may contain rat carbohydrate chains if produced in a rat, in a rat cell, in a hybridoma derived from a rat cell. Similarly, "(fully-)mouse antibody" or "(fully-) murine antibody" refers to an antibody that comprises mouse (murine) immunoglobulin protein sequences only. The term "(fully-) rat antibody" refers to an antibody that comprises rat immunoglobulin sequences only. In line with this the terms "(fully-)rabbit antibody", "(fully-) hamster antibody", "(fully-)goat antibody", "(fully-)guinea pig antibody", "(fully-) ferret antibody", "(fully-)cat antibody", "(fully-)dog antibody", "(fully-)chicken antibody", "(fully-)sheep antibody", "(fully-) bovine antibody", "(fully-)horse antibody", "(fully-)camel antibody" and "(fully-)monkey antibody" refer to an antibody that comprises rabbit, hamster, goat, guinea pig, ferret, cat, dog, chicken, sheep, bovine, horse, camel, or monkey, respectively, immunoglobulin sequences only.

Fully-human antibodies may be produced, for example, by phage display, which is a widely used screening technology that enables production and screening of fully-human antibodies. Accordingly, also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397). (Fully-)mouse or (Fully-)rat antibodies may be produced analogously.

The herein provided antibody may also be a chimeric antibody. The term "chimeric antibody" refers to an antibody that comprises a variable region of a human or non-human species fused or chimerized with an antibody region (e.g., constant region) from another, human or non-human species (e.g., mouse, horse, rabbit, dog, cow, chicken).

Herein, the term "antibody" also relates to recombinant human antibodies, heterologous antibodies and heterohybrid antibodies. The term "recombinant human antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library; or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis); and thus, the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal. The term "heterohybrid antibody" refers to an antibody having light and heavy chains of different organisms. For example, an antibody having a human heavy chain associated with a murine light chain is a heterohybrid antibody. Examples of heterohybrid antibodies include chimeric and humanized antibodies.

The herein provided antibody may also be a humanized antibody. "Humanized" forms of non-human (e.g. murine or rabbit) antibodies are chimeric immunoglobulins, immunoglobulin chains or fragments thereof (such as Fv, Fab, Fab', Fab'-SH, F(ab')$_2$, Fd, scFv, or other antigen-binding subsequences of antibodies), which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. A humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least one portion of an immunoglobulin constant region (Fc), typically that of a human immunoglobulin. For further details, see, e.g. Jones et al. [62], Riechmann et al. [63] and Presta et al. [64]. Also, transgenic animals may be used to express humanized antibodies. A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci, which are capable of undergoing gene rearrangement and gene conversion (see, for example, U.S. Pat. No. 7,129,084).

Accordingly, in the context of the present invention, the term "antibody" relates to full immunoglobulin molecules as well as to parts of such immunoglobulin molecules. Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fab', Fab'-SH, Fab/c, Fv, Fd, scFv, di-scFv, sdAb, Fab', F(ab')$_2$, or an isolated CDR. The herein provided antibody may further be a bifunctional antibody, a trifunctional antibody, a fully-human antibody, a mouse antibody, a rat antibody, a rabbit antibody, a chimeric antibody, a humanized antibody, or an antibody construct, like scFv- or antibody-fusion proteins. As mentioned, techniques for the production of antibodies are well known in the art and summarized, e.g., in Petering et al. [65]. In addition, several techniques for the production of antibodies are described, e.g. in Harlow "Antibodies, A Laboratory Manual", CSH Press, Cold Spring Harbor, 1988.

The binding molecule of the present invention may be a naturally occurring molecule, e.g. a naturally occurring antibody. However, the binding molecule of the present invention may also be a non-naturally occurring molecule. For example, the binding molecule of the invention may be an antibody having an amino acid sequence that is not identical to naturally occurring antibodies or may be an antibody comprising at least one non-naturally occurring amino acid residue such as synthetic amino acids providing similar side chain functionality. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)phenylglycine, D-(trifluoromethyl)-phenylglycine, D-(trifluoromethyl)-phenylalanine, D-p-fluorophenylalanine, D- or L-pbi-phenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl. Non-carboxylate amino acids can be made to possess a negative charge, as provided by phosphono- or sulfated amino acids, which are to be considered as non-limiting examples. Further non-natural amino acids are alkylated amino acids, made by combining an alkyl group with any natural amino acid. Basic natural amino acids such as lysine and arginine may be substituted with alkyl groups at the amine (NH$_2$) functionality. Yet other substitutions on non-natural amino acids include nitrile derivatives (e.g., containing a ON-moiety in place of the CONH$_2$ functionality) of asparagine or glutamine, and sulfoxide derivative of methionine.

The herein provided antibody may also be a high affinity antibody. The term "high affinity" for an antibody refers to an equilibrium association constant (K$_a$) of at least about $10^7$ M$^{-1}$, at least about $10^8$ M$^{-1}$, at least about $10^9$ M$^{-1}$, at least about $10^{10}$ M$^{-1}$, at least about $10^{11}$ M$^{-1}$, or at least about $10^{12}$ M$^{-1}$ or greater, e.g., up to $10^{13}$ M$^{-1}$ or $10^{14}$ M$^{-1}$ or greater. However, "high affinity" binding can vary among antibody isotypes. The term "K$_a$", as used herein, is intended to refer to the equilibrium association constant of a particular antibody-antigen interaction. This constant has a unit of 1/M. A "high affinity antibody" is usually an antibody that has undergone extensive hypermutation, affinity maturation and proper isotype switching to applicable isotypes such as preferably IgG.

Preferably, the herein provided binding molecule specifically binds to the ectodomain of TREM2. The phrase "specifically bind(s)" or "bind(s) specifically" when referring to a binding molecule refers to a binding molecule which has intermediate or high binding affinity, exclusively or predominately, to a target molecule, such as the ectodomain of TREM2. The phrase "specifically binds to" refers to a binding reaction which is determinative of the presence of a target protein (such as the ectodomain of TREM2) in the presence of a heterogeneous population of proteins and other biologics. Thus, under designated assay conditions, the specified binding molecules bind preferentially to a particular target protein (e.g. the ectodomain of TREM2) and do not bind in a significant amount to other components present in a test sample. Specific binding to a target protein under such conditions may require a binding molecule that is selected for its specificity for a particular target protein. A variety of assay formats may be used to select binding molecules that are specifically reactive with a particular target protein. For example, solid-phase ELISA immunoassays, immunoprecipitation, Biacore and Western blot may be used to identify binding molecules that specifically bind to the ectodomain of TREM2. Typically, a specific or selective reaction will be at least twice background signal or noise and more typically more than 10 times background. Given that the binding molecule is an antibody, the phrase "specifically binds to" refers to a binding reaction that is determinative of the presence of the antigen (such as the ectodomain of TREM2) in a heterogeneous population of proteins and other biologics. Typically, an antibody that specifically binds to its antigen binds said antigen with an association constant (K$_a$) of at least about $1\times10^6$ M$^{-1}$ or $10^7$ M$^{-1}$, or about $10^8$ M$^{-1}$ to $10^9$ M$^{-1}$, or about $10^{10}$ M$^{-1}$ to $10^{11}$ M$^{-1}$ or higher; and/or binds to the predetermined antigen (e.g. the ectodomain of TREM2) with an affinity that is at least two-fold greater than its affinity for binding to a non-specific antigen (e.g., BSA, casein) other than the predetermined antigen or a closely-related antigen.

As described above, the invention relates to a binding molecule for use in treating and/or preventing a neurological disorder such as a neurodegenerative disorder; and a pharmaceutical composition comprising said binding molecule. Said pharmaceutical composition (i.e. medicament) optionally comprises a pharmaceutically acceptable carrier. Said pharmaceutical composition may further comprise a therapeutically acceptable diluent or excipient.

A typical pharmaceutical composition according to the present invention is prepared by mixing the herein provided binding molecule and a carrier or excipient. Suitable carriers and excipients are well known to those skilled in the art and are described in detail in, e.g., [66-68]. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to improve appearance of the drug or aid in the manufacturing of the pharmaceutical product (i.e., medicament). For example, the pharmaceutical composition of the invention may be formulated by mixing the binding molecule of the invention at ambient temperature at an appropriate pH, and with the desired degree of purity, with physiologically acceptable carriers, i.e., carriers that are non-toxic to recipients at the dosages and concentrations employed into a suitable administration form. The pharmaceutical composition of the invention may be sterile.

The binding molecule according to the present invention may exist in the form of a pharmaceutically acceptable salt. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in [69] or in [70]. For example, the pharmaceutically acceptable salt of the compounds provided herein may be a sodium salt.

The pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of the binding molecule of the invention, or the pharmaceutical composition of the invention will be governed by such considerations, and is the minimum amount necessary to inhibit the symptoms of the neurological disorder to be treated. For example, such amount may be below the amount that is toxic to the cells of the recipient, or to the mammal as a whole.

The binding molecule of the invention or the pharmaceutical composition of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. As discussed above, osmotic pumps may be used to directly deliver the binding molecule or the pharmaceutical composition of the invention into the CNS, e.g. into the brain.

The binding molecule of the invention or the pharmaceutical composition of the invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

As described above, the binding molecule of the invention or the pharmaceutical composition of the invention are useful in the prevention and/or treatment of a neurological disorder including a neurodegenerative disorder such as AD. The terms "treatment", "treating", "treats" or the like are used herein to generally mean obtaining a desired pharmacological and/or physiological effect. This effect is therapeutic in terms of partially or completely curing a disease and/or adverse effect attributed to the disease. The term "treatment" as used herein covers any treatment of a disease in a subject and includes: (a) inhibiting the disease, i.e. arresting its development like the inhibition of the formation of amyloid plaques; or (b) ameliorating (i.e. relieving) the disease, i.e. causing regression of the disease, like the regression of amyloid plaques. Thus, a compound that treats a neurological disorder such as a neurodegenerative disorder is a compound that ameliorates and/or inhibits a neurological disorder such as a neurodegenerative disorder. Preferably, the term "treatment" as used herein relates to medical intervention of an already manifested neurological disorder, like the treatment of an already defined and manifested neurodegenerative disorder. Herein the term "preventing", "prevention" or "prevents" relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein "preventing a neurological/neurodegenerative disorder" includes preventing a neurological/neurodegenerative disorder from occurring in a subject, and preventing the occurrence of symptoms of a neurological/neurodegenerative disorder.

For the purposes of the present invention the "subject" (or "patient") may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, goat, guinea pig, ferret, cat, dog, chicken, sheep, bovine species, horse, camel, or monkey such as primate. Preferably, the subject is a mammal. More preferably the subject is a mouse or a human. Most preferably, the subject is a human.

Herein, term "polypeptide" includes all molecules that comprise or consist of amino acid monomers linked by peptide (amide) bonds. Thus, the term "polypeptide" comprises all amino acid sequences, such as peptides, oliogopeptides, polypeptides and proteins. The "polypeptide" described herein may be a naturally occurring polypeptide or a non-naturally occurring polypeptide. The non-naturally occurring polypeptide may comprise at least one mutation (e.g. amino acid substitution, amino acid deletion or amino acid addition) as compared to the naturally occurring counterpart. The non-naturally occurring polypeptide may also be cloned in a vector and/or be operable linked to a promoter that is not the natural promoter of said polypeptide. Said promoter may be a constitutively active promoter. The term "amino acid" or "residue" as used herein includes both L- and D-isomers of the naturally occurring amino acids as well as of other amino acids (e.g., non-naturally-occurring amino acids, amino acids which are not encoded by nucleic acid sequences, synthetic amino acids etc.). Examples of naturally-occurring amino acids are alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophane (Trp; W), tyrosine (Tyr; Y), valine (Val; V). Post-translationally modified naturally-occurring amino acids are dehydrobutyrine (Dhb) and labionin (Lab). Examples for non-naturally occurring amino acids are described above. The non-naturally occurring polypeptide may comprise one or more non-amino acid substituents, or heterologous amino acid substituents, compared to the amino acid sequence of a naturally occurring form of the polypeptide, for example a reporter molecule or another ligand, covalently or non-covalently bound to the amino acid sequence.

In context of the present invention, the term "identity" or "percent identity" means that amino acid or nucleotide sequences have identities of at least 80%, preferably at least 90%, more preferably at least 95%, even more preferably at least 98%, and even more preferably at least 99% identity to the sequences shown herein, e.g. those of SEQ ID NO: 1-6 or 17-20, wherein the higher identity values are preferred upon the lower ones. In accordance with the present invention, the term "identity/identities" or "percent identity/identities" in the context of two or more nucleic acid or amino acid sequences, refers to two or more sequences that are the same, or that have a specified percentage of amino acid residues or nucleotides that are the same (e.g., at least 80%, at least 90%, at least 95%, at least 98%, or at least 99% identity with the amino acid sequences of, e.g., SEQ ID NO: 1-6 or 17-20, when compared and aligned for maximum correspondence over a window of comparison, or over a designated region as measured using a sequence comparison algorithm as known in the art, or by manual alignment and visual inspection. Preferably the described identity exists over all amino acids of the herein provided sequences in length.

Those having skills in the art will know how to determine percent identity between/among sequences using, for example, algorithms such as those based on CLUSTALW computer program [71] or FASTDB [72], as known in the art. Also available to those having skills in this art are the BLAST and BLAST 2.0 algorithms [73-75]. For example, BLAST 2.0, which stands for Basic Local Alignment Search Tool BLAST [73-75], can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. Analogous computer techniques using BLAST [73-75] are used to search for identical or related molecules in nucleotide databases such as GenBank or EMBL.

The present invention is further described by reference to the following non-limiting Figures, Tables and Examples.

The Figures and Tables show:

FIG. 1. Identification of TREM2 ectodomain cleavage site (A) Illustration of membrane-bound TREM2. Upon shedding by ADAM10, the remaining C-terminal stub of TREM2 is cleaved within the membrane by γ-secretase. Identified TREM2 variants resulting in amino-acid changes are indicated.

(B) C-terminally FLAG-tagged TREM2 stably expressed in HEK293 cells was used to identify the ectodomain cleavage site. In order to enrich for the TREM2 C-terminal fragment cells were treated with 10 μM DAPT prior to protein extraction. The graph on the right shows one prominent peak fitting with cleavage after His157 identified by MALDI-TOF mass spectrometry after DAPT treatment. Treatments with ADAM inhibitors (GM, broad ADAM inhibitor; GI, ADAM10 selective inhibitor) show no identified peak (bottom graphs).

(C) Alternative strategy to identify TREM2 ectodomain cleavage site. A TEV-protease cleavage site followed by a FLAG-tag was introduced after amino acid 140 of TREM2. Soluble TREM2 was purified from supernatants. The N-terminal part containing the Ig-like V-type domain was removed by TEV-protease cleavage, the remaining C-terminal peptide purified using anti-FLAG antibodies and analyzed by MALDI-TOF mass spectrometry. The graph on the right shows a single peak corresponding to a peptide cleaved after His157.

(D) Increase of ADAM17 activity after PMA treatment shows a single peak confirming cleavage at H157 without inducing major alternative cleavage products.

(E) Illustration (SEQ ID NO:115) of the major TREM2 ectodomain cleavage site at position H157. Minor alternative cleavage sites are detected at L163, L164 and E165. Amino acids with dark grey background indicate the start of the TREM2 transmembrane domain. The decameric peptide (SEQ ID NO:7) encompassing the ectodomain cleavage site that was used for immunization of rats to generate cleavage-site-specific antibodies is indicated by a box.

Figure 2:
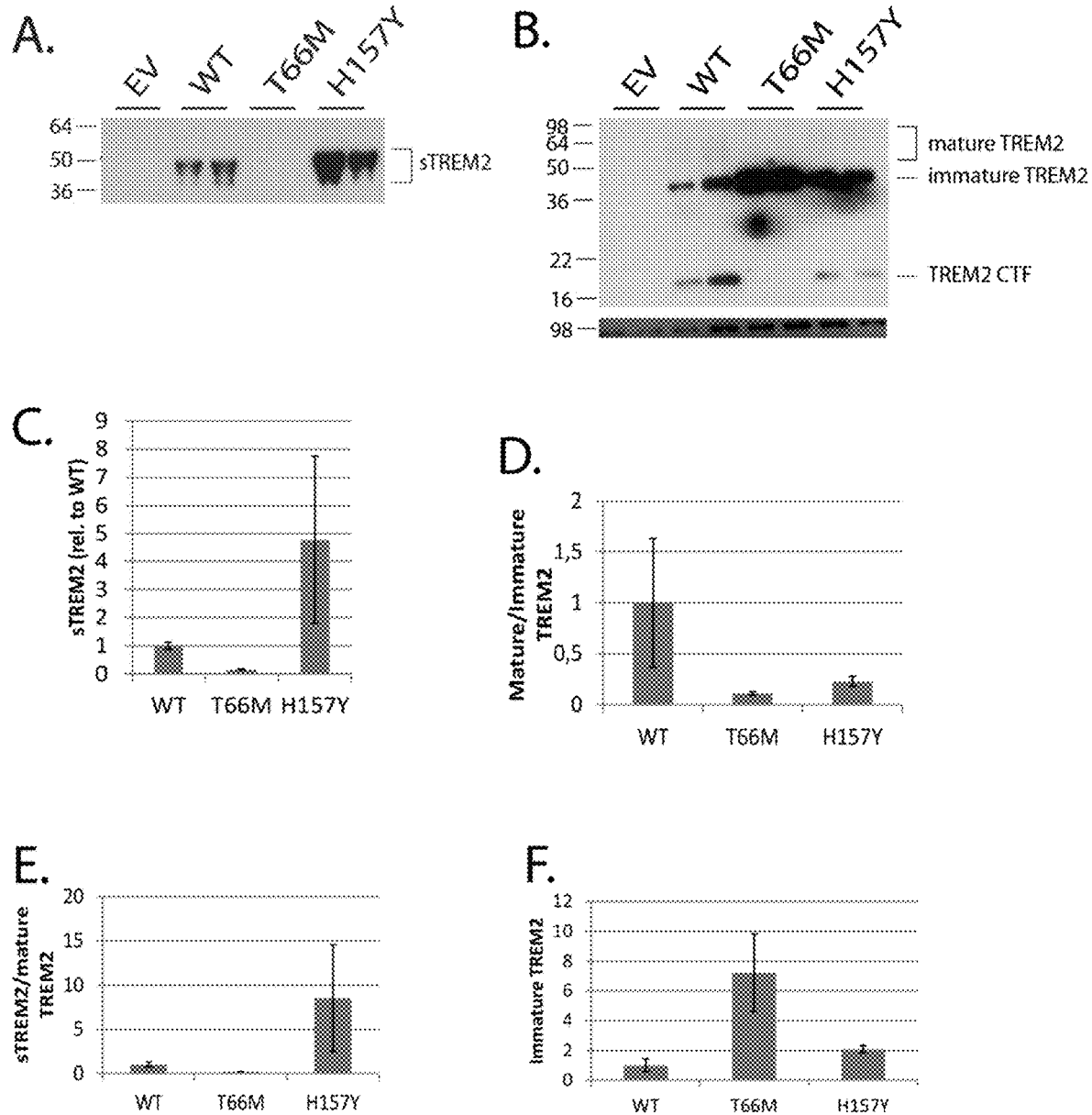
Figure 2:
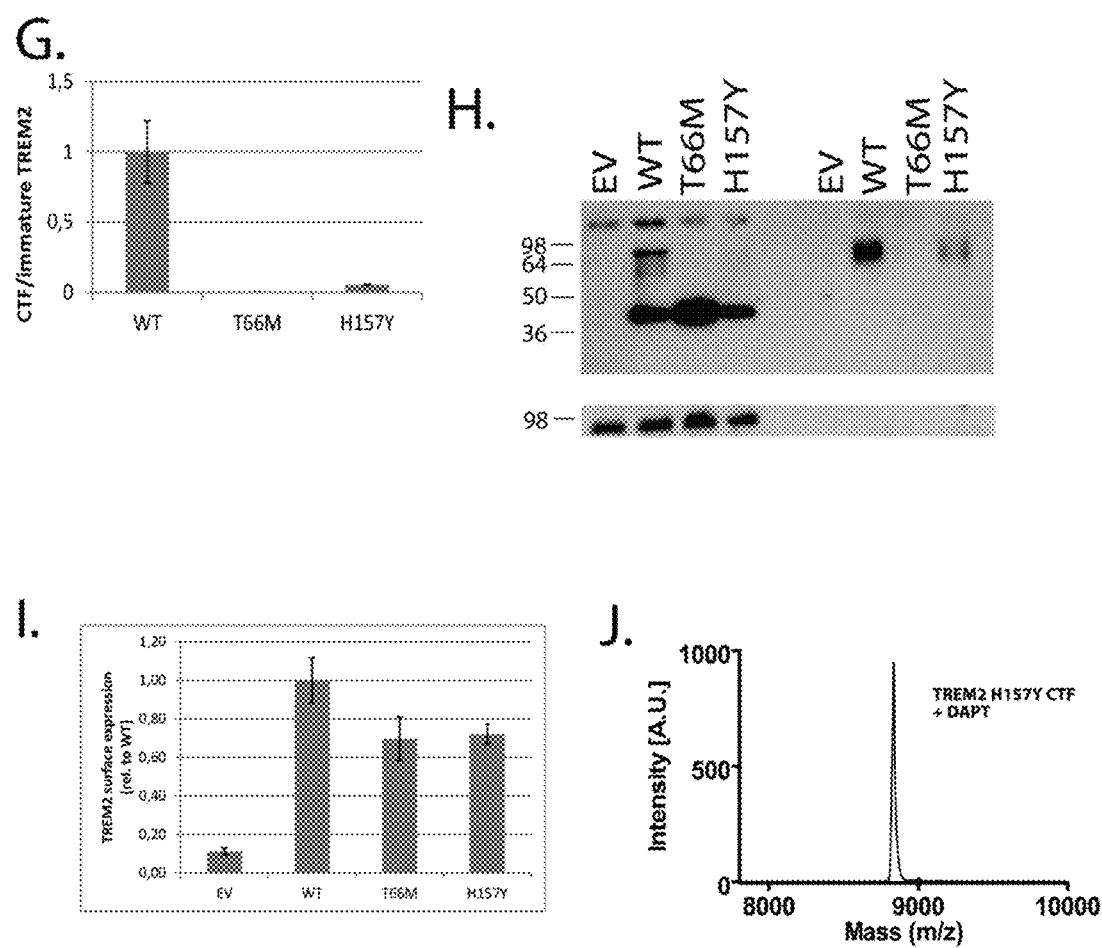

FIG. 2. Increased shedding of patient associated TREM2 H157Y variant (A) Anti-HA immunoblotting of sTREM2 in supernatants from cells expressing the AD-associated variant p.H157Y show increased sTREM2 levels compared to wild-type (WT) control. FTD-like-associated TREM2 mutation p.T66M was used as a control for reduced shedding [15]

(B) Immunoblotting of membrane-bound TREM2 shows reduced levels of mature TREM2 (smear above immature band). Note that the C-terminal fragment also shows reduced levels in H157Y expressing cells. 9D11 antibody was used for immunoblotting which is specific for human TREM2 C terminus.

(C) Quantification of sTREM2 levels.

(D) Quantification of mature/immature TREM2 levels.

(E) Quantification of sTREM2/mature TREM2 levels.

(F) Quantification of immature TREM2.

(G) Quantification of TREM2 CTF/immature TREM2 levels.

(H) Surface biotinylation of mature surface exposed mutant TREM2 shows reduced levels of surface bound p.H157Y TREM2. FTD-like-associated TREM2 mutations T66M was used as control for reduced cell surface TREM2 expression (see [15])

(I) Quantification of surface bound TREM2 by a cell-based ELISA shows reduced surface expression of p.T66M and p.H157Y TREM2.

(J) TREM2 variant H157Y does not change the position of the ectodomain cleavage site. Graph shows single peak in MALDI-TOF mass spectrometry corresponding to a product cleaved after Y157.

Figure 3:
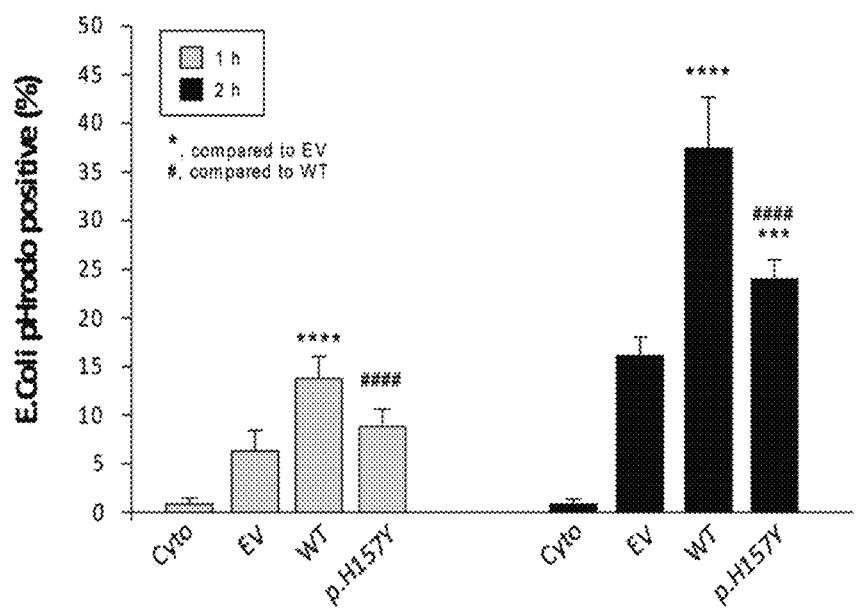

FIG. 3. Impaired phagocytosis in cells expressing TREM2 H157Y variant Phagocytosis of pHrodo *E. coli* in HEK293 Flp-In cells stably expressing TREM2-DAP12 fusion constructs show reduced phagocytic uptake in H157Y expressing cells compared to wild-type (WT) expressing cells after 1h (gray) and 2h (black) of incubation. Cytochalasin D (10 NM) was used as a negative control to inhibit phagocytosis. EV, empty vector control.

FIG. 4. Prediction of secondary structure (s2D method) of amino acids 149-174 of TREM2 (SEQ ID NO: 1) Black line indicates identified cleavage site.

Figure 5:
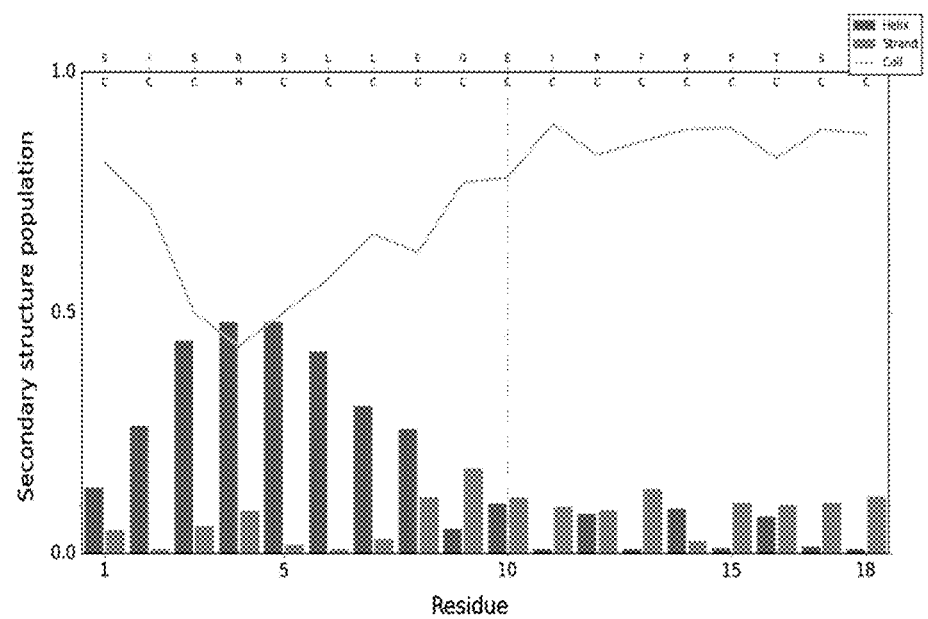

FIG. 5. Prediction of secondary structure (s2D method) of amino acids 158-175 of TREM2 (SEQ ID NO: 1) Amino acid sequence C-terminally of cleavage (=N-terminal part of remaining CTF)

Figure 6:
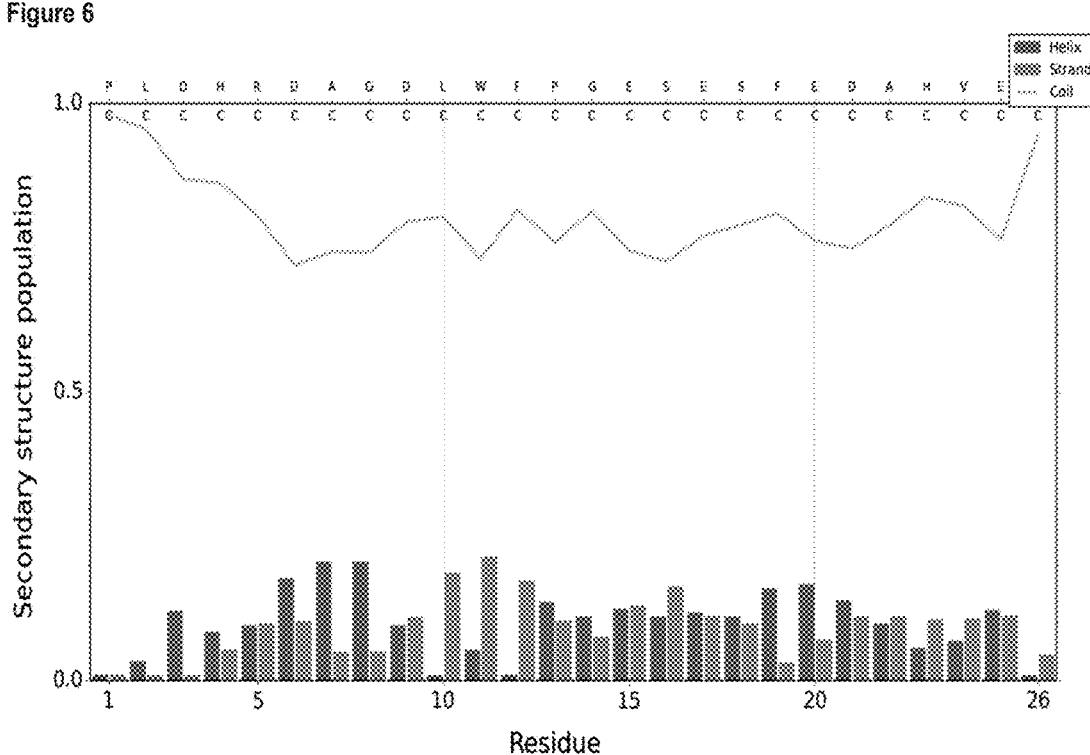

FIG. 6. Prediction of secondary structure (s2D method) of amino acids 132-157 of TREM2 (SEQ ID NO: 1) Amino acid sequence N-terminally of cleavage (=C-terminal part of soluble TREM2)

Figure 7:
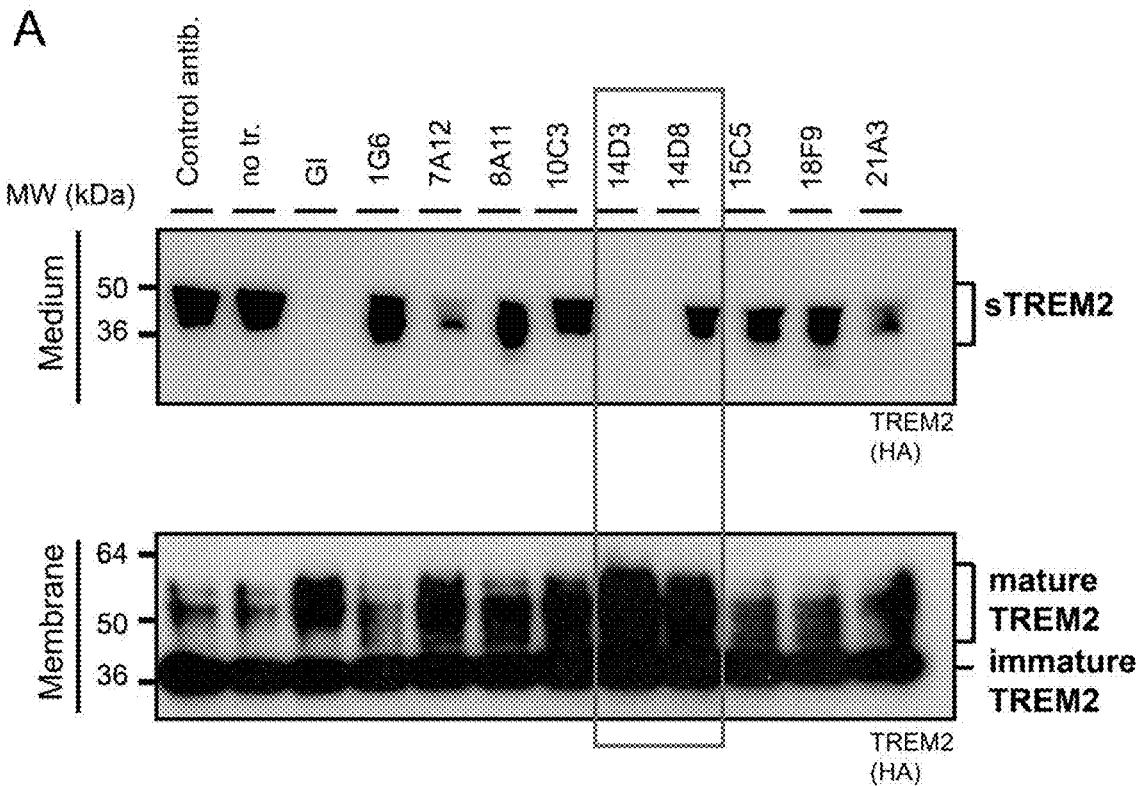
Figure 7:
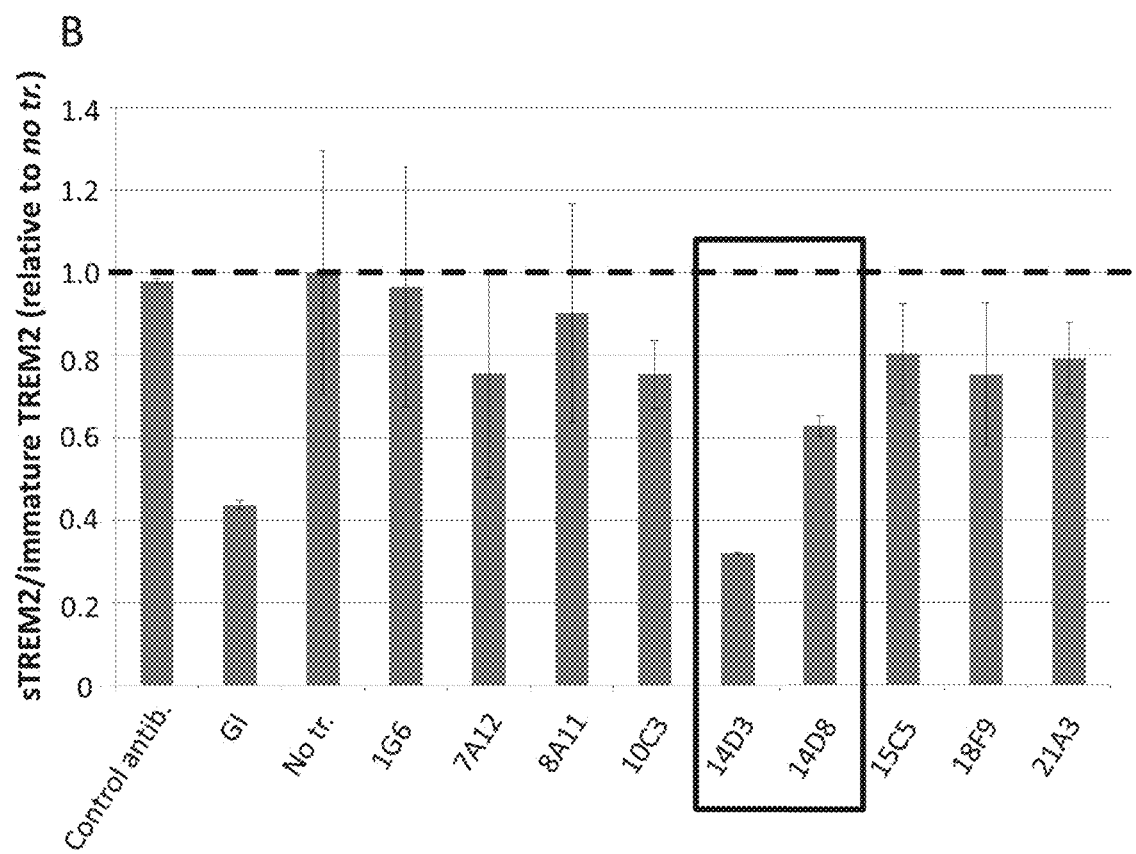
Figure 7:
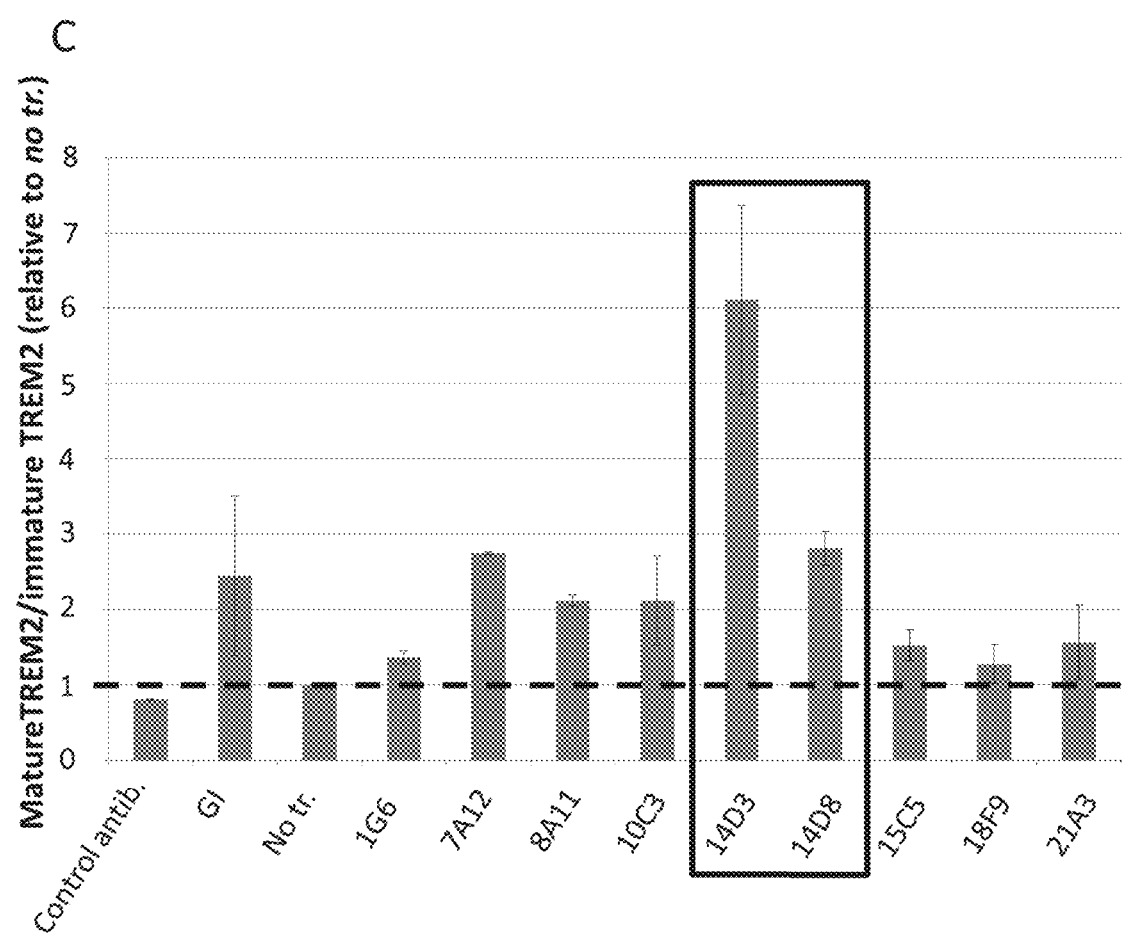

FIG. 7. Inhibition of TREM2 ectodomain shedding using cleavage-site-specific antibodies (A) Anti-HA immunoblotting of soluble TREM2 (sTREM2) from conditioned media and mature/immature TREM2 from membrane fractions of HEK cells stably overexpressing wt TREM2 upon 24 hrs antibody treatment using the indicated clones (50 µg/mL final concentration). Selected antibody clones that most strongly reduce ectodomain shedding are indicated by a grey box. Immunoblots are representative for two independent experiments.

(B) ELISA-mediated quantification of sTREM2 (n=2) shows that selected antibody clones (14D3 and 14D8, boxed in grey) directed against the ectodomain cleavage site lead to decreases in sTREM2 levels comparable to the ADAM10 inhibitor G1254023X (positive control).

(C) Quantitative analysis of immunoblotting of mature TREM2 (n=2) reveals that selected antibody clones (14D3 and 14D8, boxed in grey) result in increases in levels of mature TREM2 comparable to or even higher than the ADAM10 inhibitor G1254023X (positive control).

Levels of sTREM2 and mature TREM2 in FIGS. 7B and C are presented as mean±SEM and were normalized to levels of immature TREM2 as quantified from immunoblots. A monoclonal antibody, which is specific for the C terminus of human TREM2, was used as a negative control. No tr.: no treatment.

Figure 8:
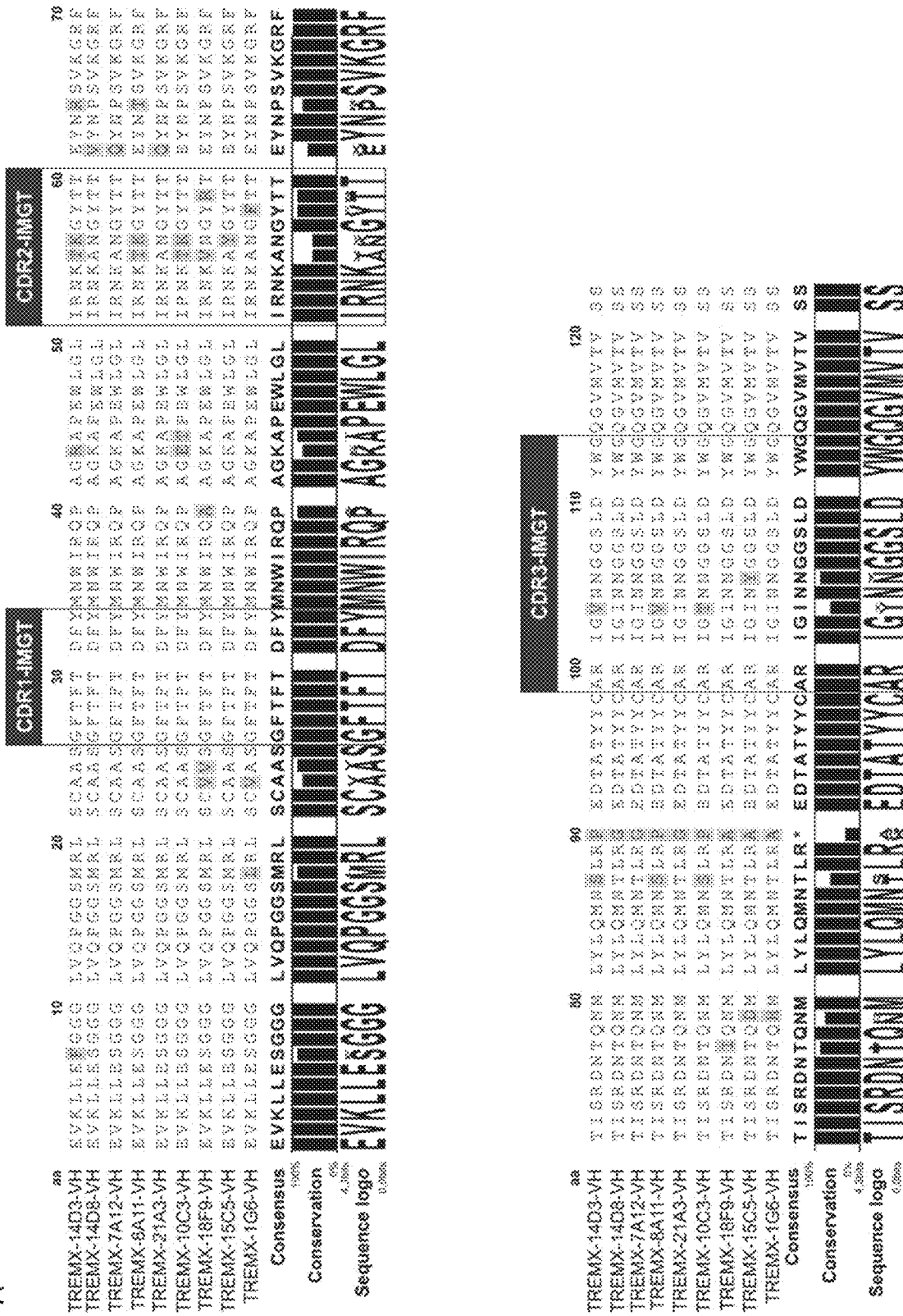
Figure 8:
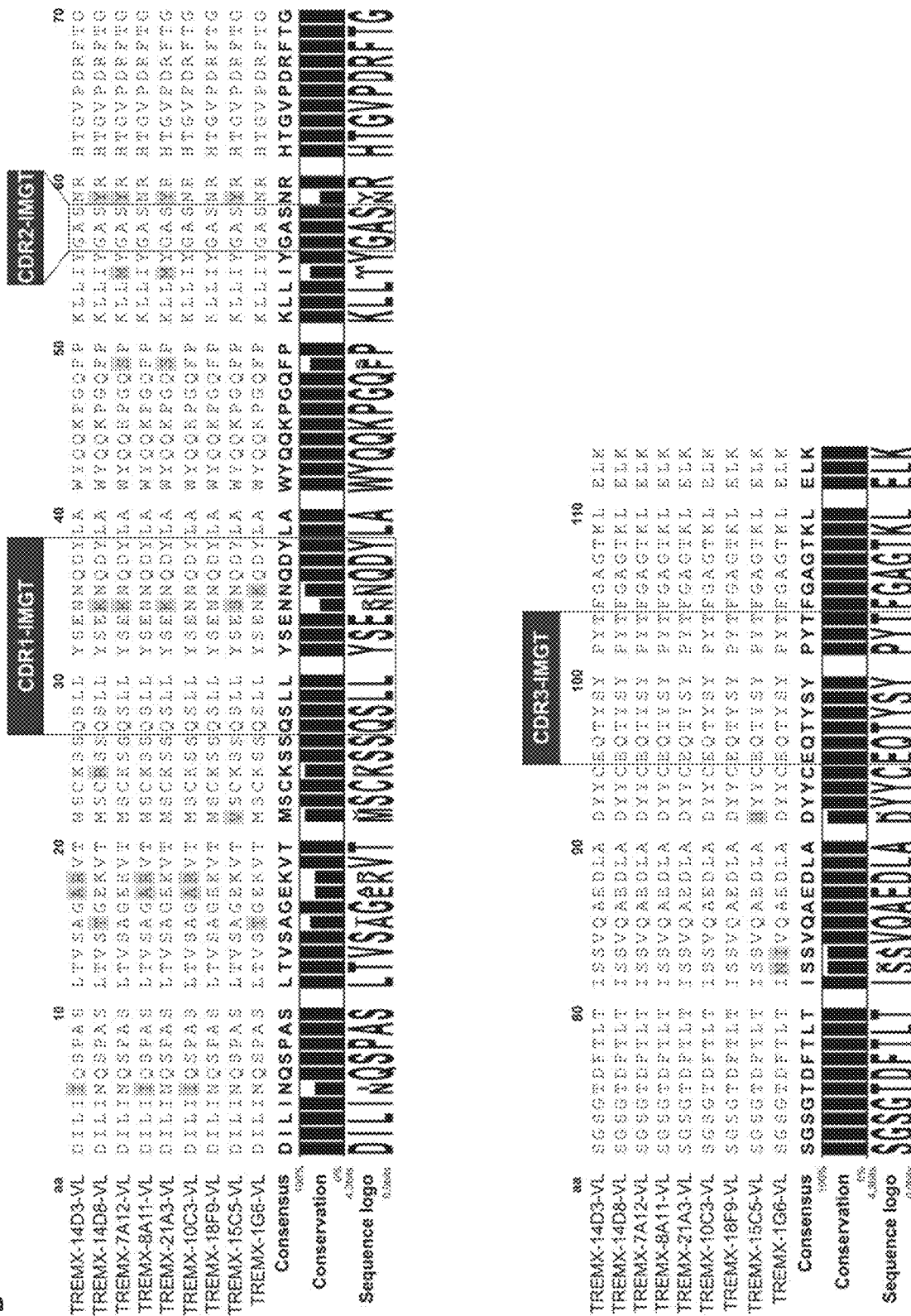

FIG. 8. Alignments of the amino acid sequences from the variable regions of some of the produced antibodies.

(A) Alignment of amino acid sequences (SEQ ID NO:23-32) from the variable heavy chain. CDR regions are boxed. Sequence variations between individual antibody clones are indicated in grey. Amino acid numbers are indicated and CDR determination was performed according to IMGT criteria. Consensus sequence, percent conservation and sequence logo was generated using CLC MAIN workbench 6.9.1. *, position with variations in the amino acid sequence between individual antibody clones.

(B) Alignment of amino acid sequences from the variable light chain (SEQ ID NO:33-42). CDR regions are boxed. Sequence variations between individual antibody clones are indicated in grey. Amino acid numbers are indicated and CDR determination was performed according to IMGT criteria. Consensus sequence, percent conservation and sequence logo was generated using CLC MAIN workbench 6.9.1. *, position with variations in the amino acid sequence between individual antibody clones.

FIG. 9. Amino acid sequences of antibody clones (SEQ ID NO: 23-31 and 33-41) as well as of the respective consensus sequence (SEQ ID NO:32 and SEQ ID NO:42). Bold face uppercase letters indicate that 100% of the compared sequences have the same amino acid at this position. Bold face lowercase letters indicate that >50% of the compared sequences have the same amino acid at this position. Non-bold face uppercase letters indicate that >80% of the compared sequences have the same amino acid at this position. * indicates that no consensus sequence can be determined. Therefore, *can be any amino acid. The CDR sequences are underlined (SEQ ID NO: 43-82 and 93-102).

Table 1.

List of identified peptides and comparison of observed peptide masses to the calculated mass. [M+H]+ indicates a singly charged peptide.

Table 2.

Identified peptide and comparison of observed peptide mass to the calculated mass [M+H]+ indicates a singly charged peptide.

The Examples illustrate the invention.

Example 1: An Alzheimer Associated TREM2 Variant Occurs at the ADAM Cleavage Site and Affects Shedding and Phagocytic Function Materials and Methods
cDNA Constructs The coding sequence of wild-type (WT) human TREM2 was amplified by PCR from a cDNA clone (Clone 693; Holzel Diagnostika, Germany) introducing a HA-tag (YPYDVPDYA (SEQ ID NO:116) followed by the linker sequence SGGGGGLE (SEQ ID NO:117)) located after the endogenous TREM2 signal peptide (aa1-18) and a C-terminal FLAG tag (DYKDDDDK (SEQ ID NO:118)). TREM2 constructs were subcloned into the pcDNA5™/FRT/TO or into the pcDNA3.1/Zeo(+) vector (both Life Technologies) using the restriction enzymes HindIII (New England Biolabs) and XhoI (Thermo Scientific). TREM2-DAP12 fusion constructs for phagocytosis experiments were generated using the Gibson Assembly™ Method (New England BioLabs) using one or two gBlock Gene fragments (Integrated DNA Technologies), respectively, together with the pcDNA5™/FRT/TO vector linearized with the restriction enzymes BamHI and XhoI (Thermo Scientific). TREM2-DAP12 fusion constructs contained the ectodomain of TREM2 including aa169 (Proline169) fused to DAP12 (aa28-113). Furthermore an amino acid change in the transmembrane domain of DAP12 from aspartic acid to alanine (p.D50A) was included. Additionally the TREM2-DAP12 fusion constructs included a HA-tag after the endogenous TREM2 signal peptide as described above. The TREM2 missense mutations p.T66M (ACG>ATG), and p.H157Y (CAC>TAC) were introduced into the respective plasmids by site-directed mutagenesis (Stratagene, La Jolla, Calif.) and all constructs verified by DNA sequencing.

Cell Culture and Generation of Isogenic Cell Lines

Flp-In 293 cells (HEK293 Flp-In; Life Technologies) were cultured in Dulbecco's modified Eagle's medium (DMEM) with Glutamax I, supplemented with 10% (v/v) fetal calf serum (FCS), Zeocin (200 mg/ml), and penicillin/streptomycin (PAA Laboratories). Transfections of complementary DNA (cDNA) constructs were carried out using Lipofectamine 2000 according to the manufacturer's recommendations. For stable overexpression of human TREM2 cDNA constructs, HEK293 Flp-In cells were cotransfected with the TREM2 cDNA constructs and pOG44 (Flp-recombinase expression vector; Life Technologies) and selected using hygromycin B (200 mg/ml). If not stated otherwise, products for cell culture experiments were obtained from Life Technologies.

Antibodies

For immunoblot detection, the following antibodies were used: rat monoclonal anti-HA conjugated to HRP (3F10; 1:2,000; Roche), and rat monoclonal antibody against the C terminus of human TREM2 (1:5, provided by Dr. Kremmer/Dr. Feederle Service Unit Monoclonal Antibodies, from Helmholtz Zentrum Munchen). Secondary antibody was HRP-conjugated goat anti-rat, IgG (1:10,000, Santa Cruz Biotechnology).

Cell Surface Biotinylation

Surface biotinylations were carried out using HEK293 Flp-In cells stably overexpressing TREM2 cDNA constructs grown overnight on poly-L-lysine-coated dishes. Cells were washed three times with cold PBS and incubated for 30 min at RT with PBS containing 0.5 mg/ml EZ-Link sulfo-NHS-LC Biotin (Pierce). Cells were washed three times with PBS and quenched with 50 mM NH4Cl containing 1% bovine serum albumin (BSA) in PBS for 10 min at RT. After additional three washing steps in PBS, cells were harvested in PBS and lysed for 20 min on ice in cell lysis buffer (150 mM NaCl, 50 mM Tris-HCl, pH 7.6, 2 mM EDTA, 1% Triton-X 100) freshly supplemented with protease inhibitor cocktail (Sigma). Protein concentrations were measured using the bicinchoninic acid (BCA) method (Pierce) and equal amounts of protein were subjected to precipitation using Streptavidin sepharose (GE Healthcare) overnight at 4° C. Streptavidin sepharose was washed once with 1 ml of each STEN-NaCl (500 mM NaCl, 50 mM Tris-HCl, pH 7.6, 2 mM EDTA, 0.2% NP-40), STEN-SDS (150 mM NaCl, 50 mM Tris-HCl, pH 7.6, 2 mM EDTA, 0.2% NP-40, 0.1 (w/v) SDS), STEN (150 mM NaCl, 50 mM Tris-HCl, pH 7.6, 2 mM EDTA, 0.2% NP-40) and proteins eluted by boiling in 2× Laemmli sample buffer supplemented with beta mercaptoethanol for 10 min at 95° C. Note that no calnexin reactivity was detected on the immunoblots from streptavidin-precipitated samples confirming the integrity of the cells during the surface biotinylation procedure.

Preparation of Conditioned Media, Cell Lysates, and Immunoblotting

HEK293 Flp-In cells stably overexpressing TREM2 or TREM2-DAP12 cDNA constructs were seeded at a density of $1.5 \times 10^5/cm^2$ and medium changed 48 h post seeding. Conditioned medium was collected after 18-20 h, immediately cooled down on ice, centrifuged at 13,000 rpm for 20 min at 4° C. and supernatants frozen at −20° C. until analysis. Supernatants were directly subjected to standard 15% SDS-PAGE. To prepare membrane fractions, cells were washed twice with ice-cold PBS, resuspended in ice-cold hypotonic buffer (0.01 M Tris, pH 7; 1 mM EDTA; 1 mM EGTA), freshly supplemented with protease inhibitor (Sigma) and incubated on ice for 30 min. After snap freezing in liquid nitrogen and thawing, the disrupted cells were centrifuged at 13,000 rpm for 45 min at 4° C.

The resulting pellet was resuspended in STE lysis buffer (150 mM NaCl, 50 mM Tris-HCl, pH 7.6, 2 mM EDTA, 1% Triton-X 100), incubated for 20 min on ice and clarified by centrifugation at 13,000 rpm for 30 min at 4° C. Protein concentrations were measured using the BCA method, equal amounts of protein were mixed with Laemmli sample buffer, supplemented with beta mercaptoethanol, separated by SDS-PAGE and transferred onto polyvinylidene difluoride membranes (Hybond P; Amersham Biosciences, Aylesbury, UK). Bound antibodies were visualized by corresponding HRP-conjugated secondary antibodies using enhanced chemiluminescence technique (Pierce). Quantification of immunoblots was performed on a LAS-4000 image reader and analyzed using the Multi-Gauge V3.0 software (both Fujifilm Life Science).

Phagocytosis Assay

Phagocytosis of fluorogenic E. coli particles (pHrodo Green, Molecular Probes) was analyzed using HEK293 Flp-In cells stably expressing either wild-type or mutant TREM2-DAP12 fusion constructs. Briefly, cells were plated in 24-well plates at a density of $2 \times 10^5$ (HEK293 Flp-In) cells and cultured for 24 to 48 hours. pHrodo E. coli bioparticles were dissolved in PBS to a concentration of 1 mg/ml, and a total of 50 mg of bioparticles was added per condition and incubated for 60 or 120 min at 37° C. As a negative control, phagocytosis was inhibited with 10 mM cytochalasin D, which was added 30 min before addition of pHrodo E. coli bioparticles. Cells were harvested by trypsinization, washed two times with FACS sample buffer, and analyzed by flow cytometry on a MACSQuant VYB flow cytometer (Miltenyi Biotec). Data analysis was performed using the MACSQuantify software (Miltenyi Biotec).

Cell-Based ELISA

HEK293 Flp-In cells stably expressing either the empty vector (pcDNA5™/FRT/TO) or TREM2 cDNA (wild-type or respective mutants) were seeded in a concentration of 15,000 cells/well on poly-L-Lysine coated 96-well plates. One day post seeding non-specific binding was blocked on ice using 10% BSA in DMEM cell culture medium for 20 min. Surface-exposed TREM2 was stained using HRP-coupled anti-HA (3F10; dilution 1:400) in DMEM supplemented with 5% BSA for 90 min on ice. Unbound antibody was washed away by four washes with DMEM and phosphate buffered saline (PBS) and color reaction started by addition of 100 µg/ml tetramethylbenzidine (TMB) in substrate dilution buffer (0.05M Na2HPO4, 0.025M citric acid, pH=5.5; supplemented with 0.75% H2O2). Color reaction was stopped by addition of 2N H2SO4 and absorbance read at 450 nm using an automated plate reader.

MALDI-TOF Mass Spectrometry Analysis of Ectodomain Cleavage

HEK293 Flp-In cells stably expressing WT and H157Y TREM2 were harvested in PBS. Cell pellets were frozen at −20° C. until use. Cells were lysed in lysis buffer (4% DDM, 0.1% N-octylglucoside, 10 mM Tris-HCl, pH 8.0, 5 mM EDTA, and 140 mM NaCl) containing protease inhibitor mix (Sigma-Aldrich) for 20 min on ice. Following a clarifying spin at 13,000 g for 20 min, supernatants were subjected to a second clarifying spin by centrifugation at 100,000 g for 1 h, and incubated with anti-FLAG M2-agarose (Sigma-Aldrich) overnight by rotation at 4° C. Beads were washed four times with IP/MS buffer (0.1% N-octylglucoside, 10 mM Tris-HCl, pH 8.0, 5 mM EDTA, and 140 mM NaCl) and two times with water. Beads were stored at −20° C. until IP/MS analysis.

The TREM2 WT TEV-FLAG construct was transfected transiently into HEK293 Flp-In cells. Fresh medium was added after 24 hours. After 72 hours, the supernatant was collected and centrifuged to remove cell debris. The pH of the supernatant was adjusted to pH=8.0 using 1 M Tris/HCl, 0.5 M EDTA pH=8.0 was added (3.75 mM final concentration), and the supernatant was incubated anti-FLAG M2-agarose (Sigma-Aldrich) overnight by rotation at 4° C. Beads were washed four times with IP/MS buffer (0.1% N-octylglucoside, 10 mM Tris-HCl, pH 8.0, 5 mM EDTA, and 140 mM NaCl) and two times with water. TREM2 ectodomain was eluted from the beads using 100 mM glycine pH=2.5 and incubating 10 min on ice. Upon centrifugation (5 min at 1,200 g), the supernatant was promptly neutralized by addition of 1/8 volume 1 M Tris/HCl pH=8.0. After addition of EDTA, DTT (final concentrations of 0.5 mM and 1 mM, respectively), and Roche complete protease inhibitor. 10 units of AcTEV (Life Technologies) were added and digestion was carried out overnight at 4° C. Upon addition of 1 mL of IP/MS buffer, anti-FLAG M2-agarose (Sigma-Aldrich) was added and immunoprecipitation was conducted for 1 hour at 4° C. Beads were washed three times with IP/MS buffer (0.1% N-octylglucoside, 10 mM Tris-HCl, pH 8.0, 5 mM EDTA, and 140 mM NaCl) and three times with water. Beads were stored at −20° C. until IP/MS analysis.

IP/MS analysis was performed using Voyager DE STR (Applied Biosystems) as described previously. Immunoprecipitated peptides were eluted with TFA/CH3CN/water (1:20:20) saturated with α-cyano-4-hydroxy cinnamic acid. The dissolved samples were dried on a stainless plate and subjected to MALDI-TOF MS analysis.

Results & Discussion

TREM2 is a type I transmembrane glycoprotein that has recently been linked to an increased risk of developing late-onset Alzheimer's disease. FIG. 1A gives an overview of TREM2 variants that have been reported in the literature thus far. Variants that have been studied biochemically in more detail locate to the Ig-like domain and apparently exert their effect through similar mechanisms (such as Y38C and T66M, Kleinberger et al, 2014). Herein it has been investigated whether variants locating to the stalk region have an impact on ectodomain shedding. It was started to determine the ectodomain cleavage site. In a first experiment, the C-terminal fragment (CTF) that was C-terminally FLAG-tagged was immunoprecipitated. CTF enrichment was accomplished by γ-secretase inhibition using DAPT as an inhibitor. MALDI-TOF mass spectrometry revealed a single prominent peak corresponding to cleavage C-terminal of His157 while mass spectra upon ADAM inhibition using GM and GI inhibitors did not show any peak as expected. (FIG. 1B). In a second independent experiment, a TEV-FLAG site was inserted into the stalk region and short peptides bearing an N-terminal FLAG tag were immunoprecipitated upon TEV digestion. MALDI-TOF mass spectrometry again identified a single prominent peak corresponding to ectodomain cleavage C-terminal of His157 thus confirming the finding from the first experiment (FIG. 1C). Importantly, upon treatment with phorbol 12-myristate 13-acetate (PMA), which leads to activation of additional proteases and accelerated shedding, no major alternative cleavage sites were identified (FIG. 1D). FIG. 1E indicates the location of the ectodomain cleavage site in the stalk region.

Interestingly, among the reported TREM2 variants thus far is one that locates exactly to the cleavage site, i.e., H157Y. The impact of this variant on TREM2 biochemistry and function was therefore analyzed. FIGS. 2A,C show that the variant significantly increases the level of sTREM2. Moreover, western blot quantification of membrane fractions reveals significantly less mature TREM2 as compared to WT levels (FIGS. 2B,D) showing that the increase in ectodomain shedding of variant H157Y is even more pronounced (FIG. 2E). Quantification also reveals about two-fold more immature TREM2 when compared to WT levels (FIG. 2F). Unexpectedly, reduced CTF levels for variant H157Y were observed (FIG. 2G) while shedding is clearly elevated. Protease inhibitor treatment experiments will show whether this observation results from earlier cleavage, i.e, lysosomal CTF degradation. In line with the observed decrease in mature TREM2 levels (FIG. 2D), cell surface biotinylation shows lower levels of membrane-bound full-length TREM2 when compared to WT levels (FIG. 2H). In addition, in a cell-based ELISA, it was again observed significantly decreased levels of membrane-bound TREM2 (FIG. 2I). MALDI-TOF mass spectrometry showed a single prominent peak corresponding to cleavage C-terminal of Y157 upon CTF enrichment using DAPT showing that ectodomain cleavage occurs at exactly the same site as in the WT protein (FIG. 2J). In the following, the functional consequences of reduced levels of membrane-bound full-length TREM2 and increased levels of sTREM2 were investigated in a phagocytosis assay. Uptake of *E. coli* pHrodo revealed significantly impaired phagocytic activity of variant H157Y compared to WT TREM2 (FIG. 3) supporting the notion that full-length membrane-bound TREM2 is required for phagocytosis to take place.

TABLE 1

|  |  | Cleavage |  | Mass (M + H) + (Da) | |
|---|---|---|---|---|---|
|  | Peptide | after | Sequence | Calc. | Obs. |
| Major peptides | TREM2 WT CTF Flag | H157 | SISRSLLEGEIPF . . . DYKDDDDK | 8840.0 | 8837.4 |
|  | Flag-TREM2 (133-157) | H157 | GDYKDDDDK . . . . SFEDAHVEH | 3948.0 | 3949.5 |
|  | TREM2 WT CTF | H157 | SISRSL-LEGEIPF . . . QTLPGLRDT | 7845.1 |  |
| Minor peptides | TREM2 WT CTF Flag | L163 | LEGEIPFPPTSIL . . . DYKDDDDK | 8196.3 | 8193.9 |

TABLE 1-continued

| Peptide | Cleavage after | Sequence | Mass (M + H) + (Da) Calc. | Obs. |
|---|---|---|---|---|
| TREM2 WT CTF Flag | L164 | EGEIPFPPTSILL . . . DYKDDDDK | 8083.1 | 8083.4 |
| TREM2 WT CTE Flag | E165 | GEIPFPPTSILLL . . . DYKDDDDK | 7954.0 | 7948.5 |

TABLE 2

| Peptide | Cleavage after | Sequence | Mass (M + H) + (DA) Calc. | Obs. |
|---|---|---|---|---|
| TREM2 H157Y CTF | Y157 | SISRSLLEGEIPF . . . DYKDDDDK | 8840.0 | 8832.8 |

Example 2: Prediction of Secondary Structure of TREM2 Stalk Region

Materials and Methods

For predicting the secondary structure of the TREM2 stalk region the s2D method as described by P. Sormanni, C. Camilloni, P. Fariselli and M. Vendruscolo was used. In particular, the s2D method is based on simultaneous sequence-based prediction of the statistical populations of ordered and disordered regions in proteins and is described in more detail in Sormanni et al. [76].

Results and Discussion

Prediction of the secondary structure populations in the TREM2 stalk region reveals that this region of the protein exhibits significant proportions of alpha-helical structure, particularly at the C terminus of the cleavage site. Thus, small molecules inhibiting alpha-helix-mediated protein-protein interactions (TREM2-ADAM; TREM2-MMP) may be designed by designing either constraint alpha-helical peptides or proteomimetics that match the topography of an alpha helix by mimicking the spatial orientation of its hot-spot residues, i.e., those residues that are essential for mediating the interaction. Such approaches are known in the art and reviewed, e.g. in Azzarito V et al. [34].

The results of the prediction of the secondary structure of the TREM2 stalk region are shown in FIGS. 4-6. In FIG. 4 the ectodomain cleavage site is indicated by a black vertical line.

Example 3: Antibodies Specific for the TREM2 Cleavage Site Inhibit TREM2 Cleavage Materials and Methods
Generation and Selection of Monoclonal Antibodies Against TREM2 Cleavage Site A peptide comprising amino acids AHVEHSISRS (SEQ ID NO: 7) of human TREM2 Isoform1 was synthesized and coupled at the N-terminus to ovalbumin or biotin (Peps4LS, Heidelberg, Germany). Lou/c rats were immunized subcutaneously (s.c.) and intraperitoneally (i.p.) with a mixture of 50 µg OVA-coupled peptide in 500 µl PBS, 5 nmol CpG2006 (TIB MOLBIOL, Berlin, Germany), and 500 µl incomplete Freund's adjuvant. After 6 weeks, a boost without Freund's adjuvant was given i.p. and s.c. 3 days before fusion. Fusion of the myeloma cell line P3X63-Ag8.653 with the rat immune spleen cells was performed using polyethylene glycol 1500 according to standard procedure (Koehler and Milstein, Nature. 1975, 256:495-497). After fusion, the cells were plated in 96-well plates using RPMI 1640 with 20% fetal calf serum, penicillin/streptomycin, glutamine, pyruvate, and non-essential amino acids supplemented with HAT HybriMax medium supplement (Sigma,). Hybridoma supernatants were tested in an enzyme-linked immunoassay using biotinylated peptides (0.2 µg/ml) bound to avidin-coated plates. After blocking with PBS/2% FCS, hybridoma supernatants were added for 30 min. After one wash with PBS, bound antibodies were detected with a cocktail of HRP-conjugated mAbs against the four rat IgG isotypes. HRP was visualized with ready to use TMB substrate (1-Step™ Ultra TMB-ELISA, Thermo).

TREM2-reactive supernatants were subsequently screened for their ability to detect TREM2 on the cell surface of HEK293 Flp-In cells stably overexpressing human wild-type TREM2 (Kleinberger et al. 2014). HEK293 Flp-In cells either expressing human full-length TREM2 or empty vector (=control) were cultured in 96-well tissue culture plates, washed twice with PBS, blocked with 2% bovine serum albumin (BSA) in PBS and incubated with the respective TREM2-reactive supernatants (diluted 1:2 in blocking buffer) for 60 minutes on ice. Cells were subsequently washed three times with PBS, fixed with 4% paraformaldehyde for 20 min on room temperature and washed three times with PBS. Binding of TREM2-reactive supernatants was visualized using isotype-specific mouse-anti rat secondary antibodies followed by incubation with a goat anti-mouse tertiary antibody coupled to Alexa-488 (Life Technologies). 4', 6-diamidino-2-phenylindol (Dapi, Life Technologies) was used as a nuclear counterstain. Images were acquired automatically using a Cytation multi-detection reader (Biotek).

The hybridoma cells of TREM2-reactive supernatants capable of binding selectively to TREM2 on the cell surface were cloned at least twice by limiting dilution. The IgG subclass was determined by an ELISA assay with mouse anti-rat kappa light chain antibodies as capture and HRP-coupled mouse anti-rat IgG subclass-specific antibodies for detection.

An alignment of amino acid sequences of the variable heavy chain and the variable light chain of some of the produced antibodies is shown in FIG. 8. The corresponding sequences are also shown in FIG. 9.

Treatment of HEK Flp-in Cells Stably Overexpressing Wt TREM2 Using Antibodies Specific for the Ectodomain Cleavage Site $1*10^6$-$1.5*10^6$ cells were seeded in the 6-well format. 24 hours later fresh medium was added to the cells. Antibody clones as generated by Dr. Feederle (Helmholtz Center Munich, Core Facility Monoclonal Antibody Development) were added simultaneously, i.e. for overnight treatment (about 24 hrs), at a final concentration of 50 µg/mL. On the next day, conditioned media and cells were collected and processed as described under "Preparation of conditioned media, cell lysates, and immunoblotting".

ADAM10 inhibitor G1254023X (5 µM final concentration) and a control monoclonal antibody, which is specific for the C terminus of human TREM2, were used as positive and negative controls, respectively.

sTREM2 ELISA

For quantitation of levels of sTREM2 in cell culture supernatants, an ELISA for human sTREM2 was established using the Meso Scale Discovery SECTOR Imager 2400. Streptavidin-coated 96-well plates were blocked overnight at 4° C. in 0.5% bovine serum albumin (BSA) and 0.05% Tween 20 in PBS (pH 7.4) (blocking buffer). For detection of human sTREM2, plates were shaken for 1 hour at room temperature with biotinylated polyclonal goat anti-human TREM2 capture antibody (0.25 mg/ml; R&D Systems) diluted in blocking buffer. Plates were washed subsequently four times with 0.05% Tween 20 in PBS (washing buffer) and incubated for 2 hours at room temperature with samples diluted 1:4 in 0.25% BSA and 0.05% Tween 20 in PBS (pH 7.4) (assay buffer) supplemented with protease inhibitors (Sigma). Recombinant human TREM2 protein (Holzel Diagnostika) was diluted in assay buffer in a two-fold serial dilution and used for the standard curve (concentration range, 4000 to 62.5 µg/ml). Plates were washed three times for 5 min with washing buffer before incubation for 1 hour at room temperature with mouse monoclonal anti-TREM2 antibody (1 mg/ml; Santa Cruz Biotechnology; B-3) diluted in blocking buffer. After three additional washing steps, plates were incubated with a SULFO-TAG-labeled anti-mouse secondary antibody (1:1000; Meso Scale Discovery) and incubated for 1 hour in the dark. Last, plates were washed three times with washing buffer followed by two washing steps in PBS and developed by adding Meso Scale Discovery Read buffer. The light emission at 620 nm after electrochemical stimulation was measured using the Meso Scale Discovery SECTOR Imager 2400 reader. To quantify the levels of sTREM2 secreted from HEK293 Flp-In cells, conditioned media from biological replicates were analyzed in duplicates. The sTREM2 standard curves were generated using the MasterPlex ReaderFit software (MiraiBio Group, Hitachi Solutions America) through a five-parameter logistic fit. Levels of sTREM2 were subsequently normalized to levels of immature TREM2 as quantified from Western Blots.

Results

TREM2 is expressed on the plasma membrane and as such mediates microglial functions such as phagocytosis and chemotaxis. Since extracellular factors promoting phagocytic or chemotactic activity of microglia need to bind to the extracellular domain of TREM2 to initiate downstream intracellular signaling, microglial activity correlates with the level of full-length, i.e., uncleaved, TREM2 on the cell surface. The ectodomain cleavage site has been determined herein and it was reasoned that by generating monoclonal antibodies directed against the cleavage site it would be possible to inhibit ectodomain cleavage and thereby increase the level of full-length TREM2 on the cell surface. This would in turn result in enhanced TREM2-related microglial activity.

As a first step, rats were immunized with a decameric peptide ($^{153}$AHVEHSISRS$^{162}$) (SEQ ID NO: 7) that harbors the cleavage site between histidine 157 and serine 158. In the following, antibody clones were purified from hybridoma supernatants to be able to test different antibody concentrations in cell culture experiments. In particular, HEK cells stably overexpressing wt TREM2 were treated with nine different antibody clones at a final concentration of 50 µg/mL for 24 hours. As a negative control we included a monoclonal antibody, which binds to the C terminus of TREM2 and should therefore not interfere with ectodomain shedding. As a positive control we included the ADAM10 inhibitor G1254023X, which is known to strongly inhibit cleavage (Kleinberger et al, 2014). Conditioned media were collected and subjected to immunoblotting to investigate the influence of the different antibody clones on ectodomain cleavage (FIG. 7A).

Levels of sTREM2 as shown in the top blot of FIG. 7A clearly show that selected antibody clones strongly reduce the extent of ectodomain cleavage. This is particularly evident for clones 14D3 and 14D8 (highlighted with a box). As expected and shown in the bottom blot, inhibition of ectodomain cleavage leads to corresponding increases in levels of mature TREM2 in the membrane fraction, which for clones 14D3 and 14D8 are comparable to if not higher than the increase as seen with the ADAM10 inhibitor G1254023X.

The western blot shows only the result of a single experiment, which is representative for the effects of most of the antibodies. To measure more robust effects of each antibody, we then proceeded with quantification of sTREM2 levels using our previously established sTREM2 ELISA (Kleinberger et al, 2014). FIG. 7B shows ELISA data normalized to immature TREM2 levels as obtained from two independent experiments. In line with our immunoblot observations (FIG. 7A), we identified decreased levels of sTREM2 using antibody clones 14D3 and 14D8. Of note, clone 14D3 decreased shedding by about 70%, while treatment with the ADAM10 inhibitor G1254023X decreased shedding by about 60%. For some of the remaining antibody clones (7A12, 10C3, 15C5, 18F9, and 21A3) we observed a slight trend toward reduced sTREM2 levels, which, however, was less pronounced compared to clones 14D3 and 14D8. As expected, sTREM2 levels in the negative control (control antibody detecting the C terminus of human TREM2) were of the same order as in supernatant of untreated cells.

We also quantitatively analyzed levels of mature TREM2 from immunoblotting. FIG. 7C shows levels of mature TREM2 in the membrane fraction normalized to levels of immature TREM2 as obtained from two independent experiments. In good agreement with the reduction in sTREM2

(FIG. 7B), we identified increases in levels of mature TREM2 in the membrane fraction for antibody clones 14D3 and 14D8. More specifically, clone 14D3, which showed the strongest decrease in sTREM2 exhibited the strongest increase in mature TREM2 in the membrane fraction. Moreover, increased levels of TREM2 in the membrane fraction were additionally detected for clones 7A12, 8A11, and 10C3. As expected, GI treatment under all conditions tested yielded increased levels of mature TREM2.

In summary, it can be concluded that ectodomain shedding can be inhibited using the herein provided antibody clones directed against the ectodomain cleavage site. In particular, clone 14D3 yields decreases in sTREM2 by about 70% while increasing levels of mature TREM2 by up to five-fold. Clone 14D8 gives similar results, which, however, are more moderate compared to clone 14D3.

The present invention refers to the following nucleotide and amino acid sequences:

```
SEQ ID NO: 1: human TREM2, membrane bound
>sp|Q9NZC2-1|TREM2_HUMAN Triggering receptor expressed on myeloid cells 2
OS = Homo sapiens GN = TREM2 PE = 1 SV = 1
MEPLRLLILLFVTELSGAHNTTVFQGVAGQSLQVSCPYDSMKHWGRRKAWCRQLGEKGPCQRVVSTHNLWLLSFLR

RWNGSTAITDDTLGGTLTITLRNLQPHDAGLYQCQSLHGSEADTLRKVLVEVLADPLDHRDAGDLWFPGESESFEDAH

VEHSISRSLLEGEIPFPPTSILLLLACIFLIKILAASALWAAAWHGQKPGTHPPSELDCGHDPGYQLQTLPGLRDT

SEQ ID NO: 2: human TREM2, alternative splice variant (secreted TREM2)
>sP|Q9NZC2-2|TREM2_HUMAN Isoform 2 of Triggering receptor expressed on myeloid
cells 2 OS = Homo sapiens GN = TREM2
MEPLMLILLFVTELSGAHNTTVFQGVAGQSLQVSCPYDSMKHWGRRKAWCRQLGEKGPCQRVVSTHNLWLLSFLR

RWNGSTAITDDTLGGTLTITLRNLQPHDAGLYQCQSLHGSEADTLRKVLVEVLADPLDHRDAGDLWFPGESESFEDAH

VEHSISRAERHVKEDDGRKSPGEVPPGTSPACILATWPPGLLVLLWQETTLPEHCFSWTLEAGTG

SEQ ID NO: 3: human TREM2, alternative splice variant (secreted TREM2)
>sp|Q9NZC2-3|TREM2_HUMAN Isoform 3 of Triggering receptor expressed on myeloid
cells 2 OS = Homo sapiens GN = TREM2
MEPLRLLILLFVTELSGAHNTTVFQGVAGQSLQVSCPYDSMKHWGRRKAWCRQLGEKGPCQRVVSTHNLWLLSFLR

RWNGSTAITDDTLGGTLTITLRNLQPHDAGLYQCQSLHGSEADTLRKVLVEVLADPLDHRDAGDLWFPGESESFEDAH

VEHSISRPSQGSHLPSCLSKEPLGRRNPLPTHFHPSPPGLHLSHQDSSSQRPLGCSLAWTEARDTSTQ

SEQ ID NO: 4: murine TREM2, membrane bound
>sp|Q99NH8|TREM2_MOUSE Triggering receptor expressed on myeloid cells 2
OS = Mus musculus GN = Trem2 PE = 1 SV = 1
MGPLHQFLLLLITALSQALNTTVLQGMAGQSLRVSCTYDALKHWGRRKAWCRQLGEEGPCQRVVSTHGVWLLAFLKK

RNGSTVIADDTLAGTVTITLKNLQAGDAGLYQCQSLRGREAEVLQKVLVEVLEDPLDDQDAGDLWVPEESSSFEGAQV

EHSTSRNQETSFPPTSILLLLACVLLSKFLAASILWAVARGRQKPGTPVVRGLDCGQDAGHQLQILTGPGGT

SEQ ID NO: 5: murine TREM2, alternative splice variant (secreted TREM2)
>sp|Q99NH8-2|TREM2_MOUSE Isoform 2 of Triggering receptor expressed on myeloid
cells 2 OS = Mus musculus GN = Trem2
MGPLHQFLLLLITALSQALNTTVLQGMAGQSLRVSCTYDALKHWGRRKAWCRQLGEEGPCQRVVSTHGVWLLAFLKK

RNGSTVIADDTLAGTVTITLKNLQAGDAGLYQCQSLRGREREVLQKVLVEVLEDPLDDQDAGDLWVPEESSSFEGAQV

EHSTSRQVSSCGSPLAYHLPPLSKESRDLLPTHLHSSPPGLRSPEQVSCSQHPLGCGQGQAEAGNTCGQRAGLWPR

CWAPTSDPHWTRRYVREF

SEQ ID NO: 6: rat TREM2
>tr|D3ZZ89|D3ZZ89_RAT Protein Trem2 OS = Rattus norvegicus GN = Trern2 PE = 4
SV = 1
MEPLHVFVLLLVTELSQALNTTVLQGVAGQSLRVSCTYDALRHWGRRKAWCRQLAEEGPCQRVVSTHGVWLLAFLRK

QNGSTVITDDTLAGTVTITLRNLQAGDAGLYQCQSLRGREAEVLQKVVVEVLEDPLDDQDAGDLWVPEESESFEGAQV

EHSTSSQVSSCGSPLTYHLPPKEPIRKDLLPTHFHSSPPGLCPPEQASYSQHPLGCGQGQAEAGDTCGQWARL

SEQ ID NO: 7: Peptide that has been used for immunization for generating an
antibody against human TREM2
AHVEHSISRS SEQ ID NO: 8: Peptide that has been used for immunization for generating an
antibody against human TREM2
EDAHVEH SEQ ID NO: 9: Peptide that has been used for immunization for generating an
antibody against human TREM2
SISRSL
```

-continued

SEQ ID NO: 10: Peptide that has been used for immunization for generating an
antibody against murine TREM2
AQVEHSTSRN SEQ ID NO: 11: Peptide that has been used for immunization for generating an
antibody against murine TREM2
EGAQVEH SEQ ID NO: 12: Peptide that has been used for immunization for generating an
antibody against murine TREM2
STSRNQ SEQ ID NO: 13: Peptide that has been used for immunization for generating an
antibody against rat TREM2
AQVEHSTSSQ SEQ ID NO: 14: Peptide that has been used for immunization for generating an
antibody against rat TREM2
EGAQVEH SEQ ID NO: 15: Peptide that has been used for immunization for generating an
antibody against rat TREM2
STSSQV SEQ ID NO: 16: Amino acid stretch within human TREM2, wherein the minimal
cleavage site of ADAM10 can be predicted
GESESFEDAHVEHSISRSLLEGEIPFPPTS SEQ ID NO: 17: Ectodomain of human TREM2
MEPLRLLILLFVTELSGAHNTTVFQGVAGQSLQVSCPYDSMKHWGRRKAWCRQLGEKGPCQRVVSTHNLWLLSFLR

RWNGSTAITDDTLGGTLTITLRNLQPHDAGLYQCQSLHGSEADTLRKVLVEVLADPLDHRDAGDLWFPGESESFEDAH

VEHSISRSLLEGEIPFPPTS

SEQ ID NO: 18: Ectodomain of murine TREM2
MGPLHQFLLLLITALSQALNTTVLQGMAGQSLRVSCTYDALKHWGRRKAWCRQLGEEGPCQRVVSTHGVWLLAFLKK

RNGSTVIADDTLAGTVTITLKNLQAGDAGLYQCQSLRGREAEVLQKVLVEVLEDPLDDQDAGDLWVPEESSSFEGAQV

EHSTSRNQETSFPPTS

SEQ ID NO: 19: Intracellular domain of human TREM2
AAWHGQKPGTHPPSELDCGHDPGYGLQTLPGLRDT SEQ ID NO: 20: Intracellular domain of murine TREM2
VARGRQKPGTPVVRGLDCGQDAGHQLQILTGPGGT SEQ ID NO: 21: Peptide that has been used for immunization for generating an
antibody against human TREM2
GESESFEDAHV SEQ ID NO: 22: Peptide that has been used for immunization for generating an
antibody against murine TREM2
EHSTSRNQETSFP Further sequences are shown in FIG. 9.

REFERENCE LIST

1. Przedborski, S., M. Vila, and V. Jackson-Lewis, *Neurodegeneration: what is it and where are we?* J Clin Invest, 2003. 111(1): p. 3-10.
2. Lyman, M., et al., *Neuroinflammation: the role and consequences.* Neurosci Res, 2014. 79: p. 1-12.
3. Villegas-Llerena, C., et al., *Microglial genes regulating neuroinflammation in the progression of Alzheimer's disease.* Curr Opin Neurobiol, 2016. 36: p. 74-81.
4. Klunemann, H. H., et al., *The genetic causes of basal ganglia calcification, dementia, and bone cysts: DAP12 and TREM2.* Neurology, 2005. 64(9): p. 1502-7.
5. Guerreiro, R. J., et al., *Using exome sequencing to reveal mutations in TREM2 presenting as a frontotemporal dementia-like syndrome without bone involvement.* JAMA Neurol, 2013. 70(1): p. 78-84.
6. Borroni, B., et al., *Heterozygous TREM2 mutations in frontotemporal dementia.* Neurobiol Aging, 2014. 35(4): p. 934 e7-10.
7. Cady, J., et al., *TREM2 variant p.R47H as a risk factor for sporadic amyotrophic lateral sclerosis.* JAMA Neurol, 2014. 71(4): p. 449-53.
8. Cuyvers, E., et al., *Investigating the role of rare heterozygous TREM2 variants in Alzheimer's disease and frontotemporal dementia.* Neurobiol Aging, 2014. 35(3): p. 726 e11-9.
9. Guerreiro, R., et al., *TREM2 variants in Alzheimer's disease.* N Engl J Med, 2013. 368(2): p. 117-27.
10. Jonsson, T., et al., *Variant of TREM2 associated with the risk of Alzheimer's disease.* N Engl J Med, 2013. 368(2): p. 107-16.
11. Rayaprolu, S., et al., *TREM2 in neurodegeneration: evidence for association of the p.R47H variant with frontotemporal dementia and Parkinson's disease.* Mol Neurodegener, 2013. 8: p. 19.

12. Colonna, M. and Y. Wang, *TREM2 variants: new keys to decipher Alzheimer disease pathogenesis*. Nat Rev Neurosci, 2016. 17(4): p. 201-7.
13. Ulrich, J. D. and D. M. Holtzman, *TREM2 Function in Alzheimer's Disease and Neurodegeneration*. ACS Chem Neurosci, 2016. 7(4): p. 420-7.
14. Prada, I., et al., *Triggering receptor expressed in myeloid cells 2 (TREM2) trafficking in microglial cells: continuous shuttling to and from the plasma membrane regulated by cell stimulation*. Neuroscience, 2006. 140(4): p. 1139-48.
15. Kleinberger, G., et al., *TREM2 mutations implicated in neurodegeneration impair cell surface transport and phagocytosis*. Sci Transl Med, 2014. 6(243): p. 243ra86.
16. Wunderlich, P., et al., *Sequential proteolytic processing of the triggering receptor expressed on myeloid cells-2 (TREM2) protein by ectodomain shedding and gamma-secretase-dependent intramembranous cleavage*. J Biol Chem, 2013. 288(46): p. 33027-36.
17. Suarez-Calvet, M., et al., *sTREM2 cerebrospinal fluid levels are a potential biomarker for microglia activity in early-stage Alzheimer's disease and associate with neuronal injury markers*. EMBO Mol Med, 2016. 8(5): p. 466-76.
18. Piccio, L., et al., *Cerebrospinal fluid soluble TREM2 is higher in Alzheimer disease and associated with mutation status*. Acta Neuropathol, 2016. 131(6): p. 925-33.
19. Heslegrave, A., et al., *Increased cerebrospinal fluid soluble TREM2 concentration in Alzheimer's disease*. Mol Neurodegener, 2016. 11: p. 3.
20. Glebov, K., et al., *Functional involvement of gamma-secretase in signaling of the triggering receptor expressed on myeloid cells-2 (TREM2)*. J Neuroinflammation, 2016. 13: p. 17.
21. Park, J. S., et al., *Disease-Associated Mutations of TREM2 Alter the Processing of N-Linked Oligosaccharides in the Golgi Apparatus*. Traffic, 2015. 16(5): p. 510-8.
22. Jay, T. R., et al., *TREM2 deficiency eliminates TREM2+ inflammatory macrophages and ameliorates pathology in Alzheimer's disease mouse models*. J Exp Med, 2015. 212(3): p. 287-95.
23. Wang, Y., et al., *TREM2 lipid sensing sustains the microglial response in an Alzheimer's disease model*. Cell, 2015. 160(6): p. 1061-71.
24. Wang, Y., et al., *TREM2-mediated early microglial response limits diffusion and toxicity of amyloid plaques*. J Exp Med, 2016. 213(5): p. 667-75.
25. Yuan, P., et al., *TREM2 Haplodeficiency in Mice and Humans Impairs the Microglia Barrier Function Leading to Decreased Amyloid Compaction and Severe Axonal Dystrophy*. Neuron, 2016. 90(4): p. 724-39.
26. Xiang, X., et al., *TREM2 deficiency reduces the efficacy of immunotherapeutic amyloid clearance*. EMBO Mol Med, 2016.
27. Jin, S. C., et al., *Coding variants in TREM2 increase risk for Alzheimer's disease*. Hum Mol Genet, 2014. 23(21): p. 5838-46.
28. Jin, S. C., et al., *TREM2 is associated with increased risk for Alzheimer's disease in African Americans*. Mol Neurodegener, 2015. 10: p. 19.
29. Jiang, T., et al., *A rare coding variant in TREM2 increases risk for Alzheimer's disease in Han Chinese*. Neurobiol Aging, 2016. 42: p. 217 e1-3.
30. Rubinsztein, D. C., *The roles of intracellular protein-degradation pathways in neurodegeneration*. Nature, 2006. 443(7113): p. 780-6.
31. Bredesen, D. E., R. V. Rao, and P. Mehlen, *Cell death in the nervous system*. Nature, 2006. 443(7113): p. 796-802.
32. Piccio, L., et al., *Identification of soluble TREM-2 in the cerebrospinal fluid and its association with multiple sclerosis and CNS inflammation*. Brain, 2008. 131(Pt 11): p. 3081-91.
33. Heneka, M. T., et al., *NLRP3 is activated in Alzheimer's disease and contributes to pathology in APP/PS1 mice*. Nature, 2013. 493(7434): p. 674-8.
34. Azzarito, V., et al., *Inhibition of alpha-helix-mediated protein-protein interactions using designed molecules*. Nat Chem, 2013. 5(3): p. 161-73.
35. Rissiek, B., F. Koch-Nolte, and T. Magnus, *Nanobodies as modulators of inflammation: potential applications for acute brain injury*. Front Cell Neurosci, 2014. 8: p. 344.
36. Mattsson, N., et al., *CSF protein biomarkers predicting longitudinal reduction of CSF beta-amyloid42 in cognitively healthy elders*. Transl Psychiatry, 2013. 3: p. e293.
37. Bateman, R. J., et al., *Clinical and biomarker changes in dominantly inherited Alzheimer's disease*. N Engl J Med, 2012. 367(9): p. 795-804.
38. WE, P., *Fundamental Immunology, Third Edition*. Third Edition ed, ed. W. E. Paul. 1993: Raven Press, N.Y..
39. Wilson, K. M., et al., *Simplified conjugation chemistry for coupling peptides to F(ab) fragments: autologous red cell agglutination assay for HIV-1 antibodies*. J Immunol Methods, 1994. 175(2): p. 267-73.
40. Yarmush, M. L., X. M. Lu, and D. M. Yarmush, *Coupling of antibody-binding fragments to solid-phase supports: site-directed binding of F(ab')2 fragments*. J Biochem Biophys Methods, 1992. 25(4): p. 285-97.
41. Ward, E. S., et al., *Binding activities of a repertoire of single immunoglobulin variable domains secreted from Escherichia coli*. Nature, 1989. 341(6242): p. 544-6.
42. Harmsen, M. M. and H. J. De Haard, *Properties, production, and applications of camelid single-domain antibody fragments*. Appl Microbiol Biotechnol, 2007. 77(1): p. 13-22.
43. Harlow, *Antibodies, A Laboratory Manual*. 1988: Cold Spring Harbor Publications, New York.
44. Bird, R. E., et al., *Single-chain antigen-binding proteins*. Science, 1988. 242(4877): p. 423-6.
45. Huston, J. S., et al., *Protein engineering of antibody binding sites: recovery of specific activity in an anti-digoxin single-chain Fv analogue produced in Escherichia coli*. Proc Natl Acad Sci USA, 1988. 85(16): p. 5879-83.
46. Pluckthun, *The Pharmacology of Monoclonal Antibodies*. Vol. 113. 1994: Rosenburg and Moore eds. Springer-Verlag, N.Y.
47. Coligan, *Current Protocols in Immunology*. 1991: Wiley/Greene, N.Y.
48. Stites, *Basic and Clinical Immunology*. 7th ed ed.: Lange Medical Publications, Los Altos, Calif. ("Stites".
49. Goding, *Monoclonal Antibodies: Principles and Practice*. 2d ed ed. 1986: Academic Press, New York, N.Y.
50. Kohler, G. and C. Milstein, *Continuous cultures of fused cells secreting antibody of predefined specificity*. Nature, 1975. 256(5517): p. 495-7.
51. Hoogenboom, H. R., *Designing and optimizing library selection strategies for generating high-affinity antibodies*. Trends Biotechnol, 1997. 15(2): p. 62-70.
52. Katz, B. A., *Structural and mechanistic determinants of affinity and specificity of ligands discovered or engineered by phage display*. Annu Rev Biophys Biomol Struct, 1997. 26: p. 27-45.

53. Kozbor, D. and J. C. Roder, *The production of monoclonal antibodies from human lymphocytes.* Immunol Today, 1983. 4(3): p. 72-9.
54. Cole, *Monoclonal Antibodies and Cancer Therapy.* 1985: Alan R. Liss, Inc.
55. Clackson, T., et al., *Making antibody fragments using phage display libraries.* Nature, 1991. 352(6336): p. 624-8.
56. Marks, J. D., et al., *By-passing immunization. Human antibodies from V-gene libraries displayed on phage.* J Mol Biol, 1991. 222(3): p. 581-97.
57. Songsivilai, S. and P. J. Lachmann, *Bispecific antibody: a tool for diagnosis and treatment of disease.* Clin Exp Immunol, 1990. 79(3): p. 315-21.
58. Kostelny, S. A., M. S. Cole, and J. Y. Tso, *Formation of a bispecific antibody by the use of leucine zippers.* J Immunol, 1992. 148(5): p. 1547-53.
59. Holliger, P., T. Prospero, and G. Winter, *"Diabodies": small bivalent and bispecific antibody fragments.* Proc Natl Acad Sci USA, 1993. 90(14): p. 6444-8.
60. Traunecker, A., A. Lanzavecchia, and K. Karjalainen, *Bispecific single chain molecules (Janusins) target cytotoxic lymphocytes on HIV infected cells.* EMBO J, 1991. 10(12): p. 3655-9.
61. Traunecker, A., A. Lanzavecchia, and K. Karjalainen, Janusin: new molecular design for bispecific reagents. Int J Cancer Suppl, 1992. 7: p. 51-2.
62. Jones, P. T., et al., *Replacing the complementarity-determining regions in a human antibody with those from a mouse.* Nature, 1986. 321(6069): p. 522-5.
63. Riechmann, L., et al., *Reshaping human antibodies for therapy.* Nature, 1988. 332(6162): p. 323-7.
64. Presta, L. G., *Antibody engineering.* Curr Opin Biotechnol, 1992. 3(4): p. 394-8.
65. Petering, J., P. McManamny, and J. Honeyman, *Antibody therapeutics—the evolving patent landscape.* N Biotechnol, 2011. 28(5): p. 538-44.
66. Ansel, *Ansel's Pharmaceutical Dosage Forms and Drug Delivery Systems.* 2004: Philadelphia: Lippincott, Williams & Wilkins.
67. Gennaro and Remington, *The Science and Practice of Pharmacy.* 2000: Philadelphia: Lippincott, Williams & Wilkins.
68. Rowe, *Handbook of Pharmaceutical Excipients.* 2005: Chicago, Pharmaceutical Press.
69. Bastin, R., M. Bowker, and B. Slater, *Salt Selection and Optimisation Procedures for Pharmaceutical New Chemical Entities.* Org. Proc. Res. Dev., 2000. 4(5): p. 427-435.
70. Ansel, *Pharmaceutical Dosage Forms and Drug Delivery Systems.* 6th ed. ed. 1995.
71. Thompson, J. D., D. G. Higgins, and T. J. Gibson, *CLUSTAL W: improving the sensitivity of progressive multiple sequence alignment through sequence weighting, position-specific gap penalties and weight matrix choice.* Nucleic Acids Res, 1994. 22(22): p. 4673-80.
72. Brutlag, D. L., et al., *Improved sensitivity of biological sequence database searches.* Comput Appl Biosci, 1990. 6(3): p. 237-45.
73. Altschul, S. F., et al., *Gapped BLAST and PSI-BLAST: a new generation of protein database search programs.* Nucleic Acids Res, 1997. 25(17): p. 3389-402.
74. Altschul, S. F., *A protein alignment scoring system sensitive at all evolutionary distances.* J Mol Evol, 1993. 36(3): p. 290-300.
75. Altschul, S. F., et al., *Basic local alignment search tool.* J Mol Biol, 1990. 215(3): p. 403-10.
76. Sormanni, P., et al., *The s2D method: simultaneous sequence-based prediction of the statistical populations of ordered and disordered regions in proteins.* J Mol Biol, 2015. 427(4): p. 982-96.

---

The invention claimed is:

1. An antibody comprising a heavy chain variable region and a light chain variable region, wherein:
   (a) the heavy chain variable region comprises a sequence having at least 85% sequence identity to SEQ ID NO: 23 and wherein the heavy chain variable region comprises a CDR1 of SEQ ID NO:43, a CDR2 of SEQ ID NO:53, and a CDR3 of SEQ ID NO:63 and the light chain variable region comprises a sequence having at least 85% sequence identity to SEQ ID NO: 33 and wherein the light chain variable region comprises a CDR1 of SEQ ID NO:73, a CDR2 of SEQ ID NO:83, and a CDR3 of SEQ ID NO:93, and wherein the antibody inhibits TREM2 cleavage; or
   (b) the heavy chain variable region comprises a sequence having at least 85% sequence identity to SEQ ID NO: 24 and wherein the heavy chain variable region comprises a CDR1 of SEQ ID NO:44, a CDR2 of SEQ ID NO:54, and a CDR3 of SEQ ID NO:64 and the light chain variable region comprises a sequence having at least 85% sequence identity to SEQ ID NO: 34 and wherein the light chain variable region comprises a CDR1 of SEQ ID NO:74, a CDR2 of SEQ ID NO:84, and a CDR3 of SEQ ID NO:94, and wherein the antibody inhibits TREM2 cleavage.

2. The antibody of claim 1, wherein said antibody comprises SEQ ID NO:23.

3. The antibody of claim 1, wherein said antibody comprises SEQ ID NO:24.

4. The antibody of claim 1, wherein said antibody comprises SEQ ID NO:33.

5. The antibody of claim 1, wherein said antibody comprises SEQ ID NO:34.

6. The antibody of claim 1, wherein said antibody comprises the heavy chain variable region comprises a sequence having at least 85% sequence identity to SEQ ID NO: 23 and wherein the heavy chain variable region comprises a CDR1 of SEQ ID NO:43, a CDR2 of SEQ ID NO:53, and a CDR3 of SEQ ID NO:63 and the light chain variable region comprises a sequence having at least 85% sequence identity to SEQ ID NO: 33 and wherein the light chain variable region comprises a CDR1 of SEQ ID NO:73, a CDR2 of SEQ ID NO:83, and a CDR3 of SEQ ID NO:93, and wherein the antibody inhibits TREM2 cleavage.

7. The antibody of claim 1, wherein said antibody comprises the heavy chain variable region comprises a sequence having at least 90% sequence identity to SEQ ID NO: 23 and wherein the heavy chain variable region comprises a CDR1 of SEQ ID NO:43, a CDR2 of SEQ ID NO:53, and a CDR3 of SEQ ID NO:63 and the light chain variable region comprises a sequence having at least 90% sequence identity to SEQ ID NO: 33 and wherein the light chain variable region comprises a CDR1 of SEQ ID NO:73, a CDR2 of SEQ ID NO:83, and a CDR3 of SEQ ID NO:93, and wherein the antibody inhibits TREM2 cleavage.

8. The antibody of claim 1, wherein said antibody comprises the heavy chain variable region comprises a sequence having at least 95% sequence identity to SEQ ID NO: 23 and wherein the heavy chain variable region comprises a CDR1 of SEQ ID NO:43, a CDR2 of SEQ ID NO:53, and a CDR3 of SEQ ID NO:63 and the light chain variable region comprises a sequence having at least 95% sequence identity to SEQ ID NO: 33 and wherein the light chain variable region comprises a CDR1 of SEQ ID NO:73, a CDR2 of SEQ ID NO:83, and a CDR3 of SEQ ID NO:93, and wherein the antibody inhibits TREM2 cleavage.

9. The antibody of claim 1, wherein said antibody comprises a heavy chain variable region comprising a CDR1 of SEQ ID NO:43, a CDR2 of SEQ ID NO:53, and a CDR3 of SEQ ID NO:63 and the light chain variable region comprises a CDR1 of SEQ ID NO:73, a CDR2 of SEQ ID NO:83, and a CDR3 of SEQ ID NO:93, and wherein the antibody inhibits TREM2 cleavage.

10. The antibody of claim 1, wherein said antibody comprises SEQ ID NO:23 and SEQ ID NO:33.

11. The antibody of claim 1, wherein said the heavy chain variable region comprises a sequence having at least 85% sequence identity to SEQ ID NO: 24 and wherein the heavy chain variable region comprises a CDR1 of SEQ ID NO:44, a CDR2 of SEQ ID NO:54, and a CDR3 of SEQ ID NO:64 and the light chain variable region comprises a sequence having at least 85% sequence identity to SEQ ID NO: 34 and wherein the light chain variable region comprises a CDR1 of SEQ ID NO:74, a CDR2 of SEQ ID NO:84, and a CDR3 of SEQ ID NO:94, and wherein the antibody inhibits TREM2 cleavage.

12. The antibody of claim 1, wherein said the heavy chain variable region comprises a sequence having at least 90% sequence identity to SEQ ID NO: 24 and wherein the heavy chain variable region comprises a CDR1 of SEQ ID NO:44, a CDR2 of SEQ ID NO:54, and a CDR3 of SEQ ID NO:64 and the light chain variable region comprises a sequence having at least 90% sequence identity to SEQ ID NO: 34 and wherein the light chain variable region comprises a CDR1 of SEQ ID NO:74, a CDR2 of SEQ ID NO:84, and a CDR3 of SEQ ID NO:94, and wherein the antibody inhibits TREM2 cleavage.

13. The antibody of claim 1, wherein said the heavy chain variable region comprises a sequence having at least 95% sequence identity to SEQ ID NO: 24 and wherein the heavy chain variable region comprises a CDR1 of SEQ ID NO:44, a CDR2 of SEQ ID NO:54, and a CDR3 of SEQ ID NO:64 and the light chain variable region comprises a sequence having at least 95% sequence identity to SEQ ID NO: 34 and wherein the light chain variable region comprises a CDR1 of SEQ ID NO:74, a CDR2 of SEQ ID NO:84, and a CDR3 of SEQ ID NO:94, and wherein the antibody inhibits TREM2 cleavage.

14. The antibody of claim 1, wherein said the heavy chain variable region comprises a CDR1 of SEQ ID NO:44, a CDR2 of SEQ ID NO:54, and a CDR3 of SEQ ID NO:64 and the light chain variable region comprises a CDR1 of SEQ ID NO:74, a CDR2 of SEQ ID NO:84, and a CDR3 of SEQ ID NO:94, and wherein the antibody inhibits TREM2 cleavage.

15. The antibody of claim 1, wherein said antibody comprises SEQ ID NO:24 and SEQ ID NO:34.

16. The antibody of claim 1, wherein the antibody is:
(i) a monoclonal antibody; and/or
(ii) an antibody selected from the group consisting of a humanized antibody, a rat antibody, a chimeric antibody, and a bispecific antibody; and/or
(iii) an antibody fragment, wherein the antibody fragment may be a nanobody, a Fab fragment, a Fab' fragment, a Fab'-SH fragment, a F(ab')2 fragment, a Fd fragment, a Fv fragment, a scFv fragment, or an isolated complementarity determining region (CDR); and/or an antibody fragment selected from the group consisting of a humanized antibody fragment, and a rat antibody fragment.

17. A pharmaceutical composition comprising
(i) the antibody of claim 1; and
(ii) a pharmaceutically acceptable carrier.

18. The antibody of claim 16, wherein the chimeric antibody comprises framework amino acid sequences derived from a human antibody, a mouse antibody, a rabbit antibody, a hamster antibody, a goat antibody, a guinea pig antibody, a ferret antibody, a chicken antibody, a sheep antibody, or a monkey antibody.

19. The antibody of claim 18, wherein said chimeric antibody is a humanized antibody.

20. The antibody of claim 16, wherein the antibody fragment comprises framework amino acid sequences derived from a human antibody, a mouse antibody, a rabbit antibody, a hamster antibody, a goat antibody, a guinea pig antibody, a ferret antibody, a chicken antibody, a sheep antibody, or a monkey antibody.

21. The antibody of claim 20, wherein said antibody fragment is a humanized antibody.

\* \* \* \* \*

SEQUENCE LISTING

```
<160> NUMBER OF SEQ ID NOS: 118

<210> SEQ ID NO 1
<211> LENGTH: 230
<212> TYPE: PRT
<213> ORGANISM: Homo sapiens

<400> SEQUENCE: 1

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125
```

```
Leu Ala Asp Pro Leu Asp His Arg Asp Ala Gly Asp Leu Trp Phe Pro
            130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
            195                 200                 205

Ser Glu Leu Asp Cys Gly His Asp Pro Gly Tyr Gln Leu Gln Thr Leu
210                 215                 220

Pro Gly Leu Arg Asp Thr
225                 230

<210> SEQ ID NO 2
<211> LENGTH: 219
<212> TYPE: PRT
<213> ORGANISM: Homo sapiens
<220> FEATURE:
<223> OTHER INFORMATION: Isoform 2 (secreted TREM2)

<400> SEQUENCE: 2

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
                20                  25                  30

Gln Val Ser Cys Pro Tyr Asp Ser Met Lys His Trp Gly Arg Arg Lys
            35                  40                  45

Ala Trp Cys Arg Gln Leu Gly Glu Lys Gly Pro Cys Gln Arg Val Val
        50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
            130                 135                 140

Gly Glu Ser Glu Ser Phe Glu Asp Ala His Val Glu His Ser Ile Ser
145                 150                 155                 160

Arg Ala Glu Arg His Val Lys Glu Asp Asp Gly Arg Lys Ser Pro Gly
                165                 170                 175

Glu Val Pro Pro Gly Thr Ser Pro Ala Cys Ile Leu Ala Thr Trp Pro
            180                 185                 190

Pro Gly Leu Leu Val Leu Leu Trp Gln Glu Thr Thr Leu Pro Glu His
        195                 200                 205

Cys Phe Ser Trp Thr Leu Glu Ala Gly Thr Gly
            210                 215

<210> SEQ ID NO 3
<211> LENGTH: 222
<212> TYPE: PRT
<213> ORGANISM: Homo sapiens
<220> FEATURE:
```

<223> OTHER INFORMATION: Isoform 3 (TREM2)

<400> SEQUENCE: 3

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Pro Ser Gln Gly Ser His Leu Pro Ser Cys Leu Ser Lys Glu Pro
                165                 170                 175

Leu Gly Arg Arg Asn Pro Leu Pro Thr His Phe His Pro Ser Pro Pro
            180                 185                 190

Gly Leu His Leu Ser His Gln Asp Ser Ser Ser Gln Arg Pro Leu Gly
        195                 200                 205

Cys Ser Leu Ala Trp Thr Glu Ala Arg Asp Thr Ser Thr Gln
    210                 215                 220
```

<210> SEQ ID NO 4
<211> LENGTH: 227
<212> TYPE: PRT
<213> ORGANISM: Mus musculus

<400> SEQUENCE: 4

```
Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg Arg Lys
        35                  40                  45

Ala Trp Cys Arg Gln Leu Gly Glu Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
            100                 105                 110

Leu Arg Gly Arg Glu Ala Glu Val Leu Gln Lys Val Leu Val Glu Val
        115                 120                 125

Leu Glu Asp Pro Leu Asp Asp Gln Asp Ala Gly Asp Leu Trp Val Pro
```

```
                130                 135                 140
Glu Ser Ser Ser Phe Glu Gly Ala Gln Val Glu His Ser Thr Ser
145                 150                 155                 160

Arg Asn Gln Glu Thr Ser Phe Pro Pro Thr Ser Ile Leu Leu Leu
                165                 170                 175

Ala Cys Val Leu Leu Ser Lys Phe Leu Ala Ala Ser Ile Leu Trp Ala
                180                 185                 190

Val Ala Arg Gly Arg Gln Lys Pro Gly Thr Pro Val Val Arg Gly Leu
                195                 200                 205

Asp Cys Gly Gln Asp Ala Gly His Gln Leu Gln Ile Leu Thr Gly Pro
                210                 215                 220

Gly Gly Thr
225

<210> SEQ ID NO 5
<211> LENGTH: 249
<212> TYPE: PRT
<213> ORGANISM: Mus musculus
<220> FEATURE:
<223> OTHER INFORMATION: Isoform 2 (secreted TREM2)

<400> SEQUENCE: 5

Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
                20                  25                  30

Arg Val Ser Cys Thr Tyr Asp Ala Leu Lys His Trp Gly Arg Arg Lys
                35                  40                  45

Ala Trp Cys Arg Gln Leu Gly Glu Glu Gly Pro Cys Gln Arg Val Val
            50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
                100                 105                 110

Leu Arg Gly Arg Glu Ala Glu Val Leu Gln Lys Val Leu Val Glu Val
                115                 120                 125

Leu Glu Asp Pro Leu Asp Asp Gln Ala Gly Asp Leu Trp Val Pro
                130                 135                 140

Glu Glu Ser Ser Ser Phe Glu Gly Ala Gln Val Glu His Ser Thr Ser
145                 150                 155                 160

Arg Gln Val Ser Ser Cys Gly Ser Pro Leu Ala Tyr His Leu Pro Pro
                165                 170                 175

Leu Ser Lys Glu Ser Arg Asp Leu Leu Pro Thr His Leu His Ser Ser
                180                 185                 190

Pro Pro Gly Leu Arg Ser Pro Glu Gln Val Ser Cys Ser Gln His Pro
                195                 200                 205

Leu Gly Cys Gly Gln Gly Gln Ala Glu Ala Gly Asn Thr Cys Gly Gln
                210                 215                 220

Arg Ala Gly Leu Trp Pro Arg Cys Trp Ala Pro Thr Ser Asp Pro His
225                 230                 235                 240

Trp Thr Arg Arg Tyr Val Arg Glu Phe
                245
```

```
<210> SEQ ID NO 6
<211> LENGTH: 228
<212> TYPE: PRT
<213> ORGANISM: Rattus norvegicus

<400> SEQUENCE: 6

Met Glu Pro Leu His Val Phe Val Leu Leu Val Thr Glu Leu Ser
1               5                   10                  15

Gln Ala Leu Asn Thr Thr Val Leu Gln Gly Val Ala Gly Gln Ser Leu
            20                  25                  30

Arg Val Ser Cys Thr Tyr Asp Ala Leu Arg His Trp Gly Arg Arg Lys
        35                  40                  45

Ala Trp Cys Arg Gln Leu Ala Glu Glu Gly Pro Cys Gln Arg Val Val
    50                  55                  60

Ser Thr His Gly Val Trp Leu Leu Ala Phe Leu Arg Lys Gln Asn Gly
65                  70                  75                  80

Ser Thr Val Ile Thr Asp Asp Thr Leu Ala Gly Thr Val Thr Ile Thr
                85                  90                  95

Leu Arg Asn Leu Gln Ala Gly Asp Ala Gly Leu Tyr Gln Cys Gln Ser
            100                 105                 110

Leu Arg Gly Arg Glu Ala Glu Val Leu Gln Lys Val Val Val Glu Val
        115                 120                 125

Leu Glu Asp Pro Leu Asp Asp Gln Asp Ala Gly Asp Leu Trp Val Pro
    130                 135                 140

Glu Glu Ser Glu Ser Phe Glu Gly Ala Gln Val Glu His Ser Thr Ser
145                 150                 155                 160

Ser Gln Val Ser Ser Cys Gly Ser Pro Leu Thr Tyr His Leu Pro Pro
                165                 170                 175

Lys Glu Pro Ile Arg Lys Asp Leu Leu Pro Thr His Phe His Ser Ser
            180                 185                 190

Pro Pro Gly Leu Cys Pro Pro Glu Gln Ala Ser Tyr Ser Gln His Pro
        195                 200                 205

Leu Gly Cys Gly Gln Gly Gln Ala Glu Ala Gly Asp Thr Cys Gly Gln
    210                 215                 220

Trp Ala Arg Leu
225

<210> SEQ ID NO 7
<211> LENGTH: 10
<212> TYPE: PRT
<213> ORGANISM: Artificial Sequence
<220> FEATURE:
<223> OTHER INFORMATION: Peptide for immunization for generating an
      antibody against human TREM2

<400> SEQUENCE: 7

Ala His Val Glu His Ser Ile Ser Arg Ser
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Peptide for immunization for generating an
      antibod against human TREM2

<400> SEQUENCE: 8

Glu Asp Ala His Val Glu His
1               5
```

<210> SEQ ID NO 9
<211> LENGTH: 6
<212> TYPE: PRT
<213> ORGANISM: Artificial Sequence
<220> FEATURE:
<223> OTHER INFORMATION: Peptide for immunization for generating an
      antibody against human TREM2

<400> SEQUENCE: 9

Ser Ile Ser Arg Ser Leu
1               5

<210> SEQ ID NO 10
<211> LENGTH: 10
<212> TYPE: PRT
<213> ORGANISM: Artificial Sequence
<220> FEATURE:
<223> OTHER INFORMATION: Peptide for immunization for generating an
      antibody against murine TREM2

<400> SEQUENCE: 10

Ala Gln Val Glu His Ser Thr Ser Arg Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Peptide for immunization for generating an
      antibody against murine TREM2

<400> SEQUENCE: 11

Glu Gly Ala Gln Val Glu His
1               5

<210> SEQ ID NO 12
<211> LENGTH: 6
<212> TYPE: PRT
<213> ORGANISM: Artificial Sequence
<220> FEATURE:
<223> OTHER INFORMATION: Peptide for immunization for generating an
      antibody against murine TREM2

<400> SEQUENCE: 12

Ser Thr Ser Arg Asn Gln
1               5

<210> SEQ ID NO 13
<211> LENGTH: 10
<212> TYPE: PRT
<213> ORGANISM: Artificial Sequence
<220> FEATURE:
<223> OTHER INFORMATION: Peptide for immunization for generating an
      antibody against rat TREM2

<400> SEQUENCE: 13

Ala Gln Val Glu His Ser Thr Ser Ser Gln
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Peptide for immunization for generating an
      antibody against rat TREM2

<400> SEQUENCE: 14

Glu Gly Ala Gln Val Glu His
1               5

<210> SEQ ID NO 15
<211> LENGTH: 6
<212> TYPE: PRT
<213> ORGANISM: Artificial Sequence
<220> FEATURE:
<223> OTHER INFORMATION: Peptide for immunization for generating an
      antibody against rat TREM2

<400> SEQUENCE: 15

Ser Thr Ser Ser Gln Val
1               5

<210> SEQ ID NO 16
<211> LENGTH: 30
<212> TYPE: PRT
<213> ORGANISM: Artificial Sequence
<220> FEATURE:
<223> OTHER INFORMATION: Amino acid stretch within human TREM2, wherein
      the minimal cleavage site of ADAM10 can be predicted

<400> SEQUENCE: 16

Gly Glu Ser Glu Ser Phe Glu Asp Ala His Val Glu His Ser Ile Ser
1               5                   10                  15

Arg Ser Leu Leu Glu Gly Glu Ile Pro Phe Pro Pro Thr Ser
            20                  25                  30

<210> SEQ ID NO 17
<211> LENGTH: 174
<212> TYPE: PRT
<213> ORGANISM: Artificial Sequence
<220> FEATURE:
<223> OTHER INFORMATION: Ectodomain of human TREM2

<400> SEQUENCE: 17

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser
                165                 170

<210> SEQ ID NO 18
<211> LENGTH: 171
<212> TYPE: PRT
<213> ORGANISM: Artificial Sequence
<220> FEATURE:
<223> OTHER INFORMATION: Ectodomain of murine TREM2

<400> SEQUENCE: 18

Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg Arg Lys
        35                  40                  45

Ala Trp Cys Arg Gln Leu Gly Glu Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
            100                 105                 110

Leu Arg Gly Arg Glu Ala Glu Val Leu Gln Lys Val Leu Val Glu Val
        115                 120                 125

Leu Glu Asp Pro Leu Asp Asp Gln Asp Ala Gly Asp Leu Trp Val Pro
    130                 135                 140

Glu Glu Ser Ser Ser Phe Glu Gly Ala Gln Val Glu His Ser Thr Ser
145                 150                 155                 160

Arg Asn Gln Glu Thr Ser Phe Pro Pro Thr Ser
                165                 170

<210> SEQ ID NO 19
<211> LENGTH: 35
<212> TYPE: PRT
<213> ORGANISM: Artificial Sequence
<220> FEATURE:
<223> OTHER INFORMATION: Intracellular domain of human TREM2

<400> SEQUENCE: 19

Ala Ala Trp His Gly Gln Lys Pro Gly Thr His Pro Pro Ser Glu Leu
1               5                   10                  15

Asp Cys Gly His Asp Pro Gly Tyr Gln Leu Gln Thr Leu Pro Gly Leu
            20                  25                  30

Arg Asp Thr
        35

<210> SEQ ID NO 20
<211> LENGTH: 35
<212> TYPE: PRT
<213> ORGANISM: Artificial Sequence
<220> FEATURE:
<223> OTHER INFORMATION: Intracellular domain of murine TREM2

<400> SEQUENCE: 20

Val Ala Arg Gly Arg Gln Lys Pro Gly Thr Pro Val Val Arg Gly Leu
1               5                   10                  15

Asp Cys Gly Gln Asp Ala Gly His Gln Leu Gln Ile Leu Thr Gly Pro
            20                  25                  30

Gly Gly Thr
        35

<210> SEQ ID NO 21
<211> LENGTH: 11
<212> TYPE: PRT
<213> ORGANISM: Artificial Sequence
<220> FEATURE:
<223> OTHER INFORMATION: Peptide for immunization for generating an
      antibody against human TREM2

<400> SEQUENCE: 21

Gly Glu Ser Glu Ser Phe Glu Asp Ala His Val
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Peptide for immunization for generating an
      antibody against murine TREM2

<400> SEQUENCE: 22

Glu His Ser Thr Ser Arg Asn Gln Glu Thr Ser Phe Pro
1               5                   10

<210> SEQ ID NO 23
<211> LENGTH: 122
<212> TYPE: PRT
<213> ORGANISM: Artificial Sequence
<220> FEATURE:
<223> OTHER INFORMATION: Clone 14D3 variable region of the heavy chain

<400> SEQUENCE: 23

Glu Val Lys Leu Leu Glu Phe Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Arg Ala Pro Glu Trp Leu
        35                  40                  45

Gly Leu Ile Arg Asn Lys Thr Lys Gly Tyr Thr Thr Glu Tyr Asn Arg
    50                  55                  60

Ser Val Lys Gly Arg Phe Thr Ile Ser Arg Asp Asn Thr Gln Asn Met
65                  70                  75                  80

Leu Tyr Leu Gln Met Asn Ser Leu Arg Pro Glu Asp Thr Ala Thr Tyr
                85                  90                  95

Tyr Cys Ala Arg Ile Gly Val Asn Asn Gly Gly Ser Leu Asp Tyr Trp
            100                 105                 110

Gly Gln Gly Val Met Val Thr Val Ser Ser
        115                 120

<210> SEQ ID NO 24
<211> LENGTH: 122
<212> TYPE: PRT
<213> ORGANISM: Artificial Sequence
<220> FEATURE:
<223> OTHER INFORMATION: Clone 14D8 variable region of the heavy chain

<400> SEQUENCE: 24

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe

```
                  20                  25                  30

Tyr Met Asn Trp Ile Arg Gln Pro Ala Gly Lys Ala Pro Glu Trp Leu
            35                  40                  45

Gly Leu Ile Arg Asn Lys Ala Asn Gly Tyr Thr Thr Val Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Gly Glu Asp Thr Ala Thr Tyr
                85                  90                  95

Tyr Cys Ala Arg Ile Gly Ile Asn Asn Gly Gly Ser Leu Asp Tyr Trp
            100                 105                 110

Gly Gln Gly Val Met Val Thr Val Ser Ser
        115                 120

<210> SEQ ID NO 25
<211> LENGTH: 122
<212> TYPE: PRT
<213> ORGANISM: Artificial Sequence
<220> FEATURE:
<223> OTHER INFORMATION: Clone 7A12 variable region of the heavy chain

<400> SEQUENCE: 25

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
            35                  40                  45

Gly Leu Ile Arg Asn Lys Ala Asn Gly Tyr Thr Thr Gln Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Gly Glu Asp Thr Ala Thr Tyr
                85                  90                  95

Tyr Cys Ala Arg Ile Gly Ile Asn Asn Gly Gly Ser Leu Asp Tyr Trp
            100                 105                 110

Gly Gln Gly Val Met Val Thr Val Ser Ser
        115                 120

<210> SEQ ID NO 26
<211> LENGTH: 122
<212> TYPE: PRT
<213> ORGANISM: Artificial Sequence
<220> FEATURE:
<223> OTHER INFORMATION: Clone 8A11 variable region of the heavy chain

<400> SEQUENCE: 26

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
            35                  40                  45

Gly Leu Ile Arg Asn Lys Thr Lys Gly Tyr Thr Thr Glu Tyr Asn Thr
    50                  55                  60

Ser Val Lys Gly Arg Phe Thr Ile Ser Arg Asp Asn Thr Gln Asn Met
65                  70                  75                  80
```

```
Leu Tyr Leu Gln Met Asn Ser Leu Arg Pro Glu Asp Thr Ala Thr Tyr
                85                  90                  95

Tyr Cys Ala Arg Ile Gly Val Asn Asn Gly Gly Ser Leu Asp Tyr Trp
            100                 105                 110

Gly Gln Gly Val Met Val Thr Val Ser Ser
        115                 120

<210> SEQ ID NO 27
<211> LENGTH: 122
<212> TYPE: PRT
<213> ORGANISM: Artificial Sequence
<220> FEATURE:
<223> OTHER INFORMATION: Clone 21A3 variable region of the heavy chain

<400> SEQUENCE: 27

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Leu Ile Arg Asn Lys Ala Asn Gly Tyr Thr Thr Gln Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Gly Glu Asp Thr Ala Thr Tyr
                85                  90                  95

Tyr Cys Ala Arg Ile Gly Ile Asn Asn Gly Gly Ser Leu Asp Tyr Trp
            100                 105                 110

Gly Gln Gly Val Met Val Thr Val Ser Ser
        115                 120

<210> SEQ ID NO 28
<211> LENGTH: 122
<212> TYPE: PRT
<213> ORGANISM: Artificial Sequence
<220> FEATURE:
<223> OTHER INFORMATION: Clone 10C3 variable region of the heavy chain

<400> SEQUENCE: 28

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Glu Thr Pro Glu Trp Leu
        35                  40                  45

Gly Leu Ile Arg Asn Lys Thr Lys Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Ser Leu Arg Pro Glu Asp Thr Ala Thr Tyr
                85                  90                  95

Tyr Cys Ala Arg Ile Gly Thr Asn Asn Gly Gly Ser Leu Asp Tyr Trp
            100                 105                 110

Gly Gln Gly Val Met Val Thr Val Ser Ser
        115                 120

<210> SEQ ID NO 29
```

```
<211> LENGTH: 122
<212> TYPE: PRT
<213> ORGANISM: Artificial Sequence
<220> FEATURE:
<223> OTHER INFORMATION: Clone 18F9 variable region of the heavy chain

<400> SEQUENCE: 29

Glu Val Lys Leu Leu Glu Ser Gly Gly Gly Leu Val Gln Pro Gly Gly
1               5                   10                  15

Ser Met Arg Leu Ser Cys Val Val Ser Gly Phe Thr Phe Thr Asp Phe
            20                  25                  30

Tyr Met Asn Trp Ile Arg Gln Ala Ala Gly Lys Ala Pro Glu Trp Leu
        35                  40                  45

Gly Leu Ile Arg Asn Lys Val Asn Gly Tyr Arg Thr Glu Tyr Asn Pro
    50                  55                  60

Ser Val Lys Gly Arg Phe Thr Ile Ser Arg Asp Asn Ile Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Ile Gly Ile Asn Asn Gly Gly Ser Leu Asp Tyr Trp
            100                 105                 110

Gly Gln Gly Val Met Val Thr Val Ser Ser
        115                 120

<210> SEQ ID NO 30
<211> LENGTH: 122
<212> TYPE: PRT
<213> ORGANISM: Artificial Sequence
<220> FEATURE:
<223> OTHER INFORMATION: Clone 15C5 variable region of the heavy chain

<400> SEQUENCE: 30

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Leu Ile Arg Asn Lys Ala Tyr Gly Tyr Thr Thr Glu Tyr Asn Pro
    50                  55                  60

Ser Val Lys Gly Arg Phe Thr Ile Ser Arg Asp Asn Thr Gln Asp Met
65                  70                  75                  80

Leu Tyr Leu Gln Met Asn Thr Leu Arg Ala Glu Asp Thr Ala Thr Tyr
                85                  90                  95

Tyr Cys Ala Arg Ile Gly Ile Asn Tyr Gly Gly Ser Leu Asp Tyr Trp
            100                 105                 110

Gly Gln Gly Val Met Val Thr Val Ser Ser
        115                 120

<210> SEQ ID NO 31
<211> LENGTH: 122
<212> TYPE: PRT
<213> ORGANISM: Artificial Sequence
<220> FEATURE:
<223> OTHER INFORMATION: Clone 1G6 variable region of the heavy chain

<400> SEQUENCE: 31

Glu Val Lys Leu Leu Glu Ser Gly Gly Gly Leu Val Gln Pro Gly Gly
1               5                   10                  15
```

Ser Leu Arg Leu Ser Cys Val Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Leu Ile Arg Asn Lys Ala Asn Gly Phe Thr Thr Glu Tyr Asn Pro
    50                  55                  60

Ser Val Lys Gly Arg Phe Thr Ile Ser Arg Asp Asn Thr Gln His Met
65                  70                  75                  80

Leu Tyr Leu Gln Met Asn Thr Leu Arg Ala Glu Asp Thr Ala Thr Tyr
                85                  90                  95

Tyr Cys Ala Arg Ile Gly Ile Asn Asn Gly Gly Ser Leu Asp Tyr Trp
            100                 105                 110

Gly Gln Gly Val Met Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: Consensus sequence

<400> SEQUENCE: 32

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Leu Ile Arg Asn Lys Ala Asn Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Glu Asp Thr Ala Thr Tyr Tyr
                85                  90                  95

Cys Ala Arg Ile Gly Ile Asn Asn Gly Gly Ser Leu Asp Tyr Trp Gly
            100                 105                 110

Gln Gly Val Met Val Thr Val Ser Ser
        115                 120

<210> SEQ ID NO 33
<211> LENGTH: 113
<212> TYPE: PRT
<213> ORGANISM: Artificial Sequence
<220> FEATURE:
<223> OTHER INFORMATION: Clone 14D3 variable region of the light chain

<400> SEQUENCE: 33

Asp Ile Leu Ile Ile Gln Ser Pro Ala Ser Leu Thr Val Ser Ala Gly
1               5                   10                  15

Ala Arg Val Thr Met Ser Cys Lys Ser Ser Gln Ser Leu Leu Tyr Ser
            20                  25                  30

Glu Asn Asn Gln Asp Tyr Leu Ala Trp Tyr Gln Gln Lys Pro Gly Gln
        35                  40                  45

Phe Pro Lys Leu Leu Ile Tyr Gly Ala Ser Asn Arg His Thr Gly Val
    50                  55                  60

Pro Asp Arg Phe Thr Gly Ser Gly Ser Gly Thr Asp Phe Thr Leu Thr
65                  70                  75                  80

```
Ile Ser Ser Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 34
<211> LENGTH: 113
<212> TYPE: PRT
<213> ORGANISM: Artificial Sequence
<220> FEATURE:
<223> OTHER INFORMATION: Clone 14D8 variable region of the light chain

<400> SEQUENCE: 34

Asp Ile Leu Ile Asn Gln Ser Pro Ala Ser Leu Thr Val Ser Thr Gly
1               5                   10                  15

Glu Lys Val Thr Met Ser Cys Arg Ser Ser Gln Ser Leu Leu Tyr Ser
            20                  25                  30

Glu Lys Asn Gln Asp Tyr Leu Ala Trp Tyr Gln Gln Lys Pro Gly Gln
        35                  40                  45

Phe Pro Lys Leu Leu Ile Tyr Gly Ala Ser Tyr Arg His Thr Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 35
<211> LENGTH: 113
<212> TYPE: PRT
<213> ORGANISM: Artificial Sequence
<220> FEATURE:
<223> OTHER INFORMATION: Clone 7A12 variable region of the light chain

<400> SEQUENCE: 35

Asp Ile Leu Ile Asn Gln Ser Pro Ala Ser Leu Thr Val Ser Ala Gly
1               5                   10                  15

Glu Lys Val Thr Met Ser Cys Lys Ser Ser Gln Ser Leu Leu Tyr Ser
            20                  25                  30

Glu Lys Asn Gln Asp Tyr Leu Ala Trp Tyr Gln Gln Lys Pro Gly Gln
        35                  40                  45

Ser Pro Lys Leu Leu Met Tyr Gly Ala Ser Tyr Arg His Thr Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 36
<211> LENGTH: 113
<212> TYPE: PRT
```

<213> ORGANISM: Artificial Sequence
<220> FEATURE:
<223> OTHER INFORMATION: Clone 8A11 variable region of the light chain

<400> SEQUENCE: 36

Asp Ile Leu Ile Ile Gln Ser Pro Ala Ser Leu Thr Val Ser Ala Gly
1               5                   10                  15

Ala Arg Val Thr Met Ser Cys Lys Ser Gln Ser Leu Leu Tyr Ser
            20                  25                  30

Glu Asn Asn Gln Asp Tyr Leu Ala Trp Tyr Gln Gln Lys Pro Gly Gln
        35                  40                  45

Phe Pro Lys Leu Leu Ile Tyr Gly Ala Ser Asn Arg His Thr Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 37
<211> LENGTH: 113
<212> TYPE: PRT
<213> ORGANISM: Artificial Sequence
<220> FEATURE:
<223> OTHER INFORMATION: Clone 21A3 variable region of the light chain

<400> SEQUENCE: 37

Asp Ile Leu Ile Asn Gln Ser Pro Ala Ser Leu Thr Val Ser Ala Gly
1               5                   10                  15

Glu Lys Val Thr Met Ser Cys Lys Ser Gln Ser Leu Leu Tyr Ser
            20                  25                  30

Glu Lys Asn Gln Asp Tyr Leu Ala Trp Tyr Gln Gln Lys Pro Gly Gln
        35                  40                  45

Ser Pro Lys Leu Leu Met Tyr Gly Ala Ser Tyr Arg His Thr Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 38
<211> LENGTH: 113
<212> TYPE: PRT
<213> ORGANISM: Artificial Sequence
<220> FEATURE:
<223> OTHER INFORMATION: Clone 10C3 variable region of the light chain

<400> SEQUENCE: 38

Asp Ile Leu Ile Ile Gln Ser Pro Ala Ser Leu Thr Val Ser Ala Gly
1               5                   10                  15

Ala Arg Val Thr Met Ser Cys Lys Ser Gln Ser Leu Leu Tyr Ser
            20                  25                  30

Glu Asn Asn Gln Asp Tyr Leu Ala Trp Tyr Gln Gln Lys Pro Gly Gln

```
                35                  40                  45

Phe Pro Lys Leu Leu Ile Tyr Gly Ala Ser Asn Arg His Thr Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Asp Tyr Tyr Cys Glu Gln
                 85                  90                  95

Thr Tyr Ser Tyr Pro Tyr Thr Phe Gly Ala Gly Thr Lys Leu Glu Leu
            100                 105                 110

Lys

<210> SEQ ID NO 39
<211> LENGTH: 113
<212> TYPE: PRT
<213> ORGANISM: Artificial Sequence
<220> FEATURE:
<223> OTHER INFORMATION: Clone 18F9 variable chain of the light region

<400> SEQUENCE: 39

Asp Ile Leu Ile Asn Gln Ser Pro Ala Ser Leu Thr Val Ser Ala Gly
  1               5                  10                  15

Glu Lys Val Thr Met Ser Cys Lys Ser Ser Gln Ser Leu Leu Tyr Ser
                 20                  25                  30

Glu Asn Asn Gln Asp Tyr Leu Ala Trp Tyr Gln Gln Lys Pro Gly Gln
             35                  40                  45

Phe Pro Lys Leu Leu Ile Tyr Gly Ala Ser Asn Arg His Thr Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Asp Tyr Tyr Cys Glu Gln
                 85                  90                  95

Thr Tyr Ser Tyr Pro Tyr Thr Phe Gly Ala Gly Thr Lys Leu Glu Leu
            100                 105                 110

Lys

<210> SEQ ID NO 40
<211> LENGTH: 113
<212> TYPE: PRT
<213> ORGANISM: Artificial Sequence
<220> FEATURE:
<223> OTHER INFORMATION: Clone 15C5 variable region of the light chain

<400> SEQUENCE: 40

Asp Ile Leu Ile Asn Gln Ser Pro Ala Ser Leu Thr Val Ser Ala Gly
  1               5                  10                  15

Glu Lys Val Thr Val Ser Cys Lys Ser Ser Gln Ser Leu Leu Tyr Ser
                 20                  25                  30

Glu Ser Asn Gln Asp Tyr Leu Ala Trp Tyr Gln Gln Lys Pro Gly Gln
             35                  40                  45

Phe Pro Lys Leu Leu Ile Tyr Gly Ala Ser Tyr Arg His Thr Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala His Tyr Tyr Cys Glu Gln
                 85                  90                  95

Thr Tyr Ser Tyr Pro Tyr Thr Phe Gly Ala Gly Thr Lys Leu Glu Leu
            100                 105                 110
```

Lys

<210> SEQ ID NO 41
<211> LENGTH: 113
<212> TYPE: PRT
<213> ORGANISM: Artificial Sequence
<220> FEATURE:
<223> OTHER INFORMATION: Clone 1G6 variable region of the light chain

<400> SEQUENCE: 41

Asp Ile Leu Ile Asn Gln Ser Pro Ala Ser Leu Thr Val Ser Thr Gly
1               5                   10                  15

Glu Lys Val Thr Met Ser Cys Lys Ser Ser Gln Ser Leu Leu Tyr Ser
            20                  25                  30

Glu Asn Lys Gln Asp Tyr Leu Ala Trp Tyr Gln Gln Lys Pro Gly Gln
        35                  40                  45

Phe Pro Lys Leu Leu Ile Tyr Gly Ala Ser Asn Arg His Thr Gly Val
    50                  55                  60

Pro Asp Arg Phe Thr Gly Ser Gly Ser Gly Thr Asp Phe Thr Leu Thr
65                  70                  75                  80

Ile Asn Ile Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 42
<211> LENGTH: 113
<212> TYPE: PRT
<213> ORGANISM: Artificial Sequence
<220> FEATURE:
<223> OTHER INFORMATION: Consensus sequence

<400> SEQUENCE: 42

Asp Ile Leu Ile Asn Gln Ser Pro Ala Ser Leu Thr Val Ser Ala Gly
1               5                   10                  15

Glu Lys Val Thr Met Ser Cys Lys Ser Ser Gln Ser Leu Leu Tyr Ser
            20                  25                  30

Glu Asn Asn Gln Asp Tyr Leu Ala Trp Tyr Gln Gln Lys Pro Gly Gln
        35                  40                  45

Phe Pro Lys Leu Leu Ile Tyr Gly Ala Ser Asn Arg His Thr Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Asp Tyr Tyr Cys Glu Gln
                85                  90                  95

Thr Tyr Ser Tyr Pro Tyr Thr Phe Gly Ala Gly Thr Lys Leu Glu Leu
            100                 105                 110

Lys

<210> SEQ ID NO 43
<211> LENGTH: 8
<212> TYPE: PRT
<213> ORGANISM: Artificial Sequence
<220> FEATURE:
<223> OTHER INFORMATION: Clone 14D3 CDR1 of the heavy chain

<400> SEQUENCE: 43

Gly Phe Thr Phe Thr Asp Phe Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Clone 14D8 CDR1 of the heavy chain

<400> SEQUENCE: 44

Gly Phe Thr Phe Thr Asp Phe Tyr
1               5

<210> SEQ ID NO 45
<211> LENGTH: 8
<212> TYPE: PRT
<213> ORGANISM: Artificial Sequence
<220> FEATURE:
<223> OTHER INFORMATION: Clone 7A12 CDR1 of the heavy chain

<400> SEQUENCE: 45

Gly Phe Thr Phe Thr Asp Phe Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Clone 8A11 CDR1 of the heavy chain

<400> SEQUENCE: 46

Gly Phe Thr Phe Thr Asp Phe Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: Clone 21A3 CDR1 of the heavy chain

<400> SEQUENCE: 47

Gly Phe Thr Phe Thr Asp Phe Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: Clone 10C3 CDR1 of the heavy chain

<400> SEQUENCE: 48

Gly Phe Thr Phe Thr Asp Phe Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: Clone 18F9 CDR1 of the heavy chain

<400> SEQUENCE: 49

Gly Phe Thr Phe Thr Asp Phe Tyr

```
1               5

<210> SEQ ID NO 50
<211> LENGTH: 8
<212> TYPE: PRT
<213> ORGANISM: Artificial Sequence
<220> FEATURE:
<223> OTHER INFORMATION: Clone 15C5 CDR1

<400> SEQUENCE: 50

Gly Phe Thr Phe Thr Asp Phe Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: Clone 1G6 CDR1 of the heavy chain

<400> SEQUENCE: 51

Gly Phe Thr Phe Thr Asp Phe Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Consensus Sequence CDR1 of the heavy chain

<400> SEQUENCE: 52

Gly Phe Thr Phe Thr Asp Phe Tyr
1               5

<210> SEQ ID NO 53
<211> LENGTH: 10
<212> TYPE: PRT
<213> ORGANISM: Artificial Sequence
<220> FEATURE:
<223> OTHER INFORMATION: Clone 14D3 CDR2 of the heavy chain

<400> SEQUENCE: 53

Ile Arg Asn Lys Thr Lys Gly Tyr Thr Thr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Clone 14D8 CDR2 of the heavy chain

<400> SEQUENCE: 54

Ile Arg Asn Lys Ala Asn Gly Tyr Thr Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Clone 7A12 CDR2

<400> SEQUENCE: 55

Ile Arg Asn Lys Ala Asn Gly Tyr Thr Thr
1               5                   10
```

<210> SEQ ID NO 56
<211> LENGTH: 10
<212> TYPE: PRT
<213> ORGANISM: Artificial Sequence
<220> FEATURE:
<223> OTHER INFORMATION: Clone 8A11 CDR2 of the heavy chain

<400> SEQUENCE: 56

Ile Arg Asn Lys Thr Lys Gly Tyr Thr Thr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Clone 21A3 CDR2 of the heavy chain

<400> SEQUENCE: 57

Ile Arg Asn Lys Ala Asn Gly Tyr Thr Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Clone 10C3 CDR2 of the heavy chain

<400> SEQUENCE: 58

Ile Arg Asn Lys Thr Lys Gly Tyr Thr Thr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Clone 18F9 CDR2 of the heavy chain

<400> SEQUENCE: 59

Ile Arg Asn Lys Val Asn Gly Tyr Arg Thr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Clone 15C5 CDR2 of the heavy chain

<400> SEQUENCE: 60

Ile Arg Asn Lys Ala Tyr Gly Tyr Thr Thr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Clone 1G6 CDR2 of the heavy chain

<400> SEQUENCE: 61

Ile Arg Asn Lys Ala Asn Gly Phe Thr Thr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Consensus Sequence CDR2 of the heavy chain

<400> SEQUENCE: 62

Ile Arg Asn Lys Ala Asn Gly Tyr Thr Thr
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Clone 14D3 CDR3 of the heavy chain

<400> SEQUENCE: 63

Ala Arg Ile Gly Val Asn Asn Gly Gly Ser Leu Asp Tyr Trp Gly
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Clone 14D8 CDR3 of the heavy chain

<400> SEQUENCE: 64

Ala Arg Ile Gly Ile Asn Asn Gly Gly Ser Leu Asp Tyr Trp Gly
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Clone 7A12 CDR3 of the heavy chain

<400> SEQUENCE: 65

Ala Arg Ile Gly Ile Asn Asn Gly Gly Ser Leu Asp Tyr Trp Gly
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Clone 8A11 CDR3 of the heavy chain

<400> SEQUENCE: 66

Ala Arg Ile Gly Val Asn Asn Gly Gly Ser Leu Asp Tyr Trp Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Clone 21A3 CDR3 of the heavy chain

<400> SEQUENCE: 67

Ala Arg Ile Gly Ile Asn Asn Gly Gly Ser Leu Asp Tyr Trp Gly
1               5                   10                  15

```
<210> SEQ ID NO 68
<211> LENGTH: 15
<212> TYPE: PRT
<213> ORGANISM: Artificial Sequence
<220> FEATURE:
<223> OTHER INFORMATION: Clone 10C3 CDR3 of the heavy chain

<400> SEQUENCE: 68

Ala Arg Ile Gly Thr Asn Asn Gly Gly Ser Leu Asp Tyr Trp Gly
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Clone 18F9 CDR3 of the heavy chain

<400> SEQUENCE: 69

Ala Arg Ile Gly Ile Asn Asn Gly Gly Ser Leu Asp Tyr Trp Gly
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Clone 15C5 CDR3 of the heavy chain

<400> SEQUENCE: 70

Ala Arg Ile Gly Ile Asn Tyr Gly Gly Ser Leu Asp Tyr Trp Gly
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Clone 1G6 CDR3 of the heavy chain

<400> SEQUENCE: 71

Ala Arg Ile Gly Ile Asn Asn Gly Gly Ser Leu Asp Tyr Trp Gly
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Consensus Sequence CDR3 of the heavy chain

<400> SEQUENCE: 72

Ala Arg Ile Gly Ile Asn Asn Gly Gly Ser Leu Asp Tyr Trp Gly
1               5                   10                  15

<210> SEQ ID NO 73
<211> LENGTH: 12
<212> TYPE: PRT
<213> ORGANISM: Artificial Sequence
<220> FEATURE:
<223> OTHER INFORMATION: Clone 14D3 CDR1 of the light chain

<400> SEQUENCE: 73

Gln Ser Leu Leu Tyr Ser Glu Asn Asn Gln Asp Tyr
1               5                   10

<210> SEQ ID NO 74
```

```
<211> LENGTH: 12
<212> TYPE: PRT
<213> ORGANISM: Artificial Sequence
<220> FEATURE:
<223> OTHER INFORMATION: Clone 14D8 CDR1 of the light chain

<400> SEQUENCE: 74

Gln Ser Leu Leu Tyr Ser Glu Lys Asn Gln Asp Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Clone 7A12 CDR1 of the light chain

<400> SEQUENCE: 75

Gln Ser Leu Leu Tyr Ser Glu Lys Asn Gln Asp Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Clone 8A11 CDR1 of the light chain

<400> SEQUENCE: 76

Gln Ser Leu Leu Tyr Ser Glu Asn Asn Gln Asp Tyr
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Clone 21A3 CDR1 of the light chain

<400> SEQUENCE: 77

Gln Ser Leu Leu Tyr Ser Glu Lys Asn Gln Asp Tyr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Clone 10C3 CDR1 of the light chain

<400> SEQUENCE: 78

Gln Ser Leu Leu Tyr Ser Glu Asn Asn Gln Asp Tyr
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Clone 18F9 CDR1 of the light chain

<400> SEQUENCE: 79

Gln Ser Leu Leu Tyr Ser Glu Asn Asn Gln Asp Tyr
1               5                   10

<210> SEQ ID NO 80
<211> LENGTH: 12
```

```
<212> TYPE: PRT
<213> ORGANISM: Artificial Sequence
<220> FEATURE:
<223> OTHER INFORMATION: Clone 15C5 CDR1 of the light chain

<400> SEQUENCE: 80

Gln Ser Leu Leu Tyr Ser Glu Ser Asn Gln Asp Tyr
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Clone 1G6 CDR1 of the light chain

<400> SEQUENCE: 81

Gln Ser Leu Leu Tyr Ser Glu Asn Lys Gln Asp Tyr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Consensus Sequence CDR1 of the light chain

<400> SEQUENCE: 82

Gln Ser Leu Leu Tyr Ser Glu Asn Asn Gln Asp Tyr
1               5                   10

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000
```

```
<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93
<211> LENGTH: 9
<212> TYPE: PRT
<213> ORGANISM: Artificial Sequence
<220> FEATURE:
<223> OTHER INFORMATION: Clone 14D3 CDR3 of the light chain

<400> SEQUENCE: 93

Glu Gln Thr Tyr Ser Tyr Pro Tyr Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Clone 14D8 CDR3 of the light chain

<400> SEQUENCE: 94

Glu Gln Thr Tyr Ser Tyr Pro Tyr Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Clone 7A12 CDR3 of the light chain

<400> SEQUENCE: 95

Glu Gln Thr Tyr Ser Tyr Pro Tyr Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Clone 8A11 CDR3 of the light chain

<400> SEQUENCE: 96

Glu Gln Thr Tyr Ser Tyr Pro Tyr Thr
1               5
```

```
<210> SEQ ID NO 97
<211> LENGTH: 9
<212> TYPE: PRT
<213> ORGANISM: Artificial Sequence
<220> FEATURE:
<223> OTHER INFORMATION: Clone 21A3 CDR3 of the light chain

<400> SEQUENCE: 97

Glu Gln Thr Tyr Ser Tyr Pro Tyr Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Clone 10C3 CDR3 of the light chain

<400> SEQUENCE: 98

Glu Gln Thr Tyr Ser Tyr Pro Tyr Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Clone 18F9 CDR3 of the light chain

<400> SEQUENCE: 99

Glu Gln Thr Tyr Ser Tyr Pro Tyr Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Clone 15C5 CDR3 of the light chain

<400> SEQUENCE: 100

Glu Gln Thr Tyr Ser Tyr Pro Tyr Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Clone 1G6 CDR3 of the light chain

<400> SEQUENCE: 101

Glu Gln Thr Tyr Ser Tyr Pro Tyr Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Consensus Sequence CDR3 of the light chain

<400> SEQUENCE: 102

Glu Gln Thr Tyr Ser Tyr Pro Tyr Thr
1               5
```

-continued

```
<210> SEQ ID NO 103
<211> LENGTH: 13
<212> TYPE: PRT
<213> ORGANISM: Artificial Sequence
<220> FEATURE:
<223> OTHER INFORMATION: First part of TREM2 WT CTF Flag

<400> SEQUENCE: 103

Ser Ile Ser Arg Ser Leu Leu Glu Gly Glu Ile Pro Phe
1               5                   10

<210> SEQ ID NO 104
<211> LENGTH: 8
<212> TYPE: PRT
<213> ORGANISM: Artificial Sequence
<220> FEATURE:
<223> OTHER INFORMATION: Last part of TREM2 WT CTF Flag

<400> SEQUENCE: 104

Asp Tyr Lys Asp Asp Asp Asp Lys
1               5

<210> SEQ ID NO 105
<211> LENGTH: 9
<212> TYPE: PRT
<213> ORGANISM: Artificial Sequence
<220> FEATURE:
<223> OTHER INFORMATION: First part of Flag-TREM2(133-157)

<400> SEQUENCE: 105

Gly Asp Tyr Lys Asp Asp Asp Asp Lys
1               5

<210> SEQ ID NO 106
<211> LENGTH: 9
<212> TYPE: PRT
<213> ORGANISM: Artificial Sequence
<220> FEATURE:
<223> OTHER INFORMATION: Last part of Flag-TREM2(133-157)

<400> SEQUENCE: 106

Ser Phe Glu Asp Ala His Val Glu His
1               5

<210> SEQ ID NO 107
<211> LENGTH: 13
<212> TYPE: PRT
<213> ORGANISM: Artificial Sequence
<220> FEATURE:
<223> OTHER INFORMATION: First part of TREM2 WT CTF

<400> SEQUENCE: 107

Ser Ile Ser Arg Ser Leu Leu Glu Gly Glu Ile Pro Phe
1               5                   10

<210> SEQ ID NO 108
<211> LENGTH: 9
<212> TYPE: PRT
<213> ORGANISM: Artificial Sequence
<220> FEATURE:
<223> OTHER INFORMATION: Last part of TREM2 WT CTF

<400> SEQUENCE: 108

Gln Thr Leu Pro Gly Leu Arg Asp Thr
1               5

<210> SEQ ID NO 109
```

```
<211> LENGTH: 13
<212> TYPE: PRT
<213> ORGANISM: Artificial Sequence
<220> FEATURE:
<223> OTHER INFORMATION: First part of TREM2 WT CTF Flag L163

<400> SEQUENCE: 109

Leu Glu Gly Glu Ile Pro Phe Pro Pro Thr Ser Ile Leu
1               5                   10

<210> SEQ ID NO 110
<211> LENGTH: 8
<212> TYPE: PRT
<213> ORGANISM: Artificial Sequence
<220> FEATURE:
<223> OTHER INFORMATION: Last part of TREM2 WT CTF Flag L163

<400> SEQUENCE: 110

Asp Tyr Lys Asp Asp Asp Asp Lys
1               5

<210> SEQ ID NO 111
<211> LENGTH: 13
<212> TYPE: PRT
<213> ORGANISM: Artificial Sequence
<220> FEATURE:
<223> OTHER INFORMATION: First part of TREM2 WT CTF Flag L164

<400> SEQUENCE: 111

Glu Gly Glu Ile Pro Phe Pro Pro Thr Ser Ile Leu Leu
1               5                   10

<210> SEQ ID NO 112
<211> LENGTH: 8
<212> TYPE: PRT
<213> ORGANISM: Artificial Sequence
<220> FEATURE:
<223> OTHER INFORMATION: Last part of TREM2 WT CTF Flag L164

<400> SEQUENCE: 112

Asp Tyr Lys Asp Asp Asp Asp Lys
1               5

<210> SEQ ID NO 113
<211> LENGTH: 13
<212> TYPE: PRT
<213> ORGANISM: Artificial Sequence
<220> FEATURE:
<223> OTHER INFORMATION: First part of TREM2 WT CTF Flag - E165

<400> SEQUENCE: 113

Gly Glu Ile Pro Phe Pro Pro Thr Ser Ile Leu Leu Leu
1               5                   10

<210> SEQ ID NO 114
<211> LENGTH: 8
<212> TYPE: PRT
<213> ORGANISM: Artificial Sequence
<220> FEATURE:
<223> OTHER INFORMATION: Last part of TREM2 WT CTF Flag E165

<400> SEQUENCE: 114

Asp Tyr Lys Asp Asp Asp Asp Lys
1               5

<210> SEQ ID NO 115
<211> LENGTH: 30
```

```
<212> TYPE: PRT
<213> ORGANISM: Artificial Sequence
<220> FEATURE:
<223> OTHER INFORMATION: Peptide used for immunization to generate
      cleavage-site-specific antibodies

<400> SEQUENCE: 115

Glu Asp Ala His Val Glu His Ser Ile Ser Arg Ser Leu Leu Glu Gly
1               5                   10                  15

Glu Ile Pro Phe Pro Pro Thr Ser Ile Leu Leu Leu Ala
            20                  25              30

<210> SEQ ID NO 116
<211> LENGTH: 9
<212> TYPE: PRT
<213> ORGANISM: Artificial Sequence
<220> FEATURE:
<223> OTHER INFORMATION: HA-tag

<400> SEQUENCE: 116

Tyr Pro Tyr Asp Val Pro Asp Tyr Ala
1               5

<210> SEQ ID NO 117
<211> LENGTH: 8
<212> TYPE: PRT
<213> ORGANISM: Artificial Sequence
<220> FEATURE:
<223> OTHER INFORMATION: linker sequence

<400> SEQUENCE: 117

Ser Gly Gly Gly Gly Gly Leu Glu
1               5

<210> SEQ ID NO 118
<211> LENGTH: 8
<212> TYPE: PRT
<213> ORGANISM: Artificial Sequence
<220> FEATURE:
<223> OTHER INFORMATION: C-terminal FLAG tag

<400> SEQUENCE: 118

Asp Tyr Lys Asp Asp Asp Asp Lys
1               5
```